United States Patent [19]
Nakata et al.

[11] Patent Number: 5,781,294
[45] Date of Patent: *Jul. 14, 1998

[54] METHOD AND APPARATUS FOR DETECTING PHOTOACOUSTIC SIGNAL TO DETECT SURFACE AND SUBSURFACE INFORMATION OF THE SPECIMEN

[75] Inventors: Toshihiko Nakata; Takanori Ninomiya, both of Hiratsuka; Hilario Haruomi Kobayashi, Yokohama; Kazushi Yoshimura, Kamakura, all of Japan

[73] Assignee: Hitachi, Ltd., Tokyo, Japan

[*] Notice: The term of this patent shall not extend beyond the expiration date of Pat. No. 5,479,259.

[21] Appl. No.: 548,015

[22] Filed: Oct. 25, 1995

Related U.S. Application Data

[63] Continuation-in-part of Ser. No. 994,150, Dec. 21, 1992, Pat. No. 5,479,259, which is a continuation-in-part of Ser. No. 886,014, May 20, 1992, Pat. No. 5,377,006.

[30] Foreign Application Priority Data

| Dec. 24, 1991 | [JP] | Japan | 3-340646 |
| Dec. 24, 1991 | [JP] | Japan | 3-340647 |
| Mar. 17, 1992 | [JP] | Japan | 4-060130 |
| Aug. 23, 1995 | [JP] | Japan | 7-214424 |

[51] Int. Cl.$^6$ ............................................. G01B 9/02
[52] U.S. Cl. ............................. 356/349; 356/357
[58] Field of Search ..................... 356/357, 359, 356/360, 432 T, 349; 73/655, 657

[56] References Cited

U.S. PATENT DOCUMENTS 5,479,259 12/1995 Nakata et al. .................. 356/357

OTHER PUBLICATIONS

"Non–destructive Examination", vol. 36, No. 10, pp. 730–736, Oct. 62.

IEEE 1986 Ultrasonics Symposium pp. 515–526, 1986.

*Primary Examiner*—Samuel A. Turner
*Attorney, Agent, or Firm*—Fay Sharpe Beall Fagan Minnich & McKee

[57] ABSTRACT

A method and an apparatus for detecting a photoacoustic signal are provided which irradiate an excitation light beam, modulated by a desired frequency, simultaneously to a plurality of points being measured on a surface of a sample, irradiate the excitation light and a probe light simultaneously to the plurality of the points being measured, detect an interference light of a reflected light beam of the probe light and a specified reference light with a detector made up of a plurality of photoelectric converting elements corresponding to the respective points being measured, the detector being in conjugate relation with the surface of the sample, detect a thermal distortion of the frequency component equal to the intensity-modulated frequency at the plurality of the points being measured from the interference light intensity signal detected by the detector, and detect information relative to the surface and the subsurface of the measuring points on the sample from the thermal distortion of the frequency component. A plurality of measuring points on a specimen are excited simultaneously with an intensity-modulated flat light beam and the thermal expansion displacements of the measuring points are detected simultaneously by interference between a flat probe light beam and a flat reference light beam to detect photothermal displacement signals representing the photothermal displacements of the plurality of measuring points simultaneously.

25 Claims, 49 Drawing Sheets

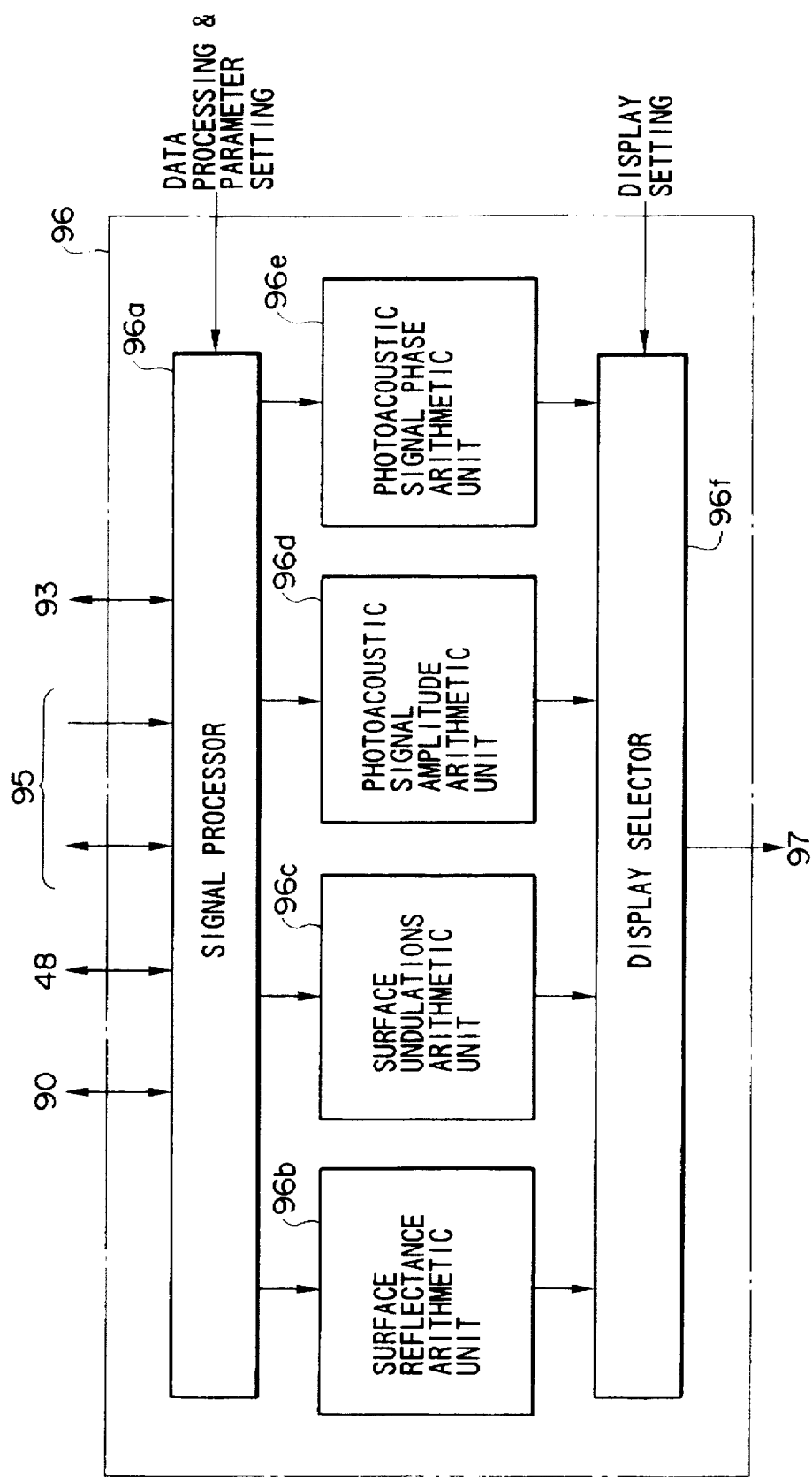

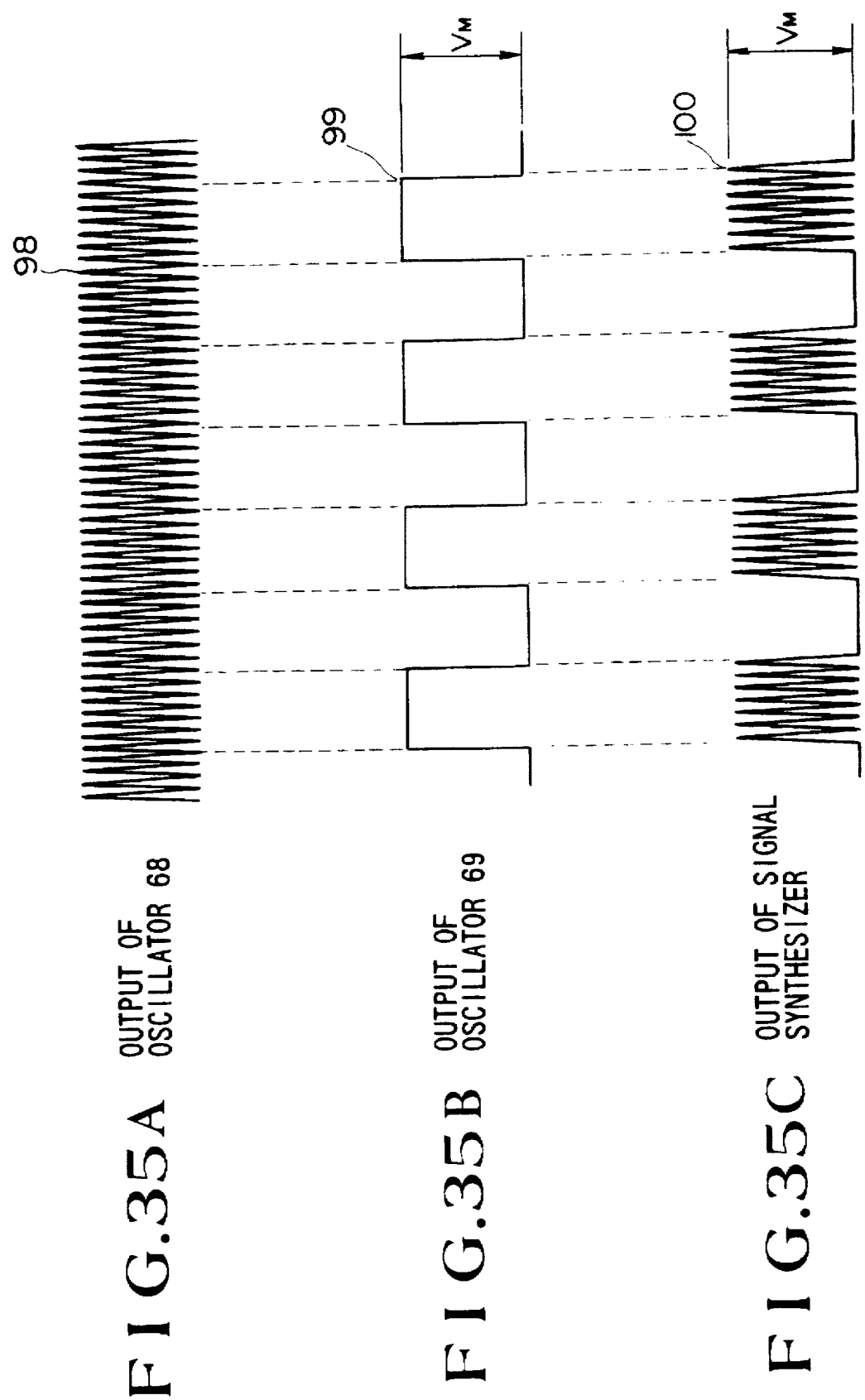

F I G. 38 A
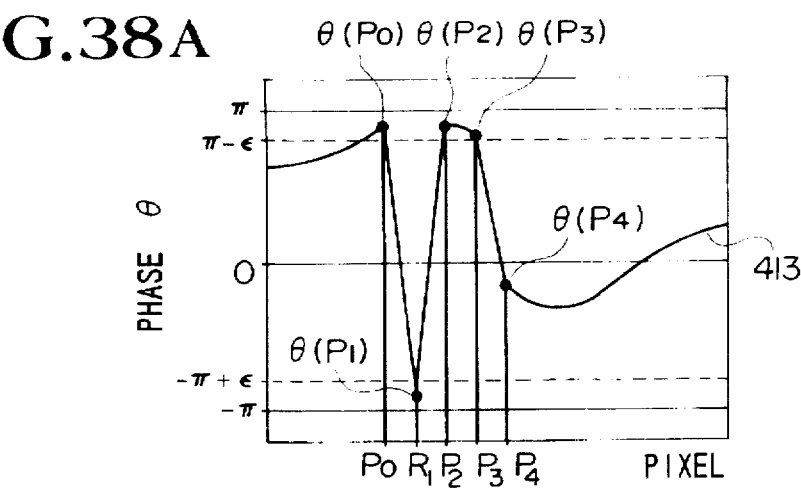
F I G. 38 B
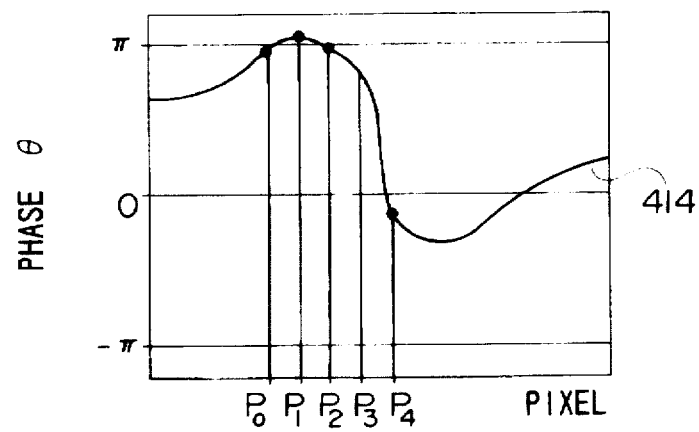
F I G. 39
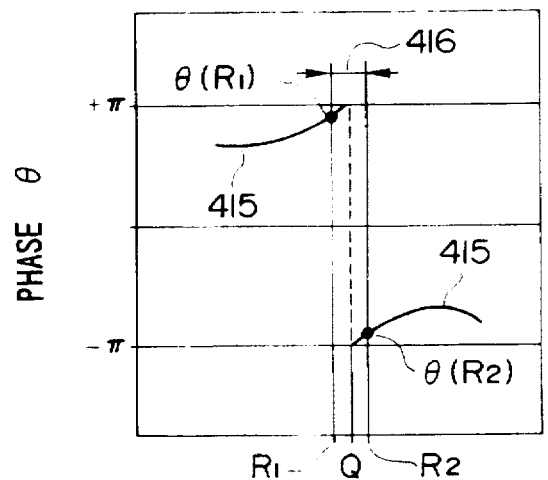

F I G. 43A
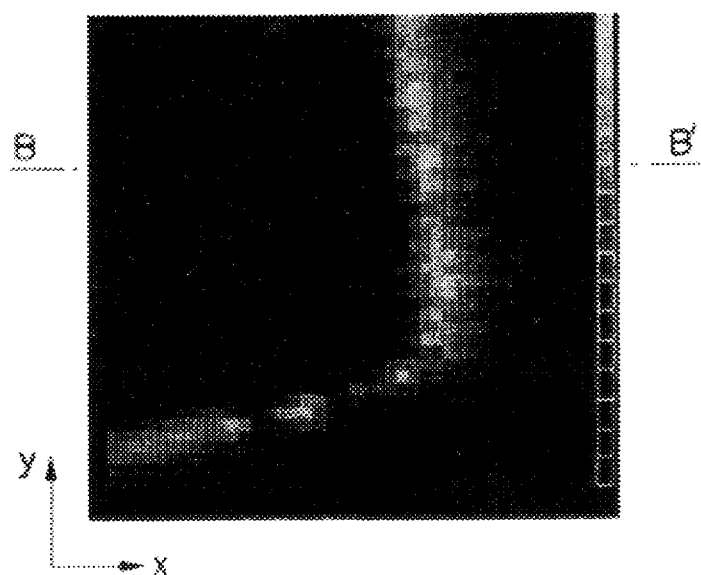

METHOD AND APPARATUS FOR DETECTING PHOTOACOUSTIC SIGNAL TO DETECT SURFACE AND SUBSURFACE INFORMATION OF THE SPECIMEN

CROSS-REFERENCE TO RELATED APPLICATION

This is a continuation-in-part of U.S. application Ser. No. 07/994,150, filed on Dec. 21, 1992, now U.S. Pat. No. 5,479,259, which is a continuation-in-part of U.S. application Ser. No. 07/886,014, filed on May 20, 1992, now U.S. Pat. No. 5,377,006, the disclosure of which is hereby incorporated by reference.

BACKGROUND OF THE INVENTION

The present invention relates to a method and an apparatus for detecting a photoacoustic signal to information relative to the surface and the subsurface of a sample using photoacoustic or photothermal effect, and more particularly to a method and an apparatus for detecting a photoacoustic signal, devised to effectively correct abnormality of phase shifts by phase jumps at specified points of the sample when a photoacoustic signal is detected at those points of the sample.

Furthermore the present invention relates to a photothermal displacement image detecting method and a photothermal displacement image detecting apparatus for detecting information about the surface and a subsurface layer of a specimen by a photoacoustic photothermal displacement method.

The photoacoustic effect was discovered by Tyndall, Bell, Roentgen, et al. in 1881. As shown in FIG. 2, when intensity-modulated light (intermittent light beam) 19 is irradiated to a sample 7 by focusing the light as an excitation light with a lens 5, heat is generated in a light absorption region $V_{OP}21$, and periodically diffused through a thermal diffusion region $V_{th}23$ defined by a thermal diffusion length $\mu_s 22$ so that the resulting thermal distortion wave gives rise to a thermoelastic wave (ultrasonic wave). By detecting this ultrasonic wave, i.e. a photoacoustic wave by a microphone (acousto-electric converter) or by a piezo-electric or a light interferometer to thereby obtain a signal component synchronized with the modulated frequency of the excitation light, information relative to the surface and subsurface of the sample can be obtained. Incidentally, the thermal diffusion length $\mu_s 22$ can be obtained by the following expression (1) from the thermal conductivity k, density ρ, and specific heat c of the sample 7 when the modulated frequency of the excitation light is denoted by $f_L$.

$$\mu_s = \sqrt{\frac{k}{\pi f_L c}} \quad (1)$$

A technique for detecting the above photoacoustic signal is disclosed, for example, in "HIHAKAI KENSA", Vol. 36, No. 10 issue, pp. 730–736 October 1987 (Showa 62) or IEEE 1986 ULTRASONIC SYMPOSIUM pp. 515–526 (1986).

Referring to FIG. 1, one example of such a technique will be explained. A parallel light beam emitted from a laser 1 is intensity-modulated by an acousto-optical modulator (AO modulator) 2. Then thus obtained intermittent light is expanded to a parallel beam of a desired diameter by a beam expander 3, which is reflected by a half mirror 4, and then focused by a lens 5 on the surface of the sample 7 placed on an X-Y stage 6. The thermal distortion wave emanating from the focusing position 21 on the sample 7 generates a thermoelastic wave, thus causing minute displacements at the surface of the sample. The minute displacements will be detected by a Michelson interferometer explained below. After the parallel light beam from the laser 8 is expanded to a desired beam diameter by the beam expander 9, the beam is separated into two beams traveling along two optical paths by a beam splitter or a half mirror 10. One is focused at the focusing position 21 on the sample by the lens 5, while the other is irradiated to a reference mirror 11. Then, the light reflected from the sample 7 and the light reflected from the reference mirror 11 interfere with each other at the half mirror 10. The interference light is focused by a lens 12 on a photoelectric converting element 13 such as a photodiode by a lens 12 to provide a photoelectric-converted interference intensity signal. After amplified by a preamplifier 14, the interference intensity signal is sent to a lock-in amplifier 16. Using a modulation frequency signal from an oscillator 15 used to drive the acousto-optical modulator 2 as a reference signal, the lock-in amplifier 16 extracts only the modulated frequency component contained in the interference intensity signal. This frequency component has information relative to the surface or the inside of the sample 7. According to the expression (1), by varying the modulated frequency, the thermal diffusion length $\mu_s 21$ can be changed and information as to the condition through the depth of the sample can be obtained. If there is a defect such as a crack in the thermal diffusion region $V_{th}23$, the amplitude of the modulated frequency component in the interference light intensity signal and the phase thereof relative to the modulation frequency signal change, by which the presence of the defect can be known. An X-Y stage shifting signal and an output signal from the lock-in amplifier 16 are processed by a computer 17. Accordingly, the photoacoustic signal corresponding to the respective points on the sample can be gathered and displayed as a two-dimensional image on a display 18 such as a monitor television.

Though the above-mentioned prior-art technique is extremely effective means for detecting a photoacoustic signal in non-contact and non-destructive inspection of samples, but has the following problems.

In the conventional photoacoustic detection optical system as shown in FIG. 1, when a two-dimensional internal information of a sample is to be obtained, it is necessary to perform a two-dimensional scanning of the surface of a sample by a relative motion of two beams, that is, an excitation light for generating a photoacoustic effect and a probe light for detecting minute displacements of the sample surface caused by the photoacoustic effect. This two-dimensional scanning is the so-called point scanning by which information is obtained point by point, and therefore, if one tries to scan the whole surface of the sample, a very large amount of detection time is required. This necessity for a large amount of detection time is the greatest reason why the photoacoustic detection technique has not been applied to internal defect inspection of samples in the production line. In some samples, the reflectance of the surface varies with different positions of the sample. In such a case, with the prior-art technique, the intensity of the reflected light of the probe light unavoidably contains information relative to the surface reflectance in addition to information about the internal condition, so that it is difficult to accurately detect only information about the inside of the sample. Furthermore, in some samples, the surface is not flat and has local undulations. In this case, in the prior-art technique, the phase of the reflected beam of the probe light varies according to the undulations of the sample surface, so that the reflected light intensity includes information with regard to the surface undulations in addition to internal information and, as a result, it is difficult to accurately detect only internal information about the internal condition.

Moreover, in the conventional photoacoustic signal detection method, there is no way to cope with the phenomenon called "phase jump". Suppose a case in which a photoacoustic signal is detected from a sample 200 having a crack 109 in the surface, as shown in FIG. 3A, for example. FIG. 3B shows a longitudinal sectional view taken along the line A-A' in FIG. 3A, while FIG. 4A shows a phase shift image (hereafter referred to as the phase image) of two-dimensional photoacoustic images of the sample 200. In the phase image, the thin white region corresponds to the crack 109, and in this region, there are several dark areas where the phase shift occurs sharply. FIG. 4B shows a phase shift signal 111 in a section taken along the line B-B' in FIG. 4A. As is apparent from this figure, there is a sharp phase jump in the dark areas, and in those areas, the phase signal 111 shows a sharp drop and rebound.

Generally, out of various photoacoustic signals, the phase signal has a characteristic that when the phase signal exceeds $+\pi$, the phase changes $-2\pi$ relative to the phase value, and similarly, when the phase signal exceeds $-\pi$, the phase changes $2\pi$ relative to the phase value. In this patent application, those changes are defined as the so-called "phase jump". This phase jump phenomenon occurs in the extraction of phase shift from the photoacoustic signal. More specifically, in the lock-in amplifier 16 in FIG. 1 the photoacoustic signal (interference intensity signal) is separated into a cosine component X and a sine component Y as shown by the expressions (1) and (2). The amplitude A and the phase $\theta$ of the photoacoustic signal can be obtained by the expressions (3) and (4).

$$X = A \cos \phi \quad (1)$$

$$Y = A \sin \phi \quad (2)$$

$$A = \sqrt{X^2 + Y^2} \quad (3)$$

$$\phi = \arctan\left(\frac{Y}{X}\right) \quad (4)$$

As shown in the expression (4), the phase shift $\theta$ can be obtained as an arctangent of a rate of the sine component Y to the cosine component X. As is well known, the principal value of the arctangent in this case exists in the range of $+\pi$ to $-\pi$. Therefore, for example, when the phase shift $\theta$ has a value $(\pi+\beta)$, which exceeds $+\pi$, the value output from the lock-in amplifier is $-\pi+\beta$, that is, $\pi+\beta$ added with $-2\pi$. Likewise, when the phase shift has a value $(-\pi-\beta)$ less than $-\pi$, the output value is $\pi-\beta$, that is, $-\pi-\beta$ added with $+2\pi$. In this way, a phase jump occurs. Therefore, when a phase jump has occurred at a sampling point, the real situation is that the phase shift at this sampling point does not contain a correct phase shift information, and for this reason, information relative to the surface and the inside of the sample cannot be obtained securely.

Furthermore, as shown in FIG. 54, a conventional photothermal displacement method projects an intensity-modulated light beam 601 on a specimen 602 and obtains information about the interior of the specimen 602 from the periodic variation of the thermal expansion displacement surface of the specimen 602 caused by a heat wave 603. The amplitude and the phase of the thermal expansion displacement 604 are greatly dependent on the heat conductivities of the surface and the interior of the specimen 602. For example, since the heat conductivity of a defective part 605 including a lattice defect in the crystal structure or a fault in a semiconductor wafer is lower than that of the normal part, the amplitude of the thermal expansion displacement of a point corresponding to the defective part 605 is greater than that of other points and the phase of the same thermal expansion is delayed. Therefore, the defective part 605 can be discriminated from other parts by scanning the surface of the specimen 602 with the intensity-modulated light beam 601 and measuring the thermal expansion displacements 604 of points on the surface of the specimen 602. This conventional photothermal displacement method is discussed in, for example, "IEEE 1986 Ultrasonics Symposium" pp. 515–526 (1986).

Generally, a thermal expansion displacement, i.e., an object of measurement, is on the order of subnanometers or less and, in most cases, such a minute thermal expansion displacement is absorbed in noise in an interference signal, such as due to the fluctuation of the ambient air or the vibrations of the stage of the measuring apparatus. Usually, synchronous detection using a lock-in amplifier is employed for extracting the amplitude or the phase of such a minute periodic component from an interference signal. When a modulating frequency on the order of several tens kilohertz is employed, the time constant of the lock-in amplifier must be several hundreds milliseconds to measure a minute signal of such an order. However, it takes enormous time to measure a two-dimensional area by the conventional photothermal displacement method employing a lock-in amplifier having such a time constant that repeats a measuring cycle in which the specimen is shifted every time one point is measured. For example, when a lock-in amplifier having a time constant of 400 ms is employed, it takes a very long time of about 7.3 hr to measure an area having 256×256 measuring points.

Although effective in evaluating physical properties and measuring defects in surface layers, the photothermal displacement method has not yet been prevalently applied to practical uses in the image measuring field. The enhancement of measuring speed without reducing sensitivity is the most significant problem in the photothermal displacement method.

SUMMARY OF THE INVENTION

Therefore, an object of the present invention is to provide a method and an apparatus, in a simple arrangement, for detecting a photoacoustic signal, which are less susceptible to effects of the reflectance distribution and the undulations distribution and which enable high-speed detection of two-dimensional internal information of a sample.

In order to achieve the above object, in accordance with the present invention, an intensity-modulated light is irradiated to a plurality of points being measured on a surface of a sample to generate a photoacoustic effect or a photothermal effect either on the surface or the inside of the plurality of points being measured, and at the same time, a light beam is irradiated to a plurality of points being measured, the reflected light and a reference light are made to interfere with each other, the resulting interference light is detected by a detector in a conjugate relation with the surface of the sample, said detector comprising a plurality of photoelectric converting elements corresponding to the respective points being measured, and from the detected interference light intensity signal, thermal distortion of the frequency component equal to the above-mentioned intensity-modulated frequency at the plurality of points being measured is detected. This method enables almost simultaneous extraction of information relative to the surface and the inside of a plurality of points being measured of a sample, and also enables detection of a photoacoustic signal at far higher speed than in the prior-art detection method.

Further, in order to achieve the above object, according to the present invention, the intensity-modulated light irradiated to the sample is formed as a continuous and straight beam on the sample, and a plurality of points being measured on the sample can be excited simultaneously, so that a photoacoustic signal can be detected at far higher speed than in the prior-art technique.

Further, in order to achieve the above object, according to the present invention, the intensity-modulated light, irradiated to the sample, is formed in a straight row of spot beams arranged on the sample, a plurality of points being measured on the sample can be excited simultaneously, so that a photoacoustic signal can be detected at far higher speed than in the prior-art technique.

In order to achieve the above object, according to the present invention, the above-mentioned spot beams in a row are arranged at such intervals that thermal diffusion regions by the spot beams do not overlap one another, thus improving the detection resolution of a photoacoustic image.

In order to achieve the above object, according to the present invention, by using a detector comprising a plurality of storage type photoelectric converting elements for detecting an interference light, a photoacoustic signal can be detected at far higher speed than in the prior-art method.

In order to achieve the above object, according to the present invention, by using a detector comprising a plurality of non-storage type photoelectric converting elements for detecting an interference light, a photoacoustic signal can be detected at far higher speed than in the prior-art method.

In order to achieve the above object, according to the present invention, by using a detector comprising a plurality of non-storage type photoelectric converting elements for detecting an interference light, a photoacoustic signal can be detected at far higher speed than in the prior-art method.

In order to achive the above object, according to the present invention, by using a detector which outputs an interference light intensity signal from a plurality of photoelectric converting elements as a one-dimensional signal in time sequence, a photoacoustic signal can be detected at far higher speed than in the prior-art method.

In order to achieve the above object, according to the present invention, by using a detector which does parallel and simultaneous output of an interference light intensity signal from a plurality of photoelectric converting elements, a photoacoustic signal can be detected at far higher speed than in the prior-art method.

In order to achieve the above object, according to the present invention, by using a detector comprising a plurality of storage type photoelectric converting elements to detect an interference light, the interference light intensity signal, which is stored in a desired storage time and output from each of the storage type photoelectric converting elements of the detector, is detected 2n (n: arbitrary integer.>0) times by shifting the phase of the signal by $\pi/n$ for each photoelectric converting element, and according to 2n pieces of signal data, the thermal distortion of the frequency component equal to the above-mentioned intensity-modulated frequency is calculated, and thereby use of a digital frequency filtering process is made possible instead of an analog frequency filtering process, so that detection of a photoacoustic signal can be performed with high sensitivity and high accuracy without being much affected by a high harmonic component. Furthermore, it is possible with only one detector to simultaneously detect a total of four items of information relative to the surface and the inside of the sample, namely, the reflectance distribution of the sample surface, the undulations distribution of the sample surface, the amplitude distribution of the photoacoustic signal, and the phase distribution of the photoacoustic signal, and thereby a high-speed complex characterization of a sample is made possible. Moreover, according to the present invention, it is possible to detect a photoacoustic signal in which corrections have been made to the reflectance distribution of the sample surface, the undulations distribution of the sample surface, and the optical path fluctuation, so that information relative to the surface and the inside of the sample can be detected with high sensitivity and stability.

In order to achieve the above object, according to the present invention, as a method for shifting the phase of the interference light intensity signal output from the detector, comprising the storage type photoelectric converting elements, by $\pi/n$ for each photoelectric converting element, a method is used in which a combination of desired values is set for the difference in light frequency between the reflected light from the above-mentioned sample surface and the reference light, the above-mentioned intensity-modulated frequency, and the storage time of the above-mentioned storage type photoelectric converting elements, and therefore, by using only one detector, it is possible to simultaneously detect a total of four items of information as to the surface and the inside of the sample, including the sample surface reflectance distribution, the sample surface undulations distribution, the photoacoustic signal amplitude distribution, and the phase distribution of the photoacoustic signal, and thereby a high-speed complex characterization of a sample is made possible. Also, it is possible to implement photoacoustic signal detection in which corrections have been made to the reflectance distribution of the sample surface, the undulations distribution of the sample surface, and the optical path fluctuation, so that information relative to the surface and the inside of a sample can be detected with high sensitivity and stability.

In order to achieve the above object, according to the present invention, from the interference light intensity signal output in parallel form simultaneously from the detector, the thermal distortion of the frequency component equal to the above-mentioned intensity-modulated frequency is detected with a plurality of photoelectric converting elements in parallel simultaneously.

In order to achieve the above object, according to the present invention, detection of the information of an interface inside the sample is possible by setting the intensity-modulated frequency so that the thermal diffusion length owing to the photoacoustic effect or the photothermal effect is equal to or longer than the depth of the interface in the inside being measured of the above-mentioned sample.

In a photoacoustic signal detection apparatus, by irradiating an intensity-modulated light to a plurality of points being measured on the surface of a sample, a photoacoustic effect or a photothermal effect can be generated at a plurality of points being measured, and at the same time, by irradiating the light to the plurality of points being measured and causing a reflected light from the points being measured and a reference light to interfere with each other, the resulting interference light is detected by a detector, which is in a conjugate relation with the sample surface, the detector comprising a plurality of photoelectric converting elements corresponding to the points being measured, and from the interference light intensity signal detected, and thermal distortion of a frequency component equal to the above-mentioned intensity-modulated frequency at the plurality of points being measured, and thereby information relative to the surface and the inside at the plurality of points being measured of the sample can be extracted substantially simultaneously as a photoacoustic signal, so that detection of a photoacoustic signal can be performed at far higher speed than in the prior-art method.

Further, since the intensity-modulated light is irradiated to the sample in a continuous, straight beam on the sample, the plurality of points being measured on the sample can be excited simultaneously, and detection of a photoacoustic signal can be performed at far higher speed than in the prior-art method.

Further, since the intensity-modulated light is irradiated to the sample in a row of spot beams arranged in a straight line on the sample, the plurality of points being measured on the sample can be excited simultaneously, and detection of a photoacoustic signal can be performed at far higher speed than in the prior-art method.

Further, since the spot beams in a row are arranged at such intervals that the thermal diffusion regions do not overlap each other, the photoacoustic signal can be detected independently from the respective points being measured, thereby improving the detection resolution of a photoacoustic image.

Further, a detector comprising a plurality of storage type photoelectric converting elements is used to detect an interference light, and therefore, the photoacoustic signal at the plurality of points being measured can be extracted substantially simultaneously, which enables detection of a photoacoustic signal at far higher speed than in the prior-art method.

Further, a detector comprising a plurality of non-storage type photoelectric converging elements are used to detect an interference light, and therefore, the photoacoustic signal at the plurality of points being measured is extracted substantially simultaneously, which enables detection of a photoacoustic signal at far higher speed than in the prior-art method.

Further, a detector is used which outputs an interference light intensity signal from a plurality of photoelectric converging elements as a one-dimensional signal in time sequence, and therefore, the photoacoustic signal at the plurality of points being measured can be extracted substantially simultaneously, which enables detection of a photoacoustic signal be performed at far higher speed than in the prior-art method.

Further, a detector is used which outputs an interference light intensity signal from a plurality of photoelectric converging elements in parallel simultaneously, and therefore, the photoacoustic signal at the plurality of points being measured can be extracted substantially simultaneously, which enables detection of a photoacoustic signal at far higher speed than in the prior-art method.

Further, since a detector comprising a plurality of storage type photoelectric converging elements is used to detect an interference light, the interference light intensity signal, which is stored in a desired storage time and output from each of the storage type photoelectric converging elements of the detector, is detected 2n times by shifting the phase of the signal by $\pi/n$ for each photoelectric converting element, and according to 2n pieces of signal data, the thermal distortion of the frequency component equal to the above-mentioned intensity-modulated frequency is calculated, and thereby use of a digital frequency filtering process is made possible instead of an analog frequency filtering process, so that detection of a photoacoustic signal can be performed with high sensitivity and high accuracy without being much affected by a high harmonic component. Furthermore, it is possible with only one detector to simultaneously detect a total of four items of information relative to the surface and the inside of the sample, namely, the reflectance distribution of the sample surface, the undulations distribution of the sample surface, the amplitude distribution of the photoacoustic signal, and the phase distribution of the photoacoustic signal, and thereby a high-speed complex assessment of a sample is made possible. Moreover, it is possible to detect a photoacoustic signal in which corrections have been made on the reflectance distribution of the sample surface, the undulations distribution of the sample surface, and the optical path fluctuation. Also, information relative to the surface and the inside of the sample can be detected with high sensitivity and stability.

As a method for shifting the phase of the interference light intensity signal output from the detector comprising the storage type photoelectric converting elements by $\pi/n$ for each photoelectric converting element, a method is used in which a combination of desired values is set for the difference in light frequency between the reflected light from the above-mentioned sample surface and the reference light, the above-mentioned intensity-modulated frequency, and the storage time of the above-mentioned storage type photoelectric converting elements, and therefore, by using only one detector, it is possible to simultaneously detect a total of four items of information relative to the surface and the inside of the sample, which includes the sample surface reflectance distribution, the sample surface undulations distribution, the photoacoustic signal amplitude distribution, and the phase distribution of the photoacoustic signal, and thereby a high-speed complex characterization of a sample is made possible. Also, it is possible to implement photoacoustic signal detection in which corrections have been made on the reflectance distribution of the sample surface, the undulations distribution of the sample surface, and the optical path fluctuation, so that information relative to the surface and the inside of a sample can be detected with high sensitivity and stability.

Further, from the interference light intensity signal output in parallel form simultaneously from the detector, the thermal distortion of the frequency component equal to the above-mentioned intensity-modulated frequency is detected with a plurality of photoelectric converting elements in parallel simultaneously.

Further, the information of an interface inside the sample can be detected by setting the intensity-modulated frequency so that the thermal diffusion length owing to the photoacoustic effect or the photothermal effect is equal to or longer than the depth of the interface in the inside being measured of the above-mentioned sample.

Further, another object of the present invention is to provide a method and an apparatus for detecting a photoacoustic signal, which enables information relative to the surface and the inside of a sample to be detected more stably and with higher accuracy by effectively correcting a phase jump in a phase shift when the phase shift is extracted from the photoacoustic signal.

The above object can be achieved by intensity-modulating a light beam from a light source by a desired frequency, scanning, focusing and irradiating the intensity-modulated light beam on a sample in two dimensions, generating a photoacoustic effect or a photothermal effect on the surface or the inside of the sample to cause a thermal distortion at the sample surface, detecting the thermal distortion at each sampling point, detecting the amplitude of the frequency component synchronized with the above-mentioned intensity-modulated frequency and a phase shift thereof relative to the above-mentioned intensity-modulated signal from the detected signal, detecting the presence or absence of a phase jump in the detected phase shift, correcting the abnormality of the phase shift signal caused by the phase jump when a phase jump is detected in the phase shift, and detecting information relative to the surface and the inside of the sample according to the amplitude and the corrected phase shift.

More specifically, the above object can be achieved by detecting whether a phase jump has occurred in the phase shift detected in each sampling point according to a change in the phase shift, and effectively correcting the abnormality of the phase shift caused by the phase jump at the sampling point where the phase jump has occurred by adding or subtracting $2\pi$ to or from the phase shift value at the sampling point according to the change of the phase shift.

Meanwhile, the photoacoustic signal detection apparatus comprises scanning, focusing and irradiating means for intensity-modulating the light from a light source by a desired frequency, scanning, focusing and irradiating the intensity-modulated light on the sample in two dimensions, and causing a thermal distortion on the sample surface by generating a photoacoustic effect or a photothermal effect at the surface or the inside of the sample; thermal distortion detecting means for detecting the thermal distortion at the sampling point caused by the scanning, focusing and irradiating means; amplitude and phase shift detecting means for detecting the amplitude of the frequency component synchronized with the intensity-modulated frequency and a phase shift thereof relative to the intensity-modulated signal from the thermal distortion signal detected by the detecting means; phase jump detecting means for detecting whether a phase jump has occurred in the phase shift detected by the phase detecting means; and correcting means for correcting the abnormality caused by the phase jump when the phase jump is detected in the phase shift by the phase jump detecting means, wherein information relative to the surface and the inside of the sample is detected according to the amplitude detected by the amplitude and detecting means and the phase shift corrected by the correcting means.

More specifically, the above object can be achieved by arranging for the phase jump detecting and correcting means of the photoacoustic signal detection apparatus to effectively correct the abnormality in the phase shift caused by the phase jump at the sampling point by detecting whether a phase jump has occurred in the phase shift detected at each sampling point according to a change of the phase shift, and adding or subtracting $2\pi$ to or from the phase shift value at the sampling point where the phase jump has occurred.

In other words, if the phase shift at some sampling point is recognized as a sharp drop or rise compared with the phase shift at a nearby sampling point under a certain condition, a decision is made that a phase jump occurred in the phase shift at that sampling point, the phase shift at the sampling point is corrected by adding $2\pi$ or $-2\pi$ to the phase value at the sampling point. By applying this correction process to the phase shifts at the sampling points which include a phase jump, from the phase shifts at those sampling points, information as to the surface and the subsurface of the sample can be obtained with improved stability and higher accuracy.

Furthermore, it is an object of the present invention to provide a photothermal displacement image detecting method capable of quickly obtaining information about the two-dimensional surface and the subsurface layer of a specimen, and a photothermal displacement image detecting apparatus of a simple construction suitable for carrying out the photothermal displacement image detecting method.

With the foregoing objects in view, the present invention provides a photothermal displacement image detecting method comprising: irradiating a plurality of measuring points on the surface of a specimen with a light beam intensity-modulated at variable frequency $f_E$ to cause periodic thermal expansion displacements in the surface at the plurality of measuring points; irradiating the measuring points with a second light beam and making a reference light beam of a frequency differing by $f_B$ interfere with the reflected second light beam; detecting interference light resulting from the interference between the reflected second light beams and the reference light beam by a detector comprising a plurality of photoelectric transducers respectively corresponding to the measuring points; detecting the intensity variation of the interference light due to the thermal expansion displacements of the measuring points from interference light intensity signals and providing a photothermal displacement signal representing the intensity variation of the interference light; and detecting information about the surface and a subsurface layer of the specimen at the plurality of measuring points from the photothermal displacement signal.

To achieve the objects, the intensity-modulated light beam employed in the present invention for irradiating the plurality of measuring points on the surface of the specimen is a flat beam that forms a continuous straight light line on the specimen.

To achieve the objects, the detector employed in the present invention integrates the interference light.

To achieve the objects, the detector employed in the present invention provides the interference light intensity signals in one-dimensional signals in a time series mode from the plurality of photoelectric transducers.

To achieve the objects, the present invention detects photothermal displacement signals representing the variations in the interference light intensity due to the thermal expansion displacements for the plurality of measuring points on the basis of a plurality of integrated detection data obtained by integrating the output of the photoelectric transducers of the detector a plurality of times at a period of b $1/f_S$ while the frequencies $f_S$, $f_B$ and $f_E$ are controlled at an integral ratio of 8p:8pu+1:8pv−1 or 8p:8pu−1:9pv+1, where p, u and v are integers other than zero.

To achieve the objects, the present invention projects the reference light beam so that the reference light beam falls on the surface of the specimen at a position at a distance approximately equal to or greater than the thermal diffusion length from the point irradiated with the intensity-modulated light beam.

To achieve the objects, the present invention determines the intensity-modulating frequency $f_E$ so that the thermal diffusion length due to photothermal or photoacoustic effect is approximately equal to or greater than the depth of the objective internal interface of the specimen.

To achieve the objects, the present invention provides a photothermal displacement image detecting apparatus comprising: a light source; an intensity modulating means for modulating the intensity of a light beam emitted by the light source at a variable frequency $f_E$; an exciting means for projecting the intensity-modulated light beam on the surface of a specimen at a plurality of measuring points to cause periodic thermal expansion displacements in the surface of the specimen at the plurality of measuring points; an interference light producing means for irradiating the plurality of measuring points with a second light beam, and making the reflected second light beam reflected by the measuring points interfere with a reference light beams of a frequency differing by $f_B$ to produce interference light; an interference light detecting means for detecting the interference light by a detector disposed in a conjugate relation with the surface of the specimen and comprising a plurality of photoelectric transducers respectively corresponding to the measuring points; an information detecting means for detecting photothermal displacement signals representing the variations in the intensity of the interference light due to thermal expansion displacements of the plurality of measuring points to detect information about the surface and a subsurface layer of the specimen at the plurality of measuring points from the photothermal displacement signals; a storage means for storing information about the surface and a subsurface layer of the specimen; and a display means for displaying the information about the surface and the subsurface of the specimen.

The photothermal displacement image detecting apparatus is capable of causing periodic thermal expansion displacements at the measuring points on the surface by irradiating the plurality of measuring points on the surface of the specimen with the light beam intensity-modulated at the variable frequency $f_E$, and of substantially simultaneously extracting information about the surface and the subsurface layer at the plurality of measuring points on the specimen by irradiating the measuring points with the second light beam to make the reference light beam of a frequency differing by $f_B$ interfere with the reflected second light beam, detecting interference light resulting from the interference between the reflected second light beams and the reference light beam by the detector comprising a plurality of photoelectric transducers respectively corresponding to the measuring points, detecting the intensity variation of the interference light due to the thermal expansion displacements of the measuring points from interference light intensity signals and providing a photothermal displacement signal representing the intensity variation of the interference light and detecting information about the surface and the subsurface layer of the specimen at the plurality of measuring points from the photothermal displacement signal.

The use of a flat light beam that forms a continuous straight light line on the surface of the specimen as the intensity-modulated light beam for irradiating the plurality of measuring points enables the detection of the photothermal displacement image at a very high measuring speed far higher than that of the conventional photothermal displacement image detecting method.

The integration of the interference light by the detector enables the high-speed detection of a photothermal displacement image in a high accuracy.

The use of the detector comprising the plurality of photoelectric transducers that provide the interference light intensity signals in one-dimensional signals in a time series mode enables the detection of the photothermal displacement image at a very high measuring speed far higher than that of the conventional photothermal displacement image detecting method.

To achieve the objects, the present invention controls the frequencies $f_S$, $f_B$ and $f_E$ at a fixed integral ratio of 8p:8pu+1:8pv−1 or 8p:8pu−1:8pv+1, where p, u and v are integers other than zero, and control signals for controlling the controlled components; and detects photothermal displacement signals representing the variations in the intensity of the interference light due to thermal expansion displacements of the plurality of measuring points on the basis of a plurality of integrated detection data obtained by integrating the outputs of each photoelectric transducer a plurality of times at a time period of $1/f_S$ to detect information about the surface and a subsurface layer of the specimen at the plurality of measuring points from the photothermal displacement signals. Therefore, the present invention is able to detect the photothermal displacement image at a very high measuring speed far higher than that of the conventional photothermal displacement image detecting method.

The projection of the reference light beam so that the reference beam falls on the surface of the specimen at a position at a distance approximately equal to or greater than the thermal diffusion length from the point irradiated with the intensity-modulated light beam enables the detection of a photothermal displacement image in a high measuring speed far higher than that of the conventional photothermal displacement image detecting method.

Since the intensity-modulating frequency $f_E$ is determined so that the thermal diffusion length due to photothermal or photoacoustic effect is approximately equal to or greater than the depth of the objective internal interface of the specimen, an optional subsurface layer at an optional depth of the specimen can be inspected.

BRIEF DESCRIPTION OF THE DRAWINGS

FIG. 5B is a diagram of a structural example of the processing unit in FIG. 5A;

FIGS. 35A, 35B, 35C are diagrams for explaining a method for forming an intensity modulating signal to the acousto-optical modulator element in FIG. 34;

FIGS. 38A and 38B are diagrams for explaining the method of making phase jump correction on the photoacoustic signal (phase signal) according to FIG. 33;

FIG. 39 is a diagram showing the relation among the phase jump and a sampling interval of the phase shift signal;

FIG. 43A is a two-dimensional photoacoustic image (phase image) after a phase jump correction process has been done on a photoacoustic signal (phase signal) by another method;

DESCRIPTION OF THE PREFERRED EMBODIMENTS

Figure 5A:
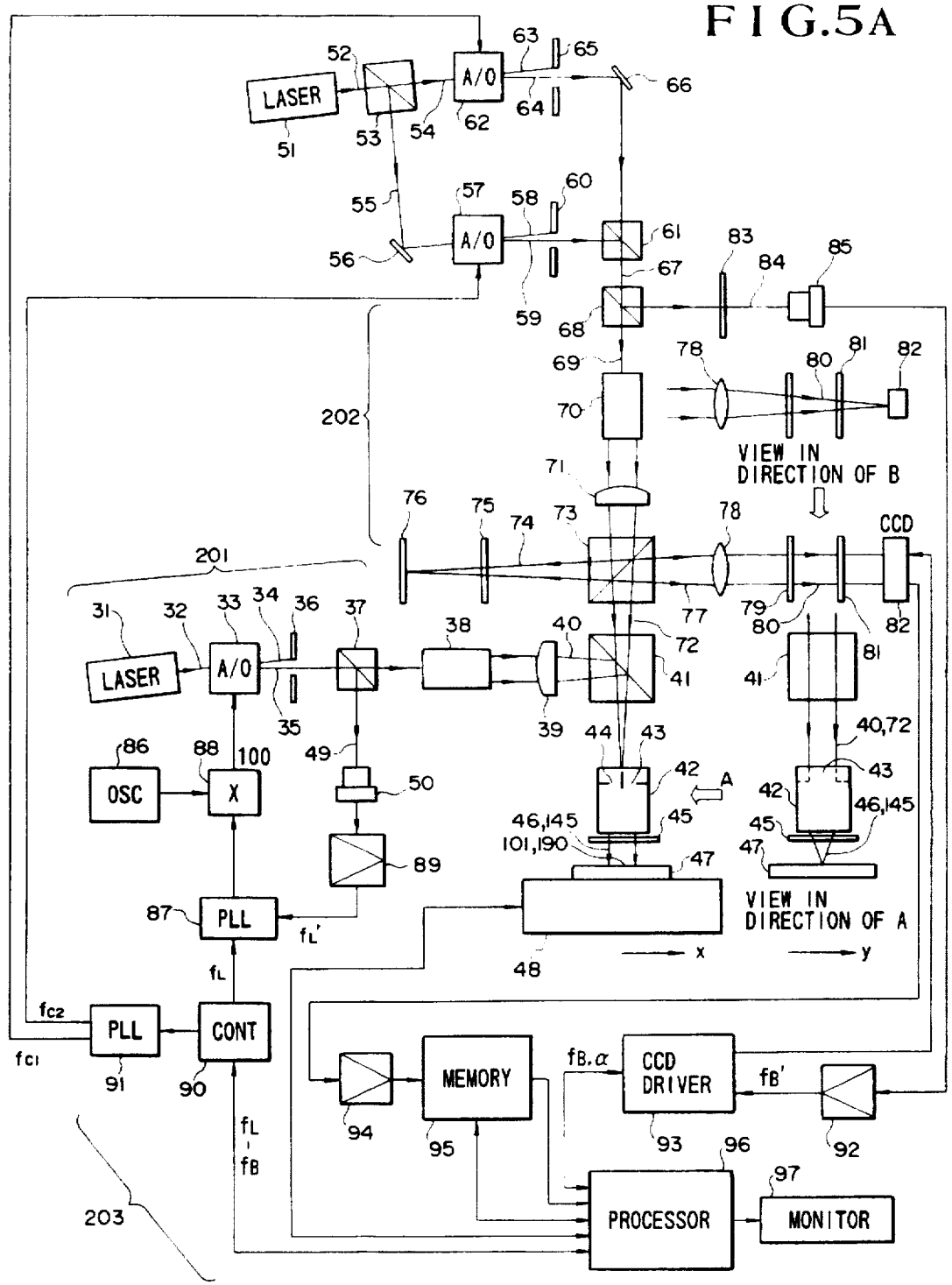
FIG. 5A is a structural diagram of the photoacoustic detection unit.
Figure 6A:
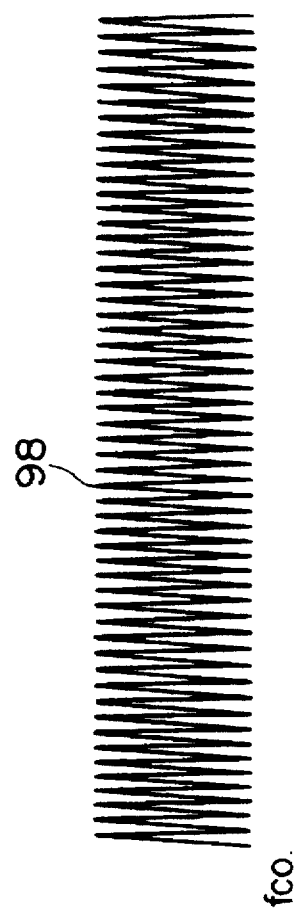
FIGS. 6A, 6B, and 6C are diagrams showing modulating signals input to the acousto-optical modulator element.
Figure 6B:
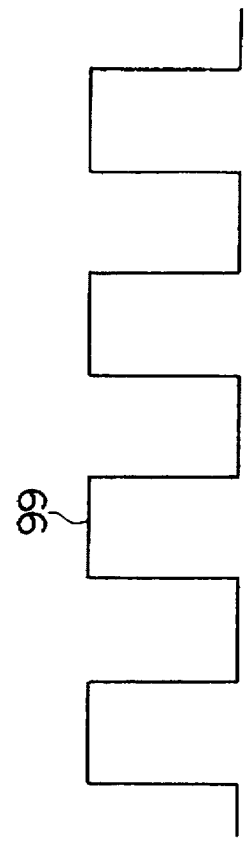
Figure 6C:
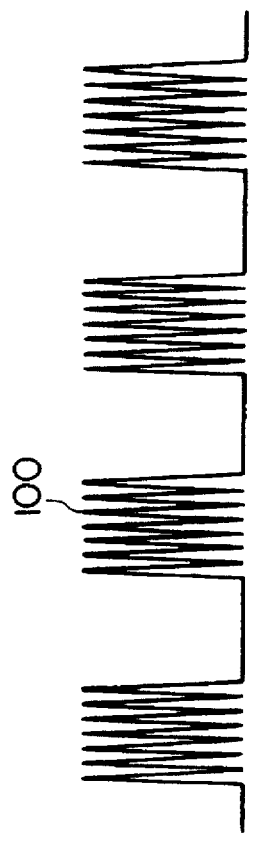
Figure 7A:
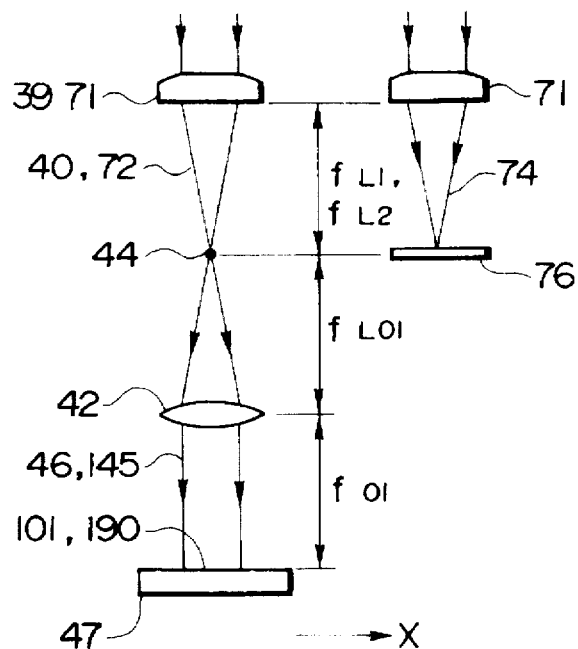
FIGS. 7A and 7B are structural diagrams of the excitation optical system and the heterodyne interferometric optical system in a first embodiment of the present invention.
Figure 7B:
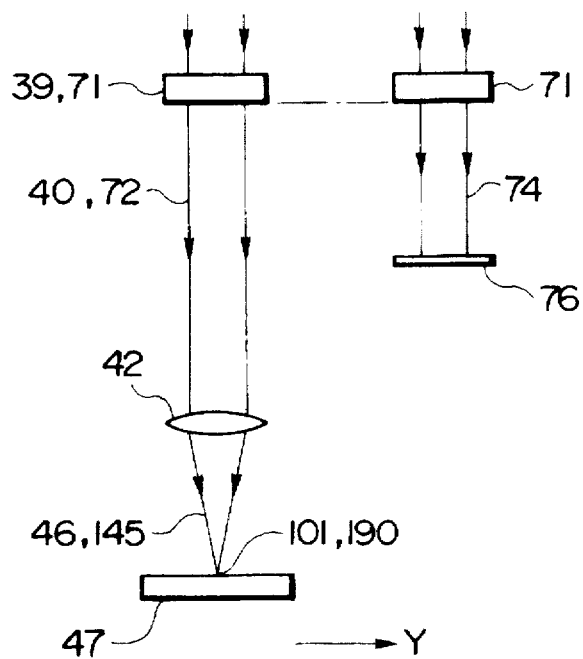
Figure 8:
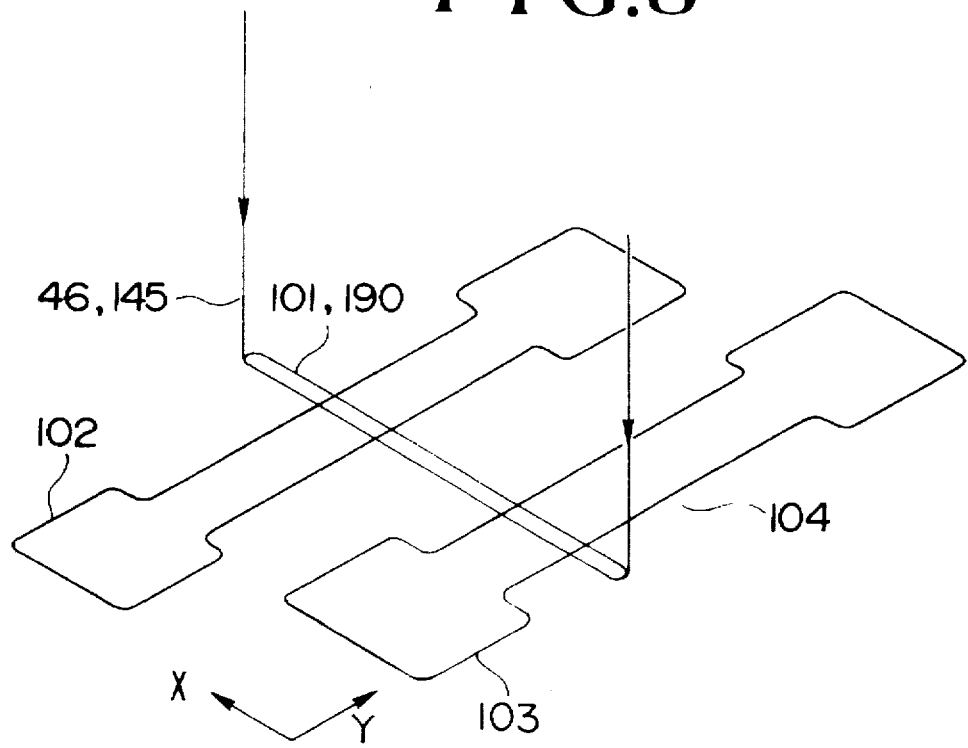
FIG. 8 is a perspective view showing a planar structure of a sample, an excitation beam and a probe beam in the first embodiment.

A first embodiment of the present invention will be described with reference to FIGS. 5A to 16C. FIG. 5A shows the photoacoustic detection optical system according to the first embodiment. This optical system includes an excitation optical system 201, a heterodyne Twyman-Green interferometric optical system 202 for detecting a photoacoustic signal, and a signal processing system 203. A parallel beam 32 emitted from an Ar laser 31 (wavelength 515 nm) of the excitation optical system 201 is incident on an acousto-excitation optical modulator 33. In FIG. 5A, a sine wave 98 with a frequency $f_{CO}$ shown in FIG. 6A and a square wave 99 with a frequency $f_L$ ($f_L < f_{CO}$) shown in FIG. 6B are respectively input to a signal synthesizer 88 to form a product of these two waveforms, which serves as a modulated signal 100 as shown in FIG. 6C, and this modulated signal 100 is input to the acousto-optical modulator 33. As a result, a first-order diffracted light 35, shifted in frequency by $f_{CO}$, is intermittently output with a frequency of $f_L$ from the acousto-optical modulator 33. In other words, as an excitation light, an intensity-modulated beam with a modulated frequency of $f_L$, shifted in frequency by $f_{CO}$, is obtained. A zero-order light 34 is intercepted by a diaphragm 36. After passing a beam splitter 37, the intensity-modulated beam 35 is expanded to a desired beam diameter by a beam expander 38, and caused to become an elliptic beam 40 by a cylindrical lens 39. Then, after reflected by a dichroic prism 41 (reflects wavelengths 600 nm or less, transmits wavelengths more than 600 nm), the elliptic beam 40 is focused only in the x-direction at a pupil 43, that is, the rear focal point 44 of an objective lens 42. With regard to the y-direction, since the cylindrical lens 39 can be regarded as a plate glass without a curvature, the elliptic beam is incident on the rear focal point 44 of the objective lens as a parallel light. In consequence, as shown in FIG. 8, a stripe beam 101 having a width in the x-direction and focused in the y-direction can be obtained as an excitation beam on the front focal point of the objective lens, that is, on the surface of a sample 47. Meanwhile, a light beam 49 which is about 10% of the intensity-modulated beam 35 is reflected by the beam splitter 37 and detected by a photoelectric converting element 50, such as a photodiode, and then, sent through an amplifier circuit 89 to the oscillator 87. At the oscillator 87, comparison is made between a set frequency $f_L$ supplied from a modulation signal control circuit 90 and a measured frequency $f_L'$ detected by the photoelectric converting element 50, and in order for the two frequencies to coincide with each other, the oscillated frequency is adjusted minutely. The oscillator 87 is formed by a PLL (Phase Locked Loop) circuit or the like.

Figures 9A, 9B:
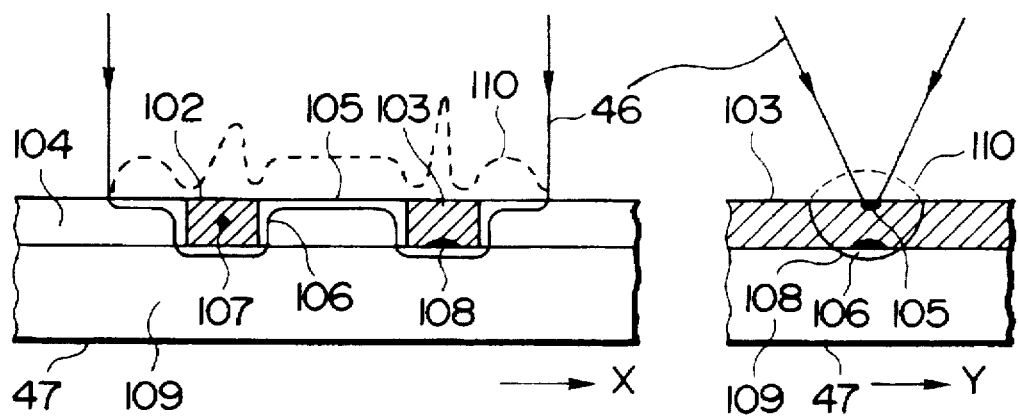
FIGS. 9A and 9B are diagrams showing the cross-sectional structures of the sample and the generated states of a photoacoustic effect by the excitation beam in a stripe form in the first embodiment.
Figure 10A:
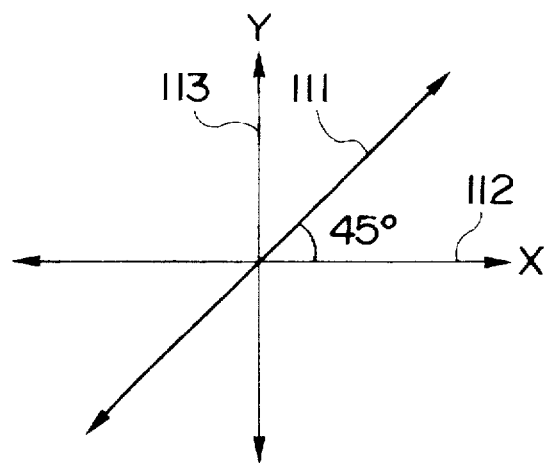
FIGS. 10A and 10B are diagrams showing the polarization direction of the laser beam incident on the heterodyne interference optical system and the orthogonal-polarized beams of two frequencies.

The excitation optical system 201 will be described with reference to FIGS. 7A and 7B. In FIGS. 7A and 7B, the focal point of the cylindrical lens 39 and the rear focal point 44 of the objective lens 42 coincide with each other, and the front focal point of the objective lens coincides with the surface of the sample 47. Therefore, as shown in FIG. 7A, as for the x-direction, because the beam 40 leaving the cylindrical lens 39 is focused at the rear focal point 44 of the objective lens 42, a beam 46 emerging from the objective lens 42 as a parallel light is incident on the surface of the sample 47. On the other hand, as shown in FIG. 7B, with regard to the optical path seen in the y-direction, since the cylindrical lens 39 can be regarded as a plate glass without a curvature, the beam 40 leaving the cylindrical lens 39 enters the objective lens 42 as a parallel light, and therefore, the beam 46 emerging from the objective lens 42 is focused on the surface of the sample 47. Consequently, as shown in FIG. 8, on the surface of the sample 47, a stripe beam 101 having a width in the x-direction and focused in the y-direction can be obtained as an excitation beam. Suppose Cu wiring patterns 102 and 103 are formed using an organic polymeric material 104, say, polyimide as an insulator as shown in FIG. 8. FIGS. 9A and 9B are sectional views showing an internal structure of the sample and heat diffusion regions produced by the excitation beam. The sample 47 has a structure in which Cu wiring patterns 102 and 103 with a thickness of 20 µm are formed on a ceramic substrate 109 with a 20-µm-thick polyimide 104 used as an insulator. Internal defects to be detected include an internal crack 107 in the Cu wiring pattern and separation 108 of the interface between the substrate and Cu pattern. An important point here is a difference in thermal properties between the Cu patterns 102 and 103, and the polyimide 104 surrounding the patterns. To be more specific, in the case of Cu, the thermal conductivity k is 403 $|J \cdot m^{-1} \cdot k^{-1} \cdot s^{-1}|$, the density $\rho$ is 8.93 $|X10^6 g \cdot m^{-3}|$, and the specific heat c is 0.38 $|J \cdot g^{-1} \cdot k^{-1}|$, while in the case of polyimide, the thermal conductivity k is 0.288 $|J \cdot m^{-1} k^{-1} \cdot s^{-1}|$, the density $\rho$ is 1.36 $|X10^6 g \cdot m^{-3}|$, and the specific heat c is 1.13 $|J \cdot m^{-1} \cdot k^{-1}|$. A notable difference, above all else, is the heat conductivity k of Cu is 1400 times greater than that of polyimide. So, if the intensity-modulated frequency $f_L$ of the excitation light is 50 kHz and the above values are substituted into the expression (1), the thermal diffusion length $\mu_S$ in the Cu patterns 102 and 103 is about 27 µm, and that of the polyimide portion 104 is about 1.1 µm. Consequently, as shown in FIGS. 9A and 9B, heat given in the light absorption region 105 in a stripe formed by the stripe-shaped excitation beam 101 is diffused widely in the Cu patterns 102 and 103 under inspection, and a heat diffusion region 106 is formed in a manner to extend across the section of the Cu pattern including the interface with the substrate. On the other hand, in the polyimide portion 104 excluded from the scope of inspection, heat is diffused in a small area, and the heat diffusion region is formed only in the surface area. Therefore, as shown in FIGS. 8, 9A and 9B, if the stripe-shaped excitation beam 101 is irradiated so as to cover a plurality of Cu wiring patterns 102 and 103, thermoelastic wave is generated by a thermal distortion wave resulting from a photoacoustic effect or a photothermal effect in the light absorption region 105, and a distribution 110 (indicated by a broken line) of minute displacements is produced at the surface of the sample. Further, in this minute displacement distribution 110, mixing of information does not occur, but individual items of internal information (containing an internal crack 107 and a separation 108) about the respective Cu wiring patterns 102, 103 and the polyimide portion 104 are reflected independently in the profile of the distribution. More specifically, if the stripe-shaped excitation beam 101 is used, a plurality of objects under inspection having distinct thermal contrast can be excited simultaneously and can be detected independently, so that two-dimensional internal information about a sample can be detected with high speed. Referring to FIGS. 5A to 13B, description will next be made of the structure and the function of the heterodyne Twyman-Green interferometric optical system 202 for detecting a distribution 110 (broken line) of minute displacements of the sample surface caused by the photoacoustic effect. In FIG. 5A, the polarization direction of a linearly polarized beam 52 emitted from a He—Ne laser 51 (wavelength 633 nm) is set at 45° C. relative to the x-axis and the y-axis as indicated by 111 in FIG. 10A. The direction perpendicular to paper, as shown in FIG. 5A, is designated as the y-axis, and the direction at right angles with the y-axis is designated as the x-axis. As for the function of a polarization beam splitter 53. out of the incident light beam 52. a p-polarized light component 54 indicated by 112 in FIG. 10A passes through the polarization beam splitter 53. and enters an acousto-optical modulator 62. while an s-polarized light component 55 indicated by 113 in FIG. 10A is reflected by the polarization beam splitter 53. A sine wave with a frequency of $f_{C1}$ equal to the one shown in FIG. 6A is input to the acousto-optical modulator 62 from an oscillator 91. and a first-order diffracted light 64 of the p-polarized light shifted in frequency by $f_{C1}$. A zero-order light 63 is intercepted by diaphragm 65. This first-order diffracted light 64 of the p-polarized light is reflected by a mirror 66. and then passes through a polarization beam splitter 61.

Figures 11A, 11B:
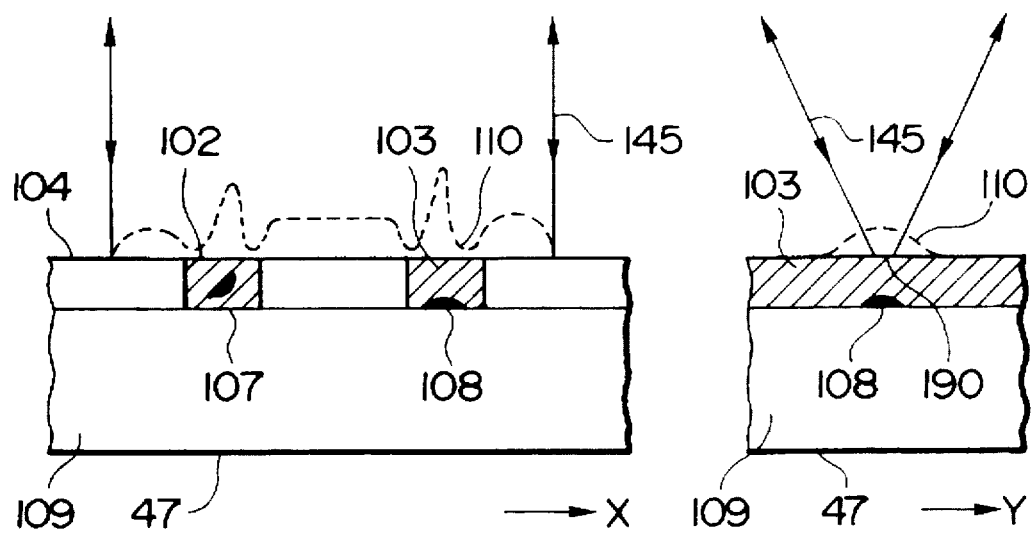
FIGS. 11A and 11B are diagrams showing the incident state on the sample surface of a probe beam in a stripe form in the first embodiment.

On the other hand, the s-polarized light component 55 reflected by the polarization beam splitter 53 is reflected again by the mirror 56. and is incident on an acousto-optical modulator 57. A sine wave with a frequency of $f_{C2}$ ($f_{C1} \neq f_{C2}$) equal to the one shown in FIG. 6A is input to the acousto-optical modulator 57 from the oscillator 91. and a first-order diffracted light 59 of the s-polarized light shifted in frequency by $f_{C2}$ is obtained. A zero-order light 58 is intercepted by a diaphragm 60. The first-order diffracted light 59 of the s-polarized light is reflected by the polarization beam splitter 61. and is combined with the first-order diffracted light 64 of the p-polarized light transmitted through the polarization beam splitter 61. The thus produced combined light 67 has two-frequency orthogonal-polarized components. that is, two polarized beams intersecting at right angles and having a frequency difference of $f_{C1}-f_{C2}$. After passing through a beam splitter 68. the combined light 69 is expanded to a desired beam diameter by a beam expander 70. and made into an elliptic beam as it passes through a cylindrical lens 71. This elliptic beam is separated by a polarization beam splitter 73 into a p-polarized beam 72 and an s-polarized beam 74. The p-polarized beam 72, which has been shifted in frequency by $f_{C1}$. passes through the dichroic prism 41. and is focused only in the x-direction at the pupil 43. that is, the rear focal point 44 of the objective lens 42. On the other hand, with regard to the y-direction. since the cylindrical lens 71 is regarded as a plate glass without a curvature. the p-polarized beam 72 is incident on the rear focal point 44 of the objective lens 42 as a parallel light. The beam leaving the objective lens 42 as it passes through a λ/4 plate 45 becomes a circularly polarized beam 145. and as shown in FIG. 8. at the front focal point of the objective lens. i.e.. on the surface of the sample 47. at the same incident position as the excitation beam 101, a stripe beam 190 is obtained as a probe beam having a width in the x-direction and focused in the y-direction. As shown in FIGS. 11A and 11B. the reflected light from the sample 47 contains a information of minute displacement distribution 110 (broken line) as phase distribution. produced at the surface of the sample 47 caused by a photoacoustic effect. In FIG. 5A. the reflected light from the sample 47. after passing through the λ/4 plate 45. becomes an s-polarized beam. and after the beam passes through the objective lens 42. the beam again travels along the same optical path. and is reflected by the polarization beam splitter 73.

Meanwhile. the s-polarized beam 74 separated by the polarization beam splitter 73 has been shifted in frequency by $f_{C2}$ and after passing through the λ/4 plate 75. becomes a circularly polarized light and is incident on a reference mirror 76.

Figure 12:
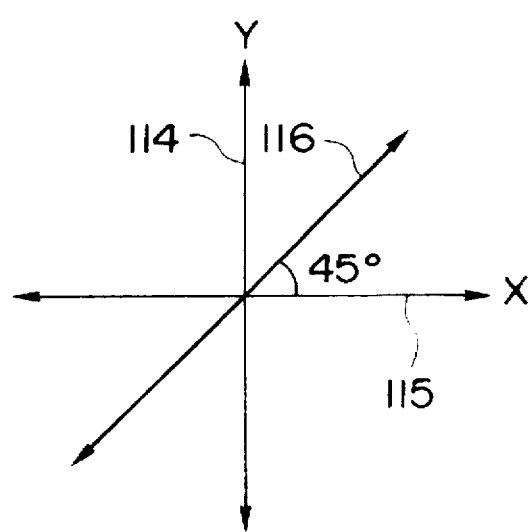
FIG. 12 is a diagram showing the polarization directions of the reflected light from the sample. a reference light and a polarizing plate.

The circularly polarized beam reflected by the reference mirror 76 passes again through the λ/4 plate 75. becomes a p-polarized light, and passes through the polarization beam splitter 73 as a reference light. In FIG. 12. numeral 114 denotes a polarization direction of the light reflected from the sample 47 which has been further reflected by the polarization beam splitter 73. and 115 denotes a polarization direction of the reflected light from the reference mirror 76. These beams of light intersect at right angles. and do not interfere with each other under this condition. So. a polarizing plate 79 is disposed at the rear of an imaging lens 78 to set the polarization direction to 45° as indicated by 116 in FIG. 12. whereby the two reflected beams of light interfere with each other to provide a heterodyne interference light 80 having a beat frequency of $f_B = f_{C1} - f_{C2}$. As light phase distribution information. this heterodyne interference light 80 contains information of one-dimensional distribution in the x-direction of minute displacements produced at the surface of the sample 47 by the photoacoustic effect. After stray light is removed by passing through an interference filter 81 of a central wavelength of 633 nm. the interference light 80 passes through the imaging lens 78 to form an image on a storage type image sensor 82 such as a CCD linear image sensor. Since the surface of the CCD linear image sensor 82 is conjugated with the surface of the sample 47. naturally. a stripe-shaped interference light forms an image on the surface of the sensor. just like the probe beam formed on the surface of the sample 47. The beam splitter 68 causes reflection of about 10% beam out of the complex light 67 having two-frequency orthogonal polarized light components. The two polarized light components of this complex light are caused to interfere with each other by a polarizing plate 83 set at 45° polarization direction. so that a beat signal of $f_B' = f_{C1}' - f_{C2}'$ is detected by a photoelectric converting element 85. such as a photodiode. This beat signal is sent through an amplifier circuit 92 to a CCD linear image sensor driver control circuit 93. The driver control circuit 93 compares a setting beat frequency $f_B$ supplied from a processor 96 and a measured frequency $f_B'$ detected by the photoelectric converting element 85. and adjusts finely the frequency $f_{C1}$ or $f_{C2}$ of the sine wave output from an oscillator 91 through the processor 96 and a modulation signal control circuit 90 so that the above-mentioned compared frequencies match. The oscillator 91 is formed by a PLL (Phase Locked Loop) circuit. for example.

The heterodyne Twyman-Green interferometric optical system 202 will now be described in greater detail with reference to FIGS. 7A. 7B. 13A. and 13B. As shown in FIGS. 7A and 7B. like in the excitation optical system 201. the focal point of the cylindrical lens 71 coincides with the rear focal point 44 of the objective lens 42. and the front focal point of the objective lens coincides with the surface of the sample 47. Therefore. as shown in FIG. 7A. with regard to the x-direction. the p-polarized beam 72 emerging from the cylindrical lens 71 is focused at the rear focal point 44 of the objective lens 42. so that the beam 145 is incident on the surface of the sample 47 as a parallel light.

On the other hand. as shown in FIG. 7B. in the incidence in the y-direction. since the cylindrical lens 71 can be regarded as a plate glass without a curvature. the beam 72 leaving the cylindrical lens 71 is incident on the objective lens 42 as a parallel light. the beam 145 emerging from the objective lens 42 is focused on the surface of the sample 47. As a result. as shown in FIG. 8. on the surface of the sample 47. a stripe beam 190 as a probe beam is obtained having a width in the x-direction and focused in the y-direction like the excitation beam at the same position as the excitation beam 101. Meanwhile. as shown in FIGS. 7A and 7B. the focal position of the cylindrical lens 71 coincides with the position of the reference mirror 76. Consequently. as shown in FIG. 7A, in the incidence in the x-direction, the s-polarized beam 74 leaving the cylindrical lens 71 is focused on the reference mirror 76, and as shown in FIG. 7B, in the incidence in the y-direction, the s-polarized beam 74 is incident on the reference mirror 76 as a parallel light.

Figure 13A:
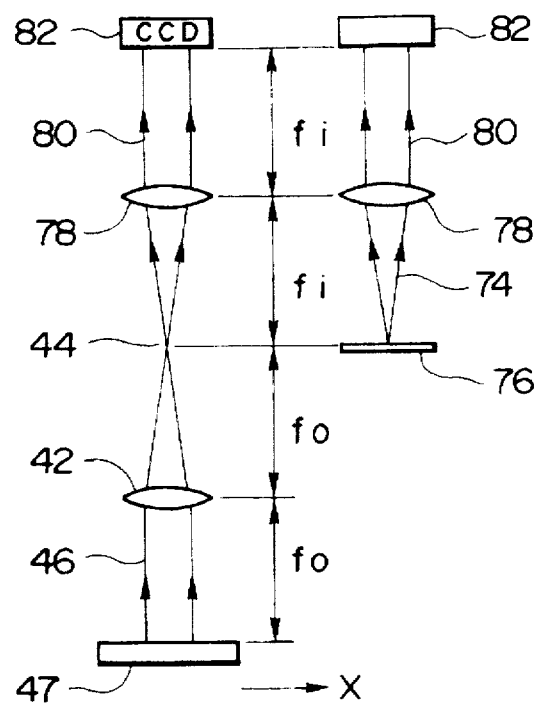
FIGS. 13A and 13B are structural diagrams of the detection unit of the heterodyne interferometric optical system in the first embodiment.
Figure 13B:
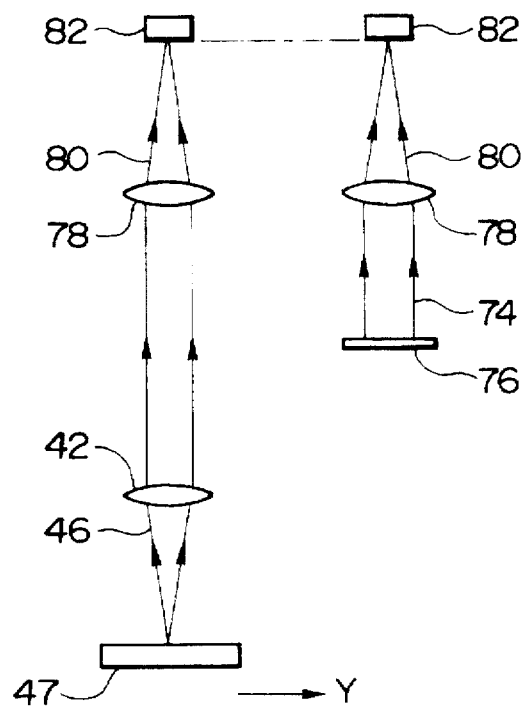
Figure 14:
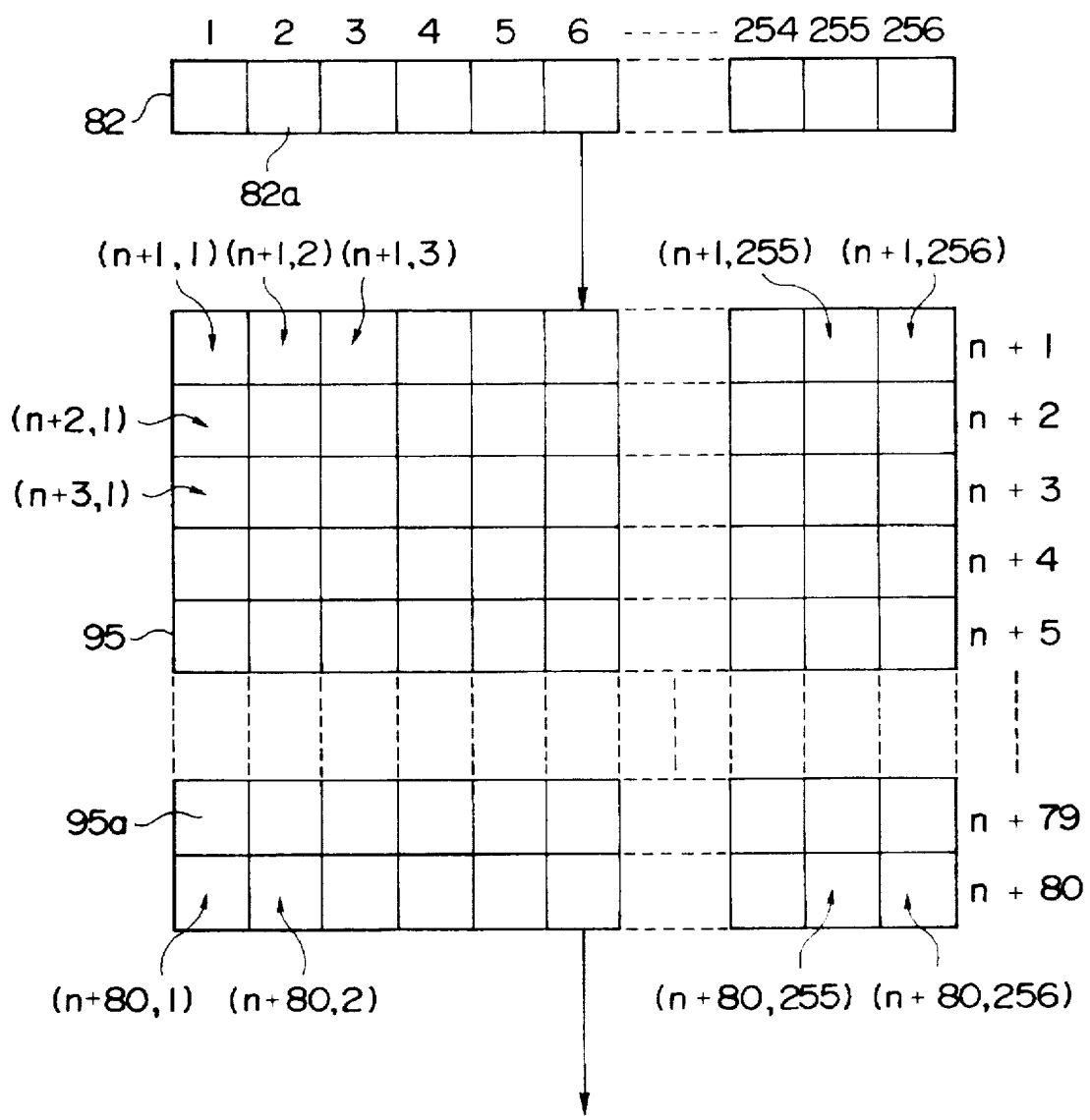
FIG. 14 is a diagram showing data structure in a two-dimensional memory.

As shown in FIGS. 13A and 13B, the front focal position of the objective lens 42 coincides with the surface of the sample 47, the rear focal position of the objective lens 42 coincides with the front focal position of the image forming lens 78, and the rear focal position of the image forming lens 78 coincides with the image pickup surface of the CCD one-dimensional sensor 82. In other words, this optical system is a bi-telecentric image forming optical system. Therefore, as shown in FIG. 13A, with regard to the x-direction, the parallel reflected light from the surface of the sample 47 passes through the objective lens 42, and is then focused at its rear focal position, and after passing through the image forming lens 78, becomes a parallel light again, and is incident on the CCD one-dimensional sensor 82. On the other hand, as shown in FIG. 13B, with regard to the y-direction, the divergent reflected light from the surface of the sample 47 as it passes through the objective lens becomes a parallel light, and after passing through the image forming lens 78, is focused at its rear focal position, that is, on the CCD one-dimensional sensor 82. As a result, on the CCD one-dimensional sensor 82, a stripe beam having a width in the x-direction and focused in the y-direction like the probe beam 190 on the sample 47 is obtained. On the other hand, as shown in FIGS. 13A and 13B, the position of the reference mirror 76 coincides with the front focal position of the image forming lens 78.

Therefore, as shown in FIG. 13A, with regard to the x-direction, after passing through the image forming lens 78, the divergent reflected light from the reference mirror 76 becomes a parallel light, is incident on the CCD one-dimensional sensor 82. As shown in FIG. 13B, with regard to the y-direction, after passing through the image forming lens 78, the divergent reflected light is focused at its rear focal position, that is, on the CCD one-dimensional sensor 82. Consequently, a heterodyne interference light, produced from the reflected light from the sample 47 and the reference light from the reference mirror 76, becomes a stripe beam like the probe beam 72, and is incident on CCD one-dimensional sensor 82, that is, a one-dimensional light interference signal in the x-direction is detected.

Description will be made of a method, using the signal processing system 203, for extracting the amplitude and the phase of minute displacements at the surface of the sample 47 caused by the photoacoustic effect from output signals of the CCD one-dimensional sensor 82 without being affected by the reflectance distribution and the undulations distribution on the surface of the sample 47. If the wavelength of the probe beam 72 incident on the surface of the sample 47 is denoted by $\lambda$, the amplituide by 1, the reflection coefficient of the surface of the sample 47 by $a_S$, the reflection coefficient at the reference light path by $a_r$, the light phase difference between the optical path of the probe light and the optical path of the reference light, including changes of phase caused by undulations of the surface of the sample 47 by $\phi$, minute displacements at the surface of the sample 47 caused by the photoacoustic effect by A, and the amount of phase change relative to the intensity modulation signal by $\theta$, then a heterodyne interference light I incident on one pixel of the CCD one-dimensional sensor 82 is expressed by the expression (2).

$$I = a_s^2 + a_r^2 + 2a_s a_r \cos\left\{ 2\pi f_B t - \frac{4\pi}{\lambda} A\cos(2\pi f_L t + \theta) + \phi \right\} \quad (2)$$

Further, from $A \ll \alpha$, the above expression can be approximately transformed into the following expression (3).

$$I = a_s^2 + a_r^2 + 2a_s a_r \{\cos(2\pi f_B + \phi) + \quad (3)$$
$$\frac{4\pi}{\lambda} A\cos(2\pi f_L t + \theta)\sin(2\pi f_B t + \phi) \}$$

Here, A cos $(2\pi f_L t + \theta)$ is a term expressing a complex amplitude of the minute displacement on the surface of the sample 47 caused by the photoacoustic effect. A detection signal $I_D(n+i)(n+i$ is a number of times of accumulation and output of the CCD one-dimensional sensor 82, where is an arbitrary integer,$>0$) output from one pixel of the CCD one-dimensional sensor 82 is given by the following expression in which the storage time of the sensor is denoted by $\alpha/f_B$.

$$I_D(n+i) = \int_{(n+1-1)\alpha/f_B}^{(n+1)\alpha/f_B} I dt = (a_s^2 + a_r^2)\frac{\alpha}{f_B} + \quad (4)$$

$$2a_s a_r \left[ \frac{1}{\pi f_B} \sin\alpha\pi \cdot \cos\left( 2n\alpha\pi + \left( i - \frac{1}{2} \right) 2\alpha\pi + \phi \right) + \right.$$

$$\frac{2\pi A}{\lambda} \left\{ \frac{1}{\pi(f_B + f_L)} \sin\left( 1 + \frac{f_L}{f_B} \right) \alpha\pi \cdot \right.$$

$$\sin\left( \left( 1 + \frac{f_L}{f_B} \right) 2n\alpha\pi + \phi + \theta + \left( i - \frac{1}{2} \right)\left( 1 + \frac{f_L}{f_B} \right) 2\alpha\pi \right) +$$

$$\frac{1}{\pi(f_B - f_L)} \sin\left( 1 - \frac{f_L}{f_B} \right) \alpha\pi \cdot \sin\left( \left( 1 - \frac{f_L}{f_B} \right) 2n\alpha\pi + \phi - \theta + \right.$$

$$\left. \left. \left( i - \frac{1}{2} \right)\left( 1 - \frac{f_L}{f_B} \right) 2\alpha\pi \right) \right\} \right]$$

Next, for the expression (4), conditions which meet the following items are obtained.

(1) the second term$\neq 0$ (2) the amount of phase shift=$\pi/2$ or $\pi/4$ for the number of times i of accumulation and output in the second term.

(3) the third term$\neq 0$ (4) the amount of phase shift $\pi/2$ for the number of times i of accumulation and output in the third term (5) the fourth term=0

The conditions obtained are as shown by the following expressions (5) and (6) when p and s are integral numbers, and a is a non-integral number.

$$\alpha = \frac{2S + 4P + 1}{8} \quad (5)$$

$$\frac{f_L}{f_B} = \frac{2S - 4P + 1}{2S + 4P + 1} \quad (6)$$

For example, if s=6 and p=2, $\alpha=21/8$, $f_L$=50 kHz, $f_B$=210 kHz can be set, so that the expression (4) can be reduced to the following expression (7).

$$I_D(n+i) = (a_s^2 + a_r^2)\frac{21}{8f_B} \quad : \text{d.c. component} + \tag{7}$$

$$2a_s a_r \left\{ \frac{1}{\pi f_B} \sin\frac{5\pi}{8} \cdot \cos\left(\frac{21}{4}n\pi + \left(i - \frac{1}{2}\right)\frac{21}{4}\pi +\right.\right.$$

$$\left.\phi\right) : \text{modulation component} - \frac{\sqrt{2}A}{\lambda(f_B + f_L)} \cdot \sin\left(\frac{n\pi}{2} + \phi + \theta +\right.$$

$$\left.\left.\left(i - \frac{1}{2}\right)\frac{\pi}{2}\right)\right\}$$

The above-mentioned parameters $\alpha=21/8$, $f_L=50$ kHz, and $f_B=210$ kHz are all set by the processor 96, and those parameters are sent to the CCD one-dimensional sensor driver control circuit 93 and the modulation signal control circuit 90, and according to the values of the parameters, the drive of the CCD linear image sensor and the oscillators 87 and 91 is controlled. For the parameters $\alpha$, $f_L$, and $f_B$, known data related to the heat diffusion lengths at depths to be detected of individual materials is stored previously. A method of setting the sensor storage time $\alpha/f_B$ is as follows. From the above-mentioned setting beat frequency $f_B$ and the parameter a sent from the processor 96, the CCD linear image sensor drive control circuit 93 generates read shift pulses of frequency $f_B/\alpha$ for the CCD linear image sensor, and according to the read shift pulses and clock pulses, the CCD linear image sensor 82 is driven.

In the expression (7), the first term is the d.c. component, the second term is the modulation component related to the light phase difference $\phi$ between the probe light path and the reference light path, including changes of phase due to undulations of the surface of the sample 47, and the phase shift amount relative to the number of times i of accumulation and output is $\pi/4$. The third term is the modulation component related to the light phase difference $\phi$ and the amplitude A and the signal, and the phase shift amount relative to the number of times i of accumulation and output is $\pi/2$. If the signal is to be obtained by using i=1 to i=8 in the expression (7), that is, for one period for the second term and for two periods for the third term, then we have the following expressions (8), (9), (10), (11), (12), (13), (14), and (15).

$$I_D(n+1) = (a_s + a_r)\frac{2\lambda}{8f_B} + 2a_s a_r \left\{ -\frac{1}{\pi f_B} \sin\frac{5\pi}{8} \cdot \right. \tag{8}$$

$$\sin\left(\frac{21}{4}n\pi + \frac{\pi}{8} + \phi\right) - \frac{\sqrt{2}A}{\lambda(f_B+f_L)} \cdot \sin\left(\frac{n\pi}{2} + \phi + \theta + \frac{\pi}{4}\right)\right\}$$

$$I_D(n+2) = (a_s^2 + a_r^2)\frac{21}{8f_B} + 2a_s a_r \left\{ \frac{1}{\pi f_B} \sin\frac{5\pi}{8} \cdot \right. \tag{9}$$

$$\cos\left(\frac{21}{4}n\pi + \frac{\pi}{8} + \phi\right) - \frac{\sqrt{2}A}{\lambda(f_B+f_L)} \cdot \cos\left(\frac{n\pi}{2} + \phi + \theta + \frac{\pi}{4}\right)\right\}$$

$$I_D(n+3) = (a_s^2 + a_r^2)\frac{21}{8f_B} + 2a_s a_r \left\{ -\frac{1}{\pi f_B} \sin\frac{5\pi}{8} \cdot \right. \tag{10}$$

$$\cos\left(\frac{21}{4}n\pi + \frac{\pi}{8} + \phi\right) + \frac{\sqrt{2}A}{\lambda(f_B+f_L)} \cdot \sin\left(\frac{n\pi}{2} + \phi + \theta + \frac{\pi}{4}\right)\right\}$$

$$I_D(n+4) = (a_s^2 + a_r^2)\frac{21}{8f_B} + 2a_s a_r \left\{ -\frac{1}{\pi f_B} \sin\frac{5\pi}{8} \cdot \right. \tag{11}$$

$$\left(-\frac{21}{4}n\pi + \frac{\pi}{8} + \phi\right) + \frac{\sqrt{2}A}{\lambda(f_B+f_L)} \cdot \cos\left(\frac{n\pi}{2} + \phi + \theta + \frac{\pi}{4}\right)\right\}$$

$$I_D(n+5) = (a_s^2 + a_r^2)\frac{21}{8f_B} + 2a_s a_r \left\{ \frac{1}{\pi f_B} \sin\frac{5\pi}{8} \cdot \right. \tag{12}$$

$$\sin\left(\frac{21}{4}n\pi + \frac{\pi}{8} + \phi\right) - \frac{\sqrt{2}A}{\lambda(f_B+f_L)} \cdot \sin\left(\frac{n\pi}{2} + \phi + \theta + \frac{\pi}{4}\right)\right\}$$

$$I_D(n+6) = (a_s^2 + a_r^2)\frac{21}{8f_B} + 2a_s a_r \left\{ -\frac{1}{\pi f_B} \sin\frac{5\pi}{8} \cdot \right. \tag{13}$$

$$\cos\left(\frac{21}{4}n\pi + \frac{\pi}{8} + \phi\right) - \frac{\sqrt{2}A}{\lambda(f_B+f_L)} \cdot \cos\left(\frac{n\pi}{2} + \phi + \theta + \frac{\pi}{4}\right)\right\}$$

$$I_D(n+7) = (a_s^2 + a_r^2)\frac{21}{8f_B} + 2a_s a_r \left\{ \frac{1}{\pi f_B} \sin\frac{5\pi}{8} \cdot \right. \tag{14}$$

$$\cos\left(\frac{21}{4}n\pi + \frac{\pi}{8} + \phi\right) + \frac{\sqrt{2}A}{\lambda(f_B+f_L)} \cdot \sin\left(\frac{n\pi}{2} + \phi + \theta + \frac{\pi}{4}\right)\right\}$$

$$I_D(n+8) = (a_s^2 + a_r^2)\frac{21}{8f_B} + 2a_s a_r \left\{ -\frac{1}{\pi f_B} \sin\frac{5\pi}{8} \cdot \right. \tag{15}$$

$$\cos\left(\frac{21}{4}n\pi + \frac{\pi}{8} + \phi\right) + \frac{\sqrt{2}A}{\lambda(f_B+f_L)} \cdot \cos\left(\frac{n\pi}{2} + \phi + \theta + \frac{\pi}{4}\right)\right\}$$

In practice, after a detection signal $I_D$ (n+i) from the CCD one-dimensional sensor 82 is amplified by an amplifier circuit 94, ten data sets obtained when i=1 to i=8 are used in the expression 7, that is, a total of 80 accumulated and output data sets are stored in a two-dimensional memory 95. If the number of pixels of the CCD one-dimensional sensor 80 is 256, it follows that 256×80 items of data have been stored. If data of the w-th pixel at the (n+i)-th accumulation and output is designated by (n+i, w), the order in which the data is stored in the two-dimensional memory 95 is:

| | | | |
|---|---|---|---|
| (n+1, 1), | (n+1, 2), | (n+1, 3), . . . , | (n+1, 256), |
| (n+2, 1), | (n+2, 2), | (n+2, 3), . . . , | (n+2, 256), |
| (n+3, 1), | (n+3, 2), | (n+3, 3), . . . , | (n+3, 256), |
| . | | | |
| . | | | |
| (n+80, 1), | (n+80, 2), | (n+80, 3), . . . , | (n+80, 256) |

Meanwhile, to from the two-dimensional memory 95, 80 accumulated and output data sets are read one pixel by one pixel, and sent to the processor 96.

| | | | |
|---|---|---|---|
| (n+1, 1), | (n+2, 1), | (n+3, 1), . . . , | (n+80, 1) |
| (n+1, 2), | (n+2, 2), | (n+3, 2), . . . , | (n+80, 2) |
| (n+1, 3), | (n+2, 3), | (n+3, 3), . . . , | (n+80, 3) |
| . | | | |
| . | | | |
| (n+1, 256), | (n+2, 256), | (n+3, 256), . . . , | (n+80, 256) |

Using 80 accumulated and output data sets for each pixel, the processor 96 performs arithmetic operations shown below to obtain the reflectance $a_s^2$ of the surface of the sample 47, the light phase difference ( between the optical path of the probe light and the optical path of the reference light, including changes of phase due to the undulations of the surface of the sample 47, the amplitude of a photoacoustic signal in which the reflectance of the surface of the sample 47 has been corrected, and the phase $\theta$ of the photoacoustic signal in which changes of phase due to the undulations of the surface of the sample 47.

By calculating a sum of the expressions 8 to 15, the reflectance $a_s^2$ of the surface of the sample 47 is given by the following expression (16).

$$a_s^2 = \frac{f_B}{21} \sum_{i=1}^{8} I_D(n+i) - a_r^2 \quad (16)$$

The light phase difference φ between the probe light path and the reference light path, including changes of phase due to the undulations of the surface of the sample 47, is given by the following expression (17), derived from the expressions (8), (10), (12), and (14).

$$\phi = \tan^{-1} \frac{I_D(n+1) - I_D(n+5)}{I_D(n+3) - I_D(n+7)} - \frac{n\pi}{4} - \frac{\pi}{8} \quad (17)$$

The amplitude of the photoacoustic signal, that is, minute displacement A thereof on the surface of the sample 47 is given by the expression (18), in which the reflectance of the surface of the sample 47 has been corrected, derived from the expressions (8), (9), (12), (13) and (16).

$$A = \frac{\lambda(f_B + f_L)}{2\sqrt{2a_r a_s}} \sqrt{\left\{ -\frac{I_D(n+1) + I_D(n+5)}{2} + \frac{1}{8} \sum_{i=1}^{8} I_D(n+i) \right\}^2 + \left\{ -\frac{I_D(n+2) + I_D(n+6)}{2} + \frac{1}{8} \sum_{i=1}^{8} I_D(n+i) \right\}^2} \quad (18)$$

The phase of the photoacoustic signal, that is, the phase change φ thereof relative to the intensity-modulated signal of the excitation light is given by the following expression (19), in which the changes of phase due to the undulations of the surface of the sample 47 have been corrected, derived from the expressions (8), (9), (12), (13), (16) and (17).

$$\theta = \tan^{-1} \frac{-\left\{ I_D(n+1) + I_D(n+5) + \frac{1}{4} \sum_{i=1}^{8} I_D(n+i) \right\}}{-\{I_D(n+2) + I_D(n+6)\} + \frac{1}{4} \sum_{i=1}^{8} I_D(n+i)} - \tan^{-1} \frac{I_D(n+1) - I_D(n+5)}{I_D(n+3) - I_D(n+7)} + \frac{3n\pi}{4} - \frac{\pi}{8} \quad (19)$$

FIG. 5B shows a structural example of the processor 96. The processor 96 has the signal processor 96a which exchanges signals with the CCD one-dimensional sensor driver control circuit 93, the memory 95, an X-Y TABLE 48 and the modulation signal control circuit 90, and which sets data and parameters. The processor 96 includes a surface reflectance arithmetic unit 96a for calculating the reflectance of the sample surface corresponding to the pixels of CCD 82 by the expression (16) shown above, a surface undulations arithmetic unit 96c by the expression (17), a photoacoustic amplitude arithmetic unit 96d by the expression (18), and a photoacoustic phase arithmetic unit 96e by the expression (19). The processor 96 also includes a display selector 96f for receiving calculation results of the four arithmetic units, selecting one of the calculation results in response to a selection signal which is set externally, and displaying that calculation result on the display 97.

Figure 15A:
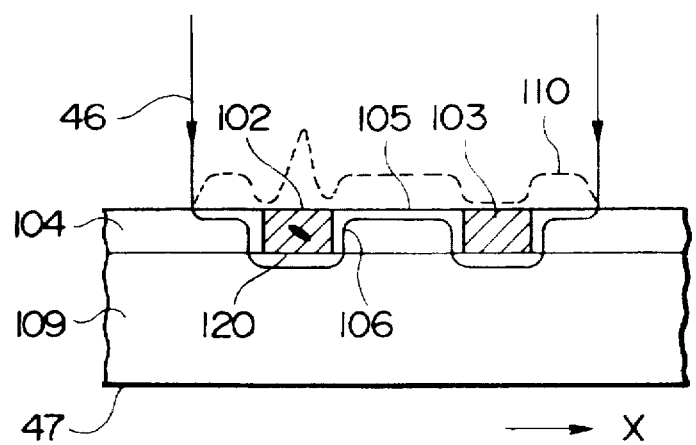
FIGS. 15A, 15B, and 15C are diagrams showing example of detection of a photoacoustic signal in the first embodiment.
Figure 15B:
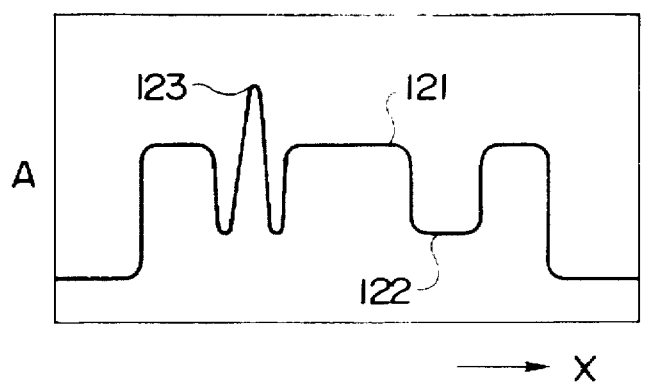
Figure 15C:
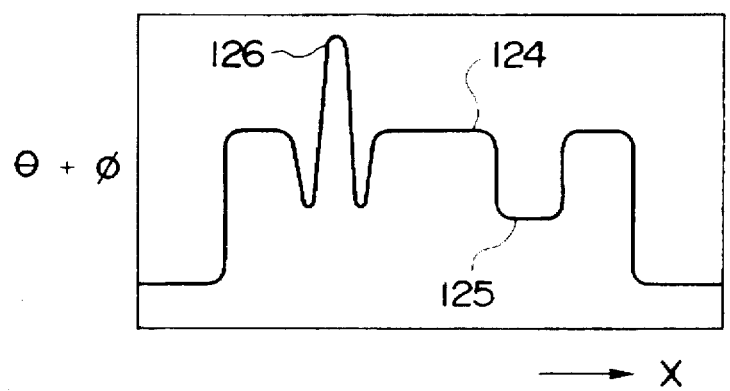

FIGS. 15A, 15B and 15C show an example of a photoacoustic signal detected in this embodiment. From FIG. 15A, it will be understood that a minute displacement 110 (broken line) on the surface of the Cu wiring pattern 102 caused by an internal crack 120 is greater than that of the surface of the normal Cu wiring pattern 102. Similarly, in a distribution 121 of the amplitude A of the photoacoustic signal in FIG. 15B and in a distribution 124 of the phase θ+φ of the photoacoustic signal before correction of the changes of phase due to the undulations of the surface of the sample 47 in FIG. 15C, there are sharp signals 123 (FIG. 15B) and 126 (FIG. 15C) by the internal cracks.

Figure 16A:
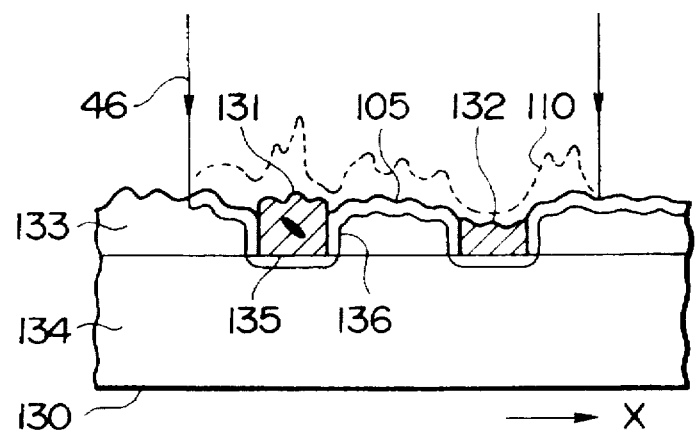
FIGS. 16A, 16B, and 16C are diagrams of example of a photoacoustic signal showing the effects of phase correction in the first embodiment.
Figure 16B:
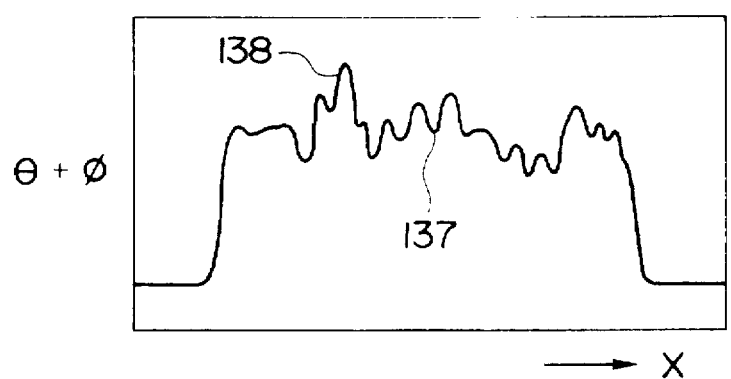
Figure 16C:
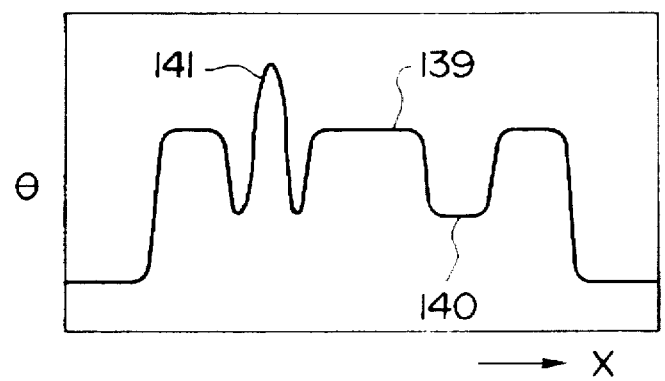

On the other hand, FIGS. 16A, 16B and 16C show an example of a photoacoustic signal detected in this embodiment in a case where there are undulations distributed on the surface of a sample 47. As shown in FIG. 16B, a distribution 137 of a phase θ+φ of a photoacoustic signal before phase correction is affected by changes of phase due to undulations of the surface of the sample 47, so that the signal-to-noise ratio of the signal decreases greatly, and as a result, it is difficult to recognize an internal crack 135. However, as shown in FIG. 16C, in a distribution of the phase signal in which phase correction has been done by the expression 19, the distribution 139 of the phase signal θ is not affected by changes of phase and a signal 141 due to the internal crack 135 can be recognized clearly.

By processing the detection signal from the above-mentioned CCD one-dimensional sensor by the processor 96 while scanning the sample 47 sequentially in the x- and y-directions by using the X-Y stage 48, a two-dimensional photoacoustic image of the whole surface of the sample 47 can be obtained and displayed on a TV monitor.

As has been described, according to the present embodiment, in contrast to the conventional point-scanning method in which information is detected one point after another, a plurality of points being measured are excited simultaneously using an excitation beam in a stripe form, light interference is used in detecting a photoacoustic signal from the respective points being measured so that an interference light is detected as parallel-output data obtained simultaneously. Thus, the photoacoustic signal at a plurality of points being measured of the sample can be detected in parallel simultaneously, so that two-dimensional information on the sample can be detected at high speed.

Further, according to the present embodiment, by a single CCD one-dimensional sensor, it is possible to simultaneously detect four items of information relative to the surface and the inside of the sample, including the reflectance distribution of the sample surface, the undulations distribution of the sample surface, the amplitude distribution of the photoacoustic signal, and the phase distribution of the photoacoustic signal, with the result that a compound assessment of a sample becomes possible.

Further, according to the present embodiment, it is possible to detect the reflectance distribution of the sample surface, the undulations distribution of the sample surface, and a photoacoustic signal for which the sway of the optical path has been corrected, and thus, it is possible to detect information relative to the surface and the inside of the sample with stability and high sensitivity.

Further, according to the present embodiment, by setting the intensity-modulated frequency of the excitation beam so that the heat diffusion length due to the photoacoustic effect is equal to or longer than the depth of the interface between the Cu wiring pattern under inspection and the ceramic substrate, inspection of the interface becomes possible.

Further, according to the present invention, when extracting a photoacoustic signal from the light interference signal, a digital frequency filtering process is used instead of the analog process, a photoacoustic signal can be detected with high sensitivity and accuracy without being not much affected by higher harmonic components.

Figure 17:
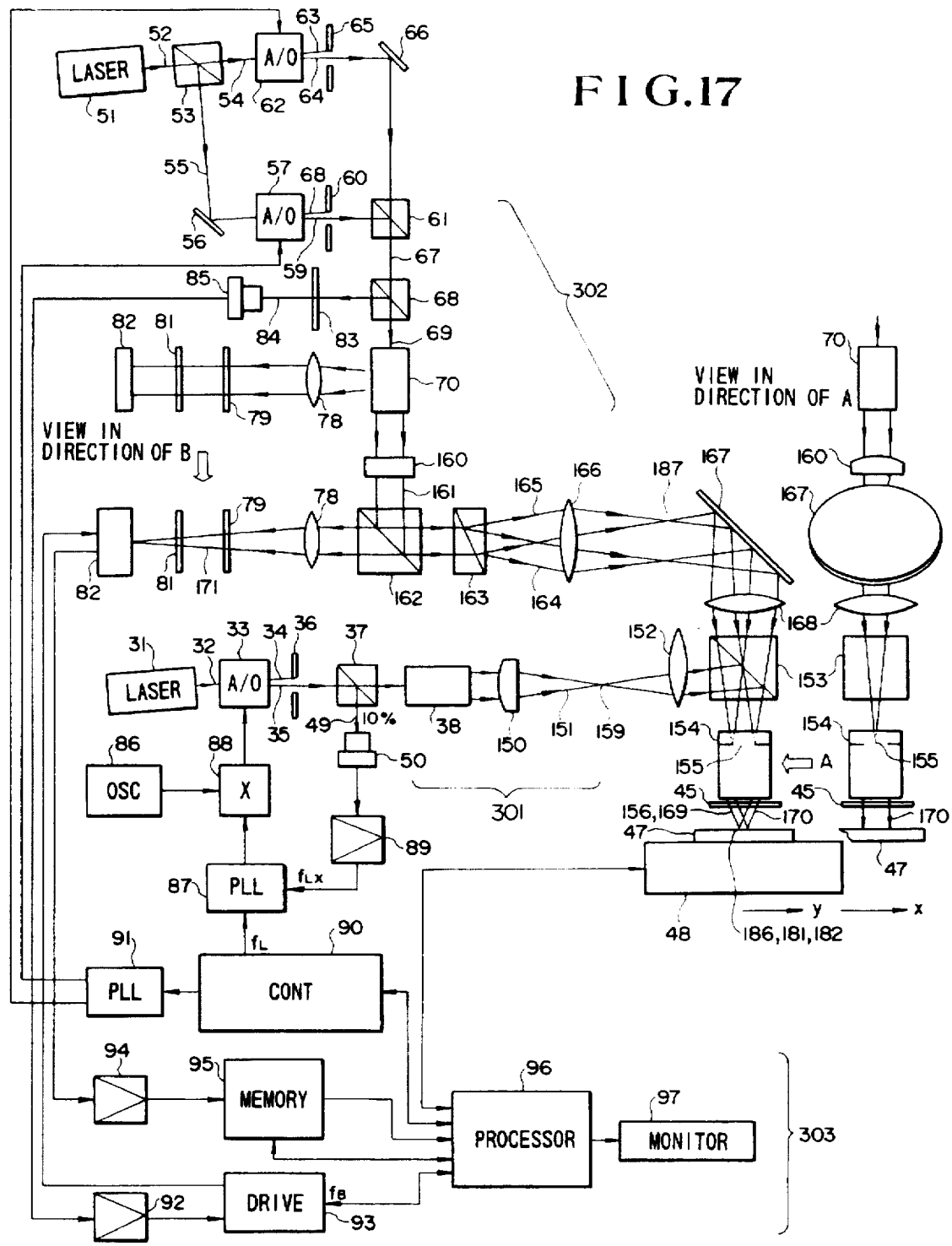
FIG. 17 is a diagram of the photoacoustic detection optical system in a second embodiment of the present invention.

In the present embodiment, examples have been described in which the present invention can be applied to samples having a plurality of objects under inspection which exhibit a sharp thermal contrast, but the present invention can be applied sufficiently to samples made of a homogeneous material and containing an internal crack. Also in this case, since a plurality of points being measured on a sample can be excited, the above-mentioned effects can be expected. next, a second embodiment of the present invention will be described with reference to FIGS. 17 to 25. FIG. 17 shows a photoacoustic detection optical system according to the second embodiment. This optical system comprises an excitation optical system 301, a heterodyne differential interferometric optical system 302 for detecting a photoacoustic signal, and a signal processing system 303. In an excitation optical system 301, the structure and the function of the part for obtaining an intensity-modulated beam 35 of the modulation frequency f L are the same are in the first embodiment, their description will be omitted. After passed through a beam splitter 37, the intensity-modulated is expanded to a desired beam diameter by a beam expander 38, and is focused by a cylindrical lens 150 at its focal position only in the y-direction. This focal position 159 coincides with the front focal position of an off-axis relay lens 152. The beam having passed the relay lens 152 again becomes a parallel light, which is reflected by a dichroic prism 153 (reflects wavelengths 600 nm or less, transmits wavelengths more than 600 nm), and then is incident on the pupil of an objective lens 154, that is, the rear focal position 155. On the other hand, with regard to the x-direction, since the cylindrical lens 150 can be regarded as a plate glass without a curvature, the beam incident as a parallel light on the relay lens 152, is focused at the rear focal position 155 of the objective lens 154, which coincides with the rear focal position of the relay lens 152. As a result, the front focal position of the objective lens 154, that is, on the surface of the sample 47, a stripe beam 186 having a width in the x-direction and focused in the y-direction can be obtained as the excitation beam.

The beam splitter 37 reflects a beam 49 corresponds to about 10% of the intensity-modulated beam 35 as in the first embodiment, and after detected by a photoelectric converting element 50 such as a photodiode, the beam 49 is sent to an oscillator 89 through an amplifier circuit 89. The oscillator 87 compares a set frequency $f_L$ sent from a modulation signal control circuit 90 and a measured frequency $f_L$ detected by the photoelectric converging element 50, and finely adjusts the oscillation frequency so that the compared frequencies match. The oscillator 87 is formed by a PLL (Phase Locked Loop) circuit, for example.

Figure 18A:
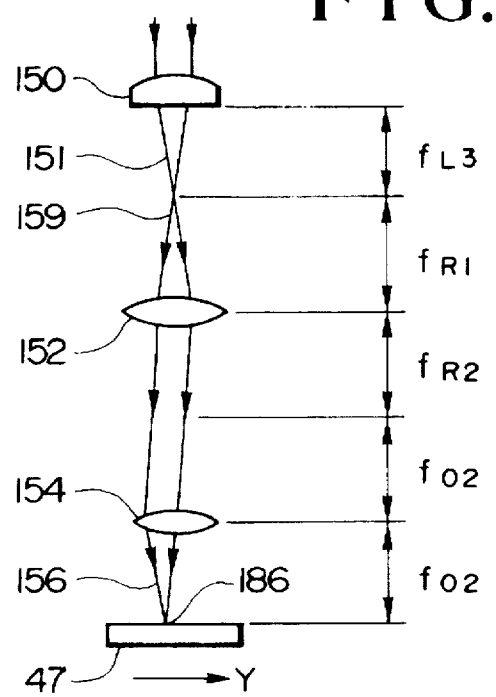
FIGS. 18A and 18B are diagrams showing structural examples of the excitation optical system in the second embodiment.
Figure 18B:
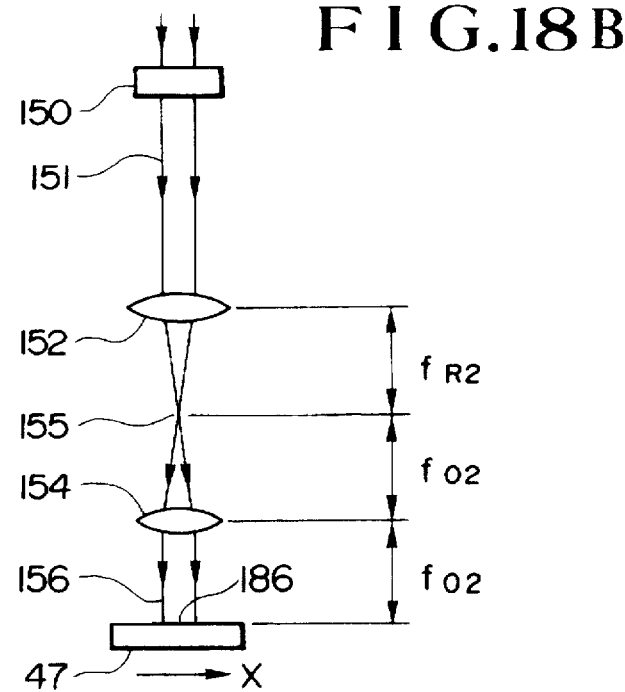

The excitation optical system will be described in greater detail with reference to FIGS. 18A and 18B. In FIGS. 18A and 18B, the focal position 159 of the cylindrical lens 150 coincides with the front focal position of the off-axis relay lens 152, the rear focal position of the relay lens 152 coincides with the rear focal position 155 of the objective lens 154, and the front focal position of the objective lens 154 coincides with the surface of the sample 47. Therefore, as shown in FIG. 18A, with regard to the y-direction, since a beam 151 emerging from the cylindrical lens 150 is focused at its focal position 159, that is, the front focal position of the relay lens 152, the beam having passed the relay lens 152 again becomes a parallel light which is incident on the objective lens 154, and the beam 156 leaving the objective lens 154 is focused on the surface of the sample 47. Further, since the relay lens is off its axis, the focal position of the relay lens is off the center of the objective lens 154. On the other hand, as shown in FIG. 18B, since the cylindrical lens 150 can be regarded as a plate glass without a curvature, the beam 151 leaving the cylindrical lens 150 as a parallel lens is incident on the relay lens 152, and is focused at the rear focal position 155 of the objective lens 154, which rear focal position 155 coincides with the rear focal position of the relay lens 152. As a result, a beam 156 leaving the objective lens 154 becomes a parallel light and is incident on the surface of the sample 47. Inconsequence, on the surface of the sample 47, a stripe beam 186 having a width in the y-direction and focused in the y-direction can be obtained as an excitation beam.

Figures 20A, 20B:
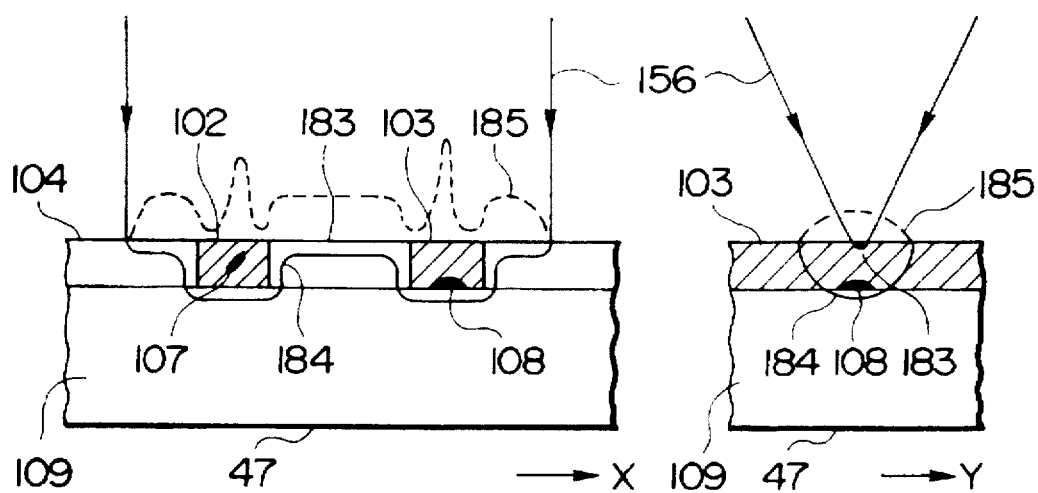
FIGS. 20A and 20B are diagrams showing cross-sectional structures of the sample and generated states of a photoacoustic effect by an excitation beam in a stripe form in the second embodiment.

FIGS. 20A and 20B show a distribution 185 (broken line) of minute displacements at the sample surface caused by a photoacoustic effect produced along a light absorption region 183 by irradiating the above-mentioned excitation beam 186 in a stripe form to the sample including Cu wiring patterns 102 and 103 formed using an organic polymeric material 104 such as polyimide as an insulator in the same manner as in the first embodiment. Like in the first embodiment, internal information (internal crack 107, separation 108) on the Cu wiring patterns 102 and 103 and internal information on the polyimide portion 104 are independently reflected, without being mixed, in the distribution 185 of the minute displacements. In other words, by using this stripe-shaped excitation beam 186, a plurality of objects under inspection which exhibit a sharp thermal contrast can be excited simultaneously, so that two-dimensional internal information about the sample can be obtained with high speed.

Figure 10B:
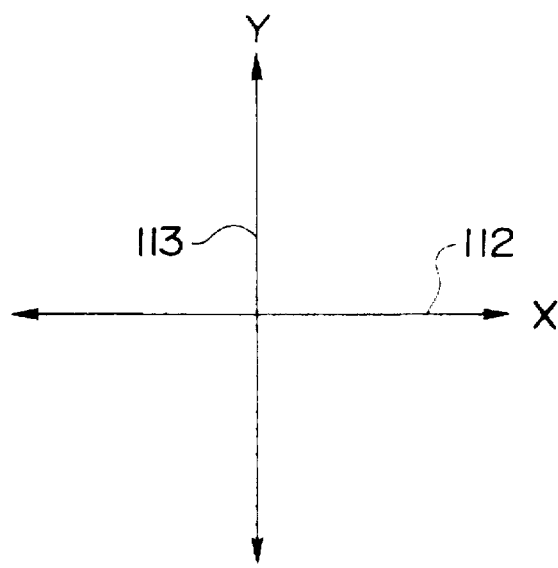

The structure and the function of the heterodyne differential interferometric optical system 302 for detecting the distribution 185 (broken line) of minute displacements at the sample surface caused by a photoacoustic effect will be described with reference to FIGS. 17, 21A, 21B, and 25. In the heterodyne differential interferometric optical system 302 in FIG. 17, the structure and the function of the part for obtaining two-frequency orthogonal polarized beams, that is, the complex light 67 having light components intersecting at right angles in directions 112 and 113 as shown in FIG. 10B and having a frequency difference of $f_{C1} - f_{C2}$ between them is exactly the same as in the first embodiment, and their description is omitted. Here, the direction perpendicular to paper as shown in FIG. 17 is designated as the x-axis and the direction intersecting at right angles to the x-axis is designated as the y-axis. After the complex light 67 of the two-frequency orthogonal polarized beams is passed through the beam splitter 68, the light is expanded to a desired beam diameter by the beam expander 70, and then, made into an elliptic beam by a cylindrical lens 160. With regard to the y-direction, since the cylindrical lens 160 can be regarded as a plate glass without a curvature, this elliptic beam, which is a parallel light in relation to the y-direction, is reflected as a parallel light by the beam splitter 162, and is separated into a p-polarized beam 164 and an s-polarized beam 165, both parallel beams, by a Wollaston prism 163 (or Rochon prism) placed at the focal position of the cylindrical lens 160. Because the position of the Wollaston prism 163 coincides with the front focal position of the relay lens 166, the principal rays of these two beams having passed through the relay lens 166 become parallel to each other, and the respective beams are focused at the rear focal position 187 of the relay lens 166.

Figure 19:
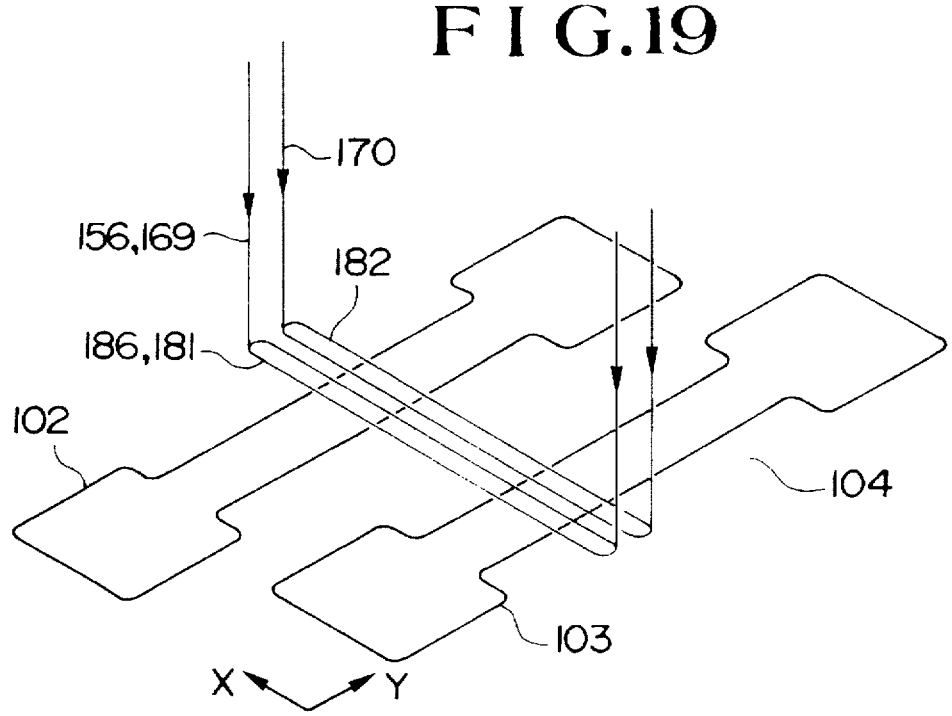
FIG. 19 is a perspective view a planar structure of a sample, an excitation beam, a probe beam, and a reference beam in the second embodiment.
Figure 21A:
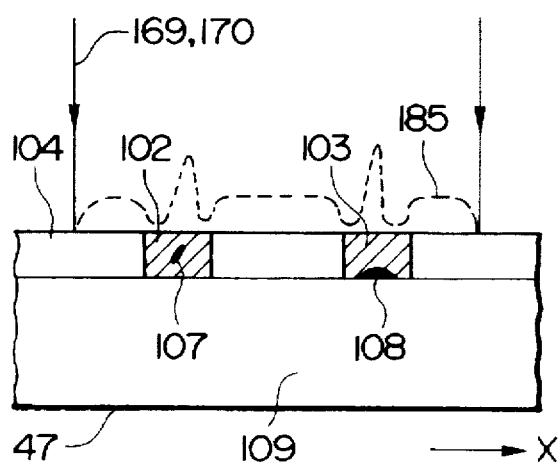
FIGS. 21A and 21B are diagrams showing incident states on the sample surface of a probe beam and a reference beam both in a stripe form in the second embodiment.
Figure 21B:
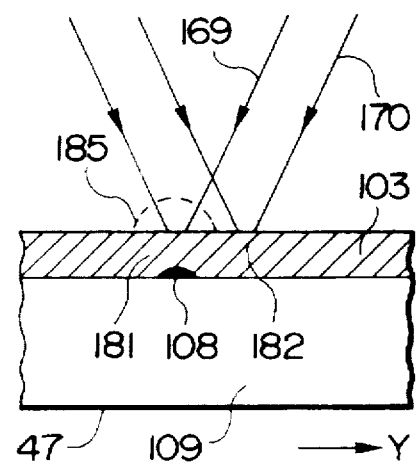

Since the rear focal position 187 of the relay lens 166 coincides with the front focal position of the relay lens 168, the principal rays of the two beams, after passing through the relay lens 168, travel through the dichroic prism 153, and are focused at the rear focal position 155 of the objective lens 154, which rear focal position 155 coincides with the rear focal position of the relay lens 168. At the same time, the two beams are incident as parallel beams on the rear focal position 155 of the objective lens 154. On the other hand, with regard to the x-direction, the beam emerging from the cylindrical lens 160 is focused on the Wollaston prism 163, and then the beam travel through the relay lens 166 and becomes a parallel beam, and after passing through the dichroic prism 153, the parallel beam is focused at the rear focal position of the objective lens 154. As a result, at the front focal position of the objective lens 154, that is, on the surface of the sample 47, a stripe beam 186 having a width in the x-direction and focused in the y-direction as an excitation beam. Two beams emerging from the objective lens 154 after passing through a λ/4 plate, become circularly polarized beams 169 and 170. Thus, as shown in FIG. 19, at the front focal position of the objective lens, that is, on the surface of the sample 47, a stripe beam 181 having a width in the x-direction and focused in the y-direction like the excitation beam 186 can be obtained as a probe beam at the same position as the excitation beam 186, and also, at a position a little away from the probe beam 181, a stripe beam 182 having a width in the x-direction and focused in the y-direction like the probe beam can be obtained as a reference beam. As shown in FIGS. 21A and 21B, a reflected light from the position of the probe beam 181 of the sample 47 has a phase distribution information the distribution 185 (broken line) of minute displacements produced on the surface of the sample 47 by the photoacoustic effect. Meanwhile, the reference beam 182 is so arranged to be incident at a position as close to the probe beam 181 as possible as shown in FIGS. 21A and 21B in a range where minute displacements 185 are produced on the surface of the sample 47 by the excitation beam 186, namely, outside the heat diffusion region 184 in FIGS. 20A and 20B. Reflected beams of light from the positions of the probe beam 181 and the reference beam 182 on the sample 47 pass through the λ/4 plate and become an s-polarized beam and a p-polarized beam, and those polarized beams, after passing through the objective lens 42, travel again along the same optical paths, and after combined by the Wollaston prism 163, pass through the beam splitter 162.

Reference numeral 114 in FIG. 12 denotes the polarization direction of the reflected light from the position of the probe beam 181, while 115 denotes the polarization direction of the reflected light from the position of the reference beam 182. Since the two reflected beams of light intersect at right angles to each other, they do not interfere with each other under this condition. So, by inserting a polarizing plate 79 after the image forming lens 78 so as to set the polarizing direction to 45° as indicated by 166 in FIG. 12, the reflected beams are caused to interfere with each other to provide a heterodyne interference light 171 having a beat frequency of $f_B = f_{C1} - f_{C2}$. This heterodyne interference light 171 contains as light phase distribution information a one-dimensional x-direction distribution of minute displacements produced on the surface of the sample 47 by the photoacoustic effect. This interference light 171 is passed through an interference filter 81 of a central wavelength of 633 nm to eliminate stray light, and then the interference light 171 travels through the image forming lens 78 and forms an image on the storage type solid image pickup element 82, such as a CCD one-dimensional sensor, for example. Since the image pickup surface of the CCD one-dimensional sensor 82 is in image forming relationship with the surface of the sample 47, naturally, the interference light in a stripe shape forms an image on the image pickup surface like the probe beam formed in a stripe on the surface of the sample 47. Meanwhile, the beam splitter 68 reflects a beam corresponding to about 10% of the complex light 67 of two-dimensional orthogonal polarized beams just like in the first embodiment. The two polarized components of this beam are caused to interfere with each other by a polarizing plate 83 with its polarization direction set at 45° direction as indicated by 116 in FIG. 12, so that a beat signal of $f_B' = f_{C1}' - f_{C2}'$ is detected by the photoelectric converting element 85 such as a photodidoe. This beat signal is sent through the amplifier circuit 92 to the CCD one-dimensional sensor driver circuit 93. The driver control circuit 93 compares the setting beat frequency $f_B$ sent from the processor 96 and the measured frequency $f_B'$ detected by the photoelectric converting element 85, and finely adjusts the frequency $f_{C1}$ or $f_{C2}$ of the sine wave from the oscillator 91 through the processor 96 and the modulation signal control circuit 90 so that those two frequencies match. The oscillator 91 is formed by a PLL (Phase Locked Loop) circuit, for example.

Figure 22:
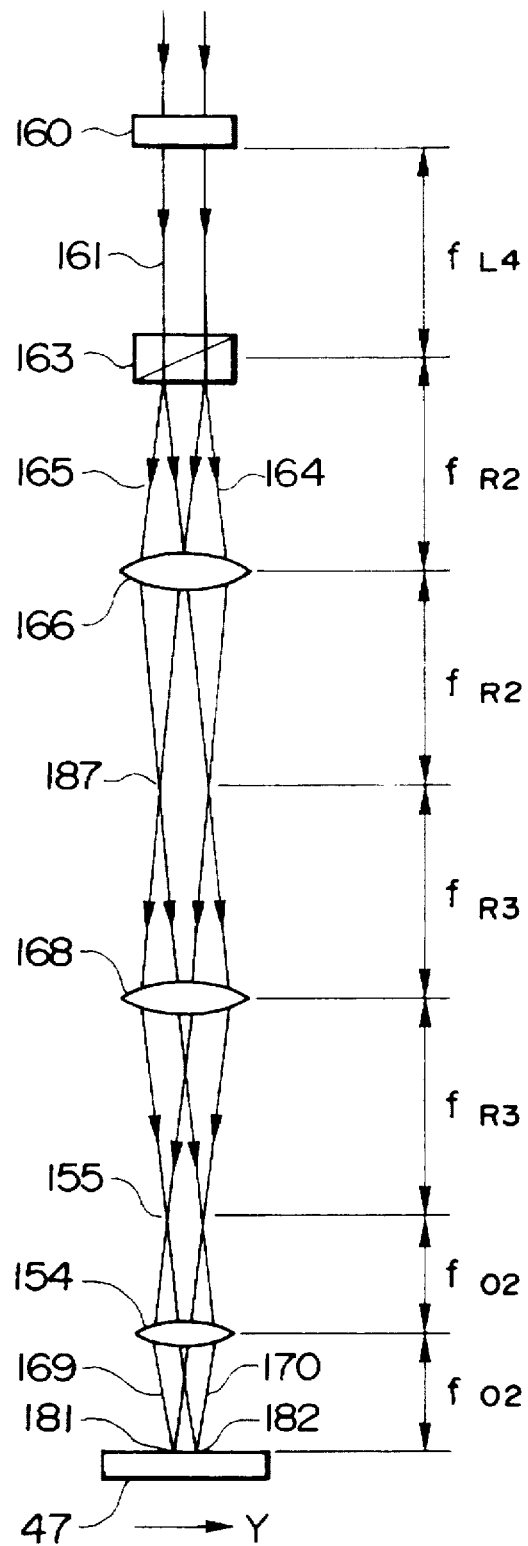
FIG. 22 is a structural diagram of the heterodyne interferometric optical system in the second embodiment as seen from the X-axis direction.
Figure 23:
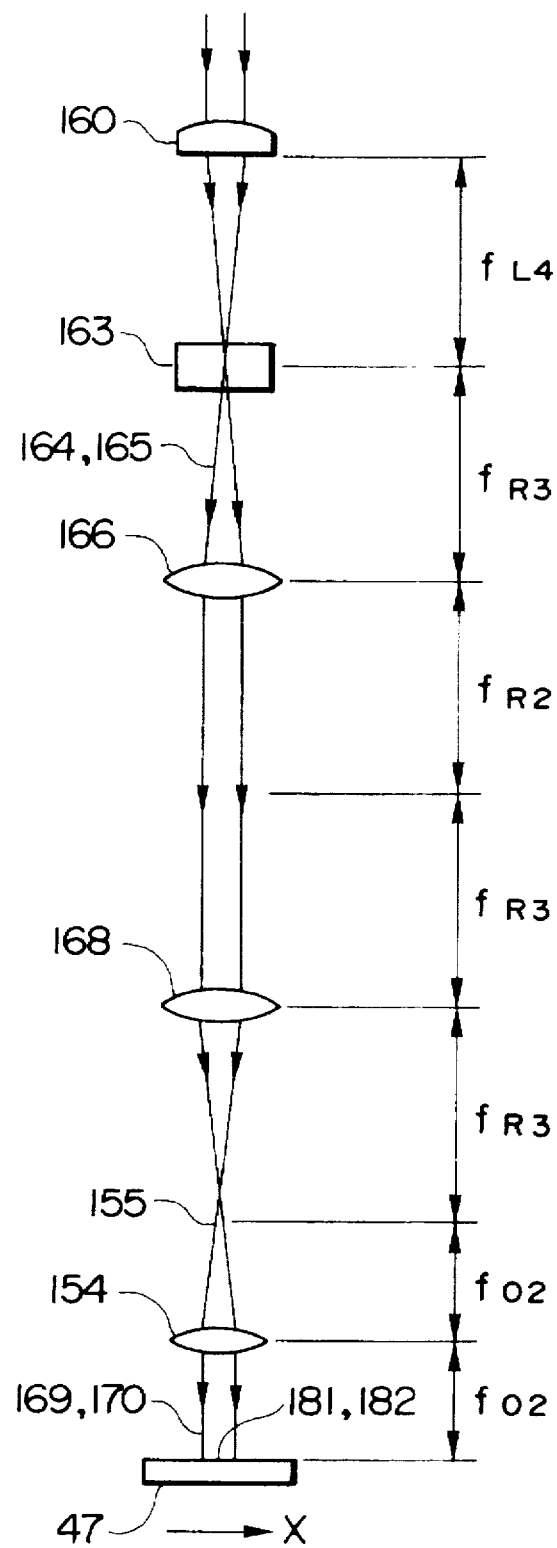
FIG. 23 is a structural diagram as seen from the Y-axis direction in FIG. 22.

The heterodyne differential interferometric optical system 302 will be described in greater detail with reference to FIGS. 22, 23, 24, and 25. As shown in FIGS. 22 and 23, the focal position of the cylindrical lens 160 coincides with the position of the Wollaston prism 163, the position of the Wollaston prism 163 coincides with the front focal position of the relay lens 166, the rear focal position 187 of the relay lens 166 coincides with the front focal position of the relay lens 168, the rear focal position of the relay lens 168 coincides with the rear focal position 155 of the objective lens 154, and the front focal position of the objective lens 154 coincides with the surface of the sample 47. Therefore, as shown in FIG. 22, with regard to the y-direction, since the cylindrical lens 160 can be regarded as a plate glass without a curvature, a complex light 161 of two-frequency orthogonal polarized components leaving the cylindrical lens 160 is incident as a parallel light on a Wollaston prism 163, and subsequently separated into a p-polarized beam 164 and an s-polarized beam 165. Because the position of the Wollaston prism 163 coincides with the front focal position of the relay lens 166, the principal rays of the two beams, after passing through the relay lens 166, become parallel to each other, and the respective beams are focused at the rear focal position 187 of the relay lens 166. Since the rear focal position 187 of the relay lens 166 coincides with the front focal position of the relay lens 168, the principal rays of the two beams, after passing through the relay lens 168, are focused at the rear focal position 155 of the objective lens 154, which rear focal position 155 coincides with the rear focal position 155 of the objective lens 154. As the two beams are simultaneously incident as parallel beams at the rear focal position 155 of the objective lens 154, the two beams 169 and 170 emerging from the objective lens 154 are both focused on the surface of the sample 47. The principal rays of the two beams are parallel to each other.

On the other hand, as shown in FIG. 23, with regard to the x-direction, the beam leaving the cylindrical lens 160 is focused at the Wollaston prism 163, and as the beam passes through the relay lens 166, it becomes a parallel light, and is focused at the rear focal position 155 of the objective lens 154 by the relay lens 168. Therefore, the beams 169 and 170 leaving the objective lens 154 both become parallel beams, and are incident on the surface of the sample 47. Consequently, as shown in FIG. 19, a stripe beam 181 having a width in the x-direction and focused in the y-direction like the excitation beam 186 can be obtained as a probe beam at the same position as the excitation beam 186 on the surface of the sample 47, and also, a stripe beam 182 having a width in the x-direction and focused in the y-direction like the probe beam 181 can be obtained as a reference beam at a position a little away from the probe beam 181.

Figure 24:
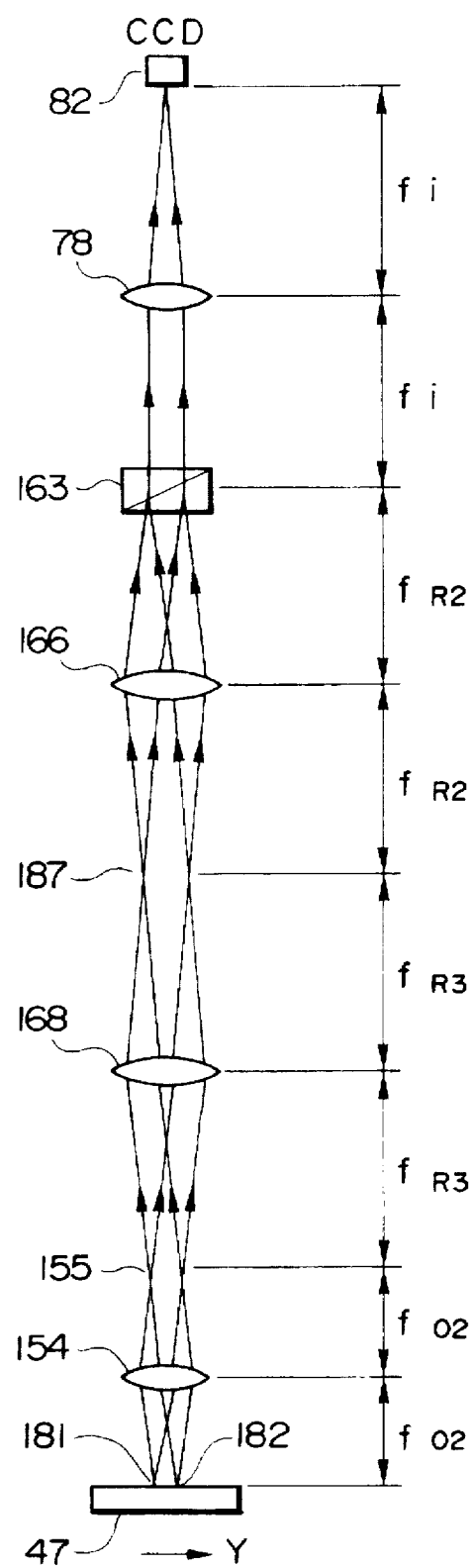
FIG. 24 is a structural diagram of the detection unit of the heterodyne interferometric optical system in the second embodiment as seen from the X-axis direction.
Figure 25:
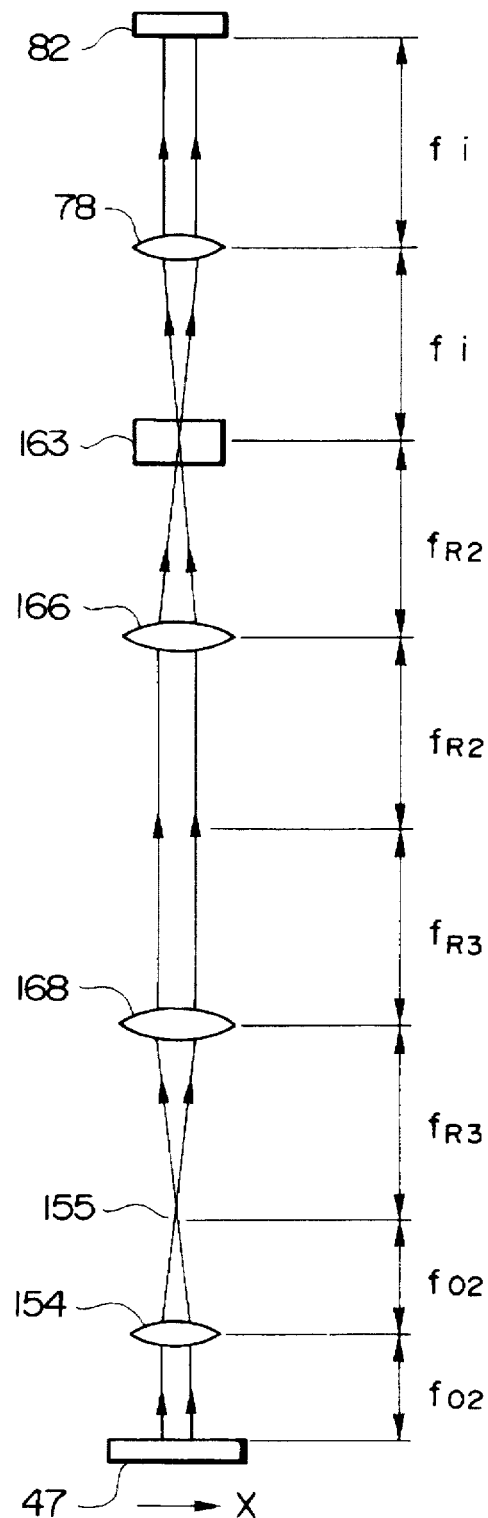
FIG. 25 is a structural diagram of the detection unit of the heterodyne interferometric optical system shown in FIG. 14 as seen from the Y-axis direction.

As shown in FIGS. 24 and 25, the front focal position of the objective lens 154 coincides with the surface of the sample 47, the rear focal position 155 of the objective lens 154 coincides with the rear focal position of the relay lens 158, the front focal position of the relay lens 168 coincides with the rear focal position 187 of the relay lens 166, the front focal position of the relay lens 166 coincides with the position of the Wollaston prism 163, the position of the Wollaston prism 163 coincides with the front focal position of the image forming lens 78, and the rear focal position of the image forming lens 78 coincides with the image pickup surface of the CCD one-dimensional sensor 82. In other words, as shown in FIG. 24, with regard to the y-direction, the principal rays of the two divergent reflected beams from the surface of the sample 47, after passing the objective 154, are focused at its rear focal position 155, and at the same time, the two beams are incident as parallel beams on the relay lens 168. Since the rear focal position of the objective lens 154 coincides with the rear focal position of the relay lens 168, the principal rays of the two beams, after passing through 168, become parallel to each other, and the two beams are simultaneously focused both at the front focal position of the relay lens 168, that is, at the rear focal position 187 of the relay lens 166. After passing through the relay lens 166, the two beams are combined by the Wollaston prism 163, and then the combined light travels as a parallel light through the image forming lens 78 and is focused at the rear focal position of the image forming lens 78, namely, the CCD one-dimensional sensor 82. On the other hand, as shown in FIG. 25, with regard to the x-direction, the two parallel reflected beams from the surface of the sample 47, after passing through the objective lens 154, are focused at the rear focal position 155 thereof, and the two beams travel through the relay lens 168 to become parallel beams which are focused at the front focal position of the relay lens 166, that is, at the position of the Wollaston prism 163. Further, the combined light, after passing through the image forming lens 78, again becomes a parallel light and is incident on the CCD one-dimensional sensor 82. As a result, on the CCD one-dimensional sensor 82, a stripe beam having a width in the x-direction and focused in the y-direction like the probe beam 181 and the reference beam 182 on the sample is obtained. In other words, a heterodyne interference light obtained from the reflected rays of the probe beam 181 and the reference beam 182 becomes a stripe beam on the CCD one-dimensional sensor 82, so that a one-dimensional light interference signal in the x-direction is detected. The structure and the function of the signal processing system 303 are exactly the same as those of the signal processing system 203 in the first embodiment, and therefore, like in the first embodiment, from an output signal of the CCD one-dimensional sensor 82, the amplitude and the phase of minute displacements at the surface of the sample 47 produced by a photoacoustic effect can be extracted without being affected by the reflectance distribution and the undulations distribution of the surface of the sample 47.

By processing a detection signal from the above-mentioned CCD one-dimensional sensor by the processor 96 while scanning the sample 47 sequentially in the x- and y-directions by using the X-Y stage 48, a two-dimensional photoacoustic image of the whole surface of the sample 47 can be obtained, and displayed on the TV monitor 97.

As has been described, according to the present embodiment, instead of the conventional so-called point scanning method for detecting information from one point after another, as shown in the first embodiment, a plurality of points being measured are excited in parallel simultaneously by a stripe-shaped excitation beam, and because light interference is used to detect a photoacoustic signal produced at the respective points, an interference light is detected in parallel simultaneously so that the photoacoustic signal at the plurality of points being measured on the sample is detected in parallel simultaneously, and thereby two-dimensional internal information on the sample can be detected at high speed.

Further, according to the present embodiment, like in the first embodiment, it is possible with only one CCD one-dimensional sensor to simultaneously detect a total of four items of information relative to the surface and the inside of the sample, namely, the reflectance distribution of the sample surface, the undulations distribution of the sample surface, the amplitude distribution of the photoacoustic signal, and the phase distribution of the photoacoustic signal, and thus, a compound assessment of a sample is possible.

Further, according to the present embodiment, like in the first embodiment, it is possible to detect the reflectance distribution of the sample surface, the undulations distribution of the sample surface, and the photoacoustic signal for which the fluctuation of the optical path has been corrected, and thus, it is possible to detect information relative to the surface and the inside of the sample with high sensitivity and stability.

Further, according to the present embodiment, like in the first embodiment, inspection of an interface inside the sample is possible by setting the intensity-modulated frequency of the excitation beam so that the heat diffusion length due to the photoacoustic effect is equal to or longer than the depth of the interface being inspected between the Cu wiring pattern and the ceramic substrate.

Further, according to the present embodiment, like in the first embodiment, for extracting a photoacoustic signal from the light interference signal, a digital frequency filtering process is used instead of the analog frequency filtering process, so that detection of the photoacoustic signal can be performed with high sensitivity and high accuracy while being hardly subject to the influence of high harmonic components.

Further, according the present embodiment, a differential interferometric optical system is used as the interferometric optical system for detecting minute displacements of the sample surface caused by the photoacoustic effect. More specifically, instead of obtaining a reference light from a reference mirror separately installed, a reflected light of the reference beam, which is incident near the probe light and is reflected by the sample surface, is used as the reference light, so that the probe light and the reference light travel along substantially the same optical path and through the same optical system, and thus, the fluctuation of the optical path length and the displacement of the wave front between the two beams of light are reduced greatly, and the detection accuracy and the detection sensitivity of a photoacoustic signal are improved remarkably.

Moreover, since the need to provide a reference light path is obviated, the optical system is simplified and increased in stability, and the detection accuracy of the photoacoustic signal improves.

Incidentally, in this embodiment, description has been made of the examples in which the present invention is applied to samples having a plurality of objects under inspection with anotable thermal contrast, but the present invention can be applied sufficiently to samples made of a homogeneous material containing an internal crack, for example. Even in this case, a plurality of points being measured on the sample can be excited simultaneously, and therefore, the above-mentioned effects can be expected.

Figure 26:
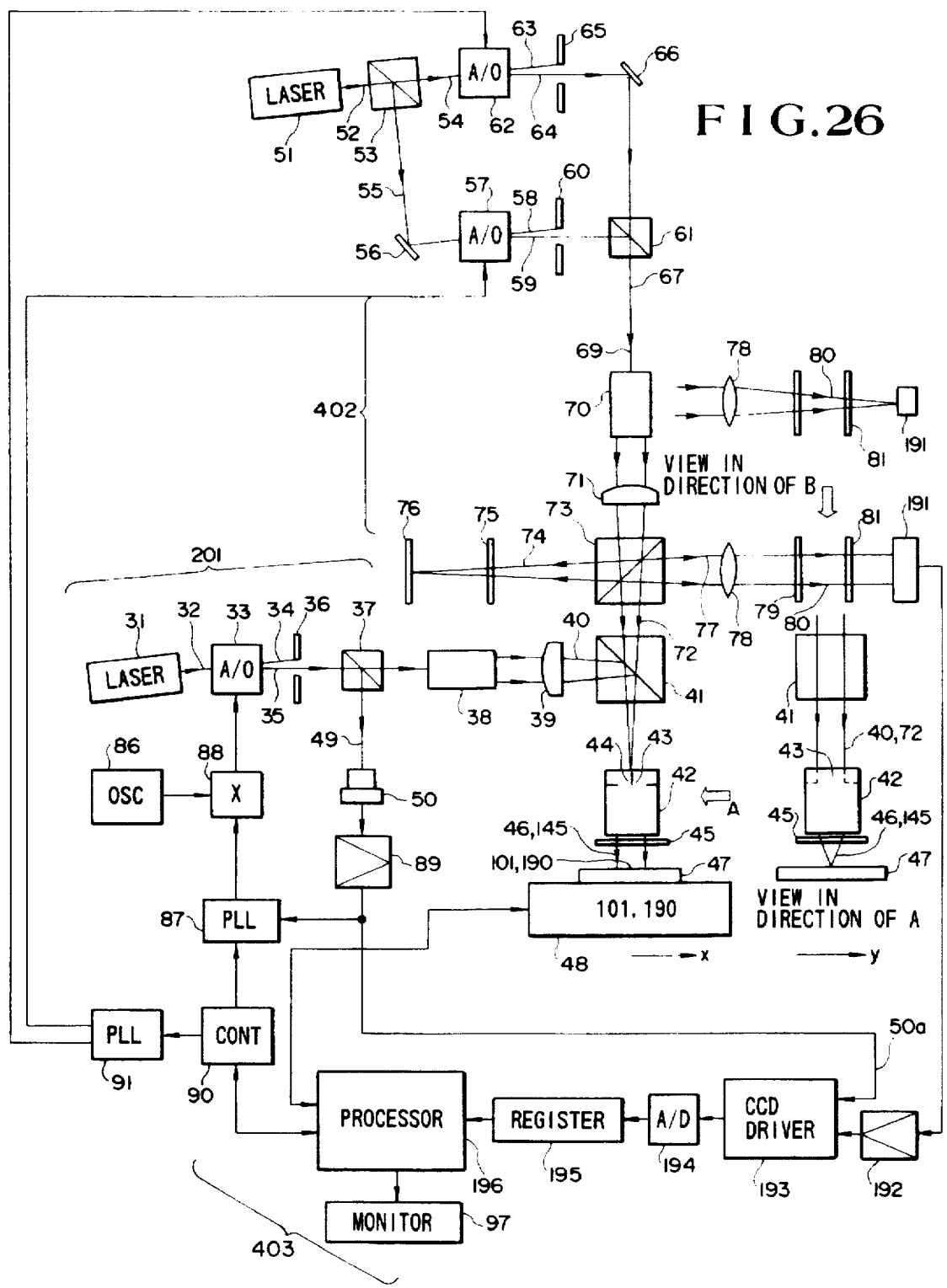
FIG. 26 is a diagram of a structural example of the photoacoustic detection apparatus in a third embodiment of the present invention.

A third embodiment of the present invention will be described with reference to FIGS. 26 and 27. FIG. 26 shows a photoacoustic detection optical system according to a third embodiment. This optical system includes an excitation optical system 201, a heterodyne Twyman-Green interferometric optical system 402 for detecting a photoacoustic signal, and a signal processing system 403. The structure and the function of the excitation optical system 201 are exactly the same as in the first embodiment, and their description are omitted. The structure of the heterodyne Twyman-Green interference optical system 402 is the same as in the first embodiment, only differences being that the beam splitter 68 for detecting a beat signal, the polarizing plate 83, and the photoelectric converting element 85 have been removed and a parallel output type photoelectric converting element array 191 is used in place of the storage type CCD one-dimensional sensor 82 for detecting an interference signal in the heterodyne Twyman-Green interferometric optical system 202 in the first embodiment, and therefore, its description is omitted.

Figure 27:
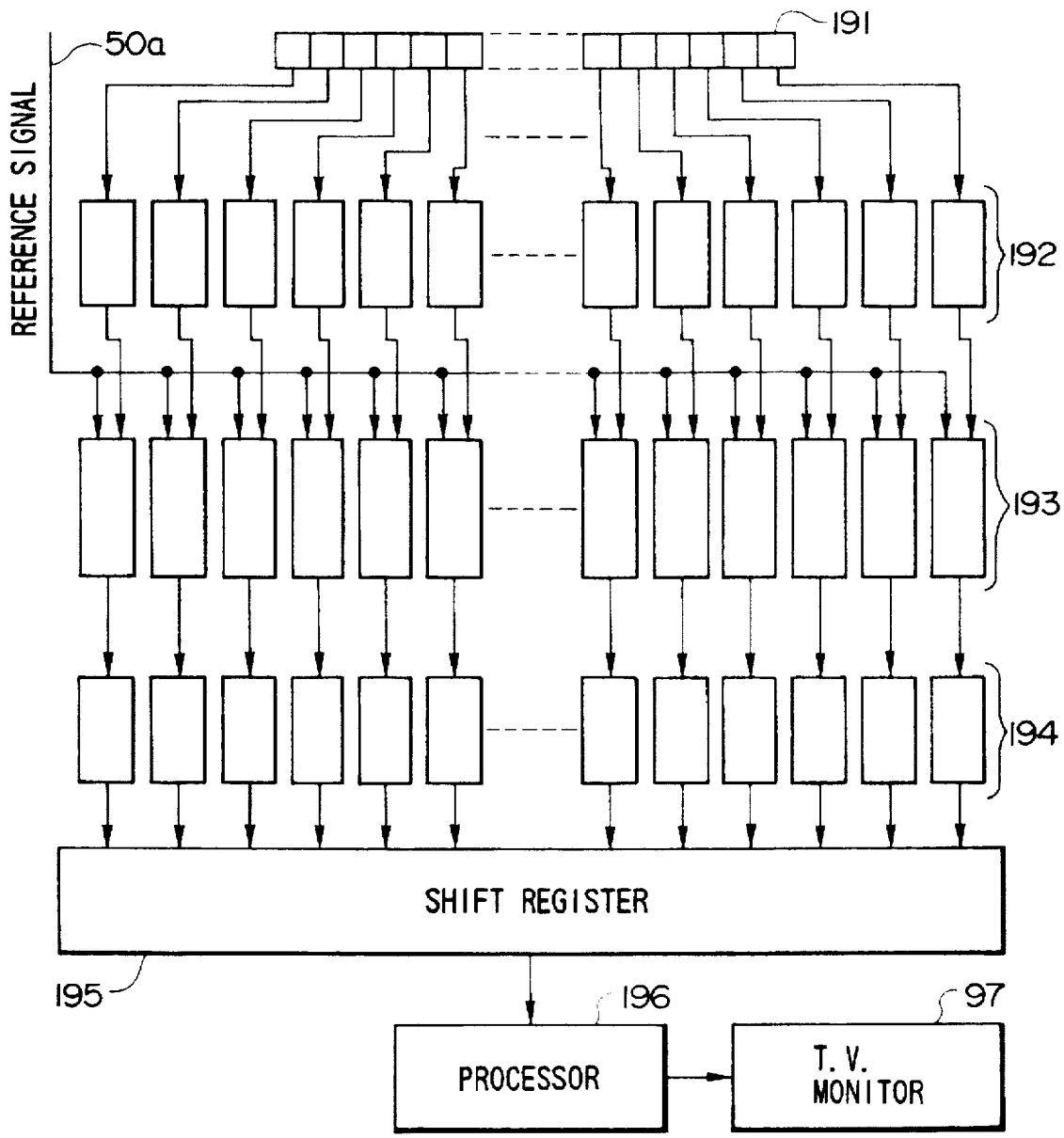
FIG. 27 is a diagram of a structural example of the signal processing system in the third embodiment.

As shown in FIG. 27, the light interference signal output from the respective pixels of the parallel output type photoelectric converting element array 191 is amplified for the individual pixels by a group of preamplifiers 192 arranged as many as the number of the pixels, and then, the intensity-modulated signal 50a detected by the photoelectric converting element 50 is sent as a reference signal to a group of lock-in amplifiers 193 and the modulated frequency component included in the light interference signal is sent as the photoacoustic signal to the group of lock-in amplifiers 193, so that the amplitude and the phase of the minute displacements of the surface of the sample 47 produced by the photoacoustic effect are detected for all pixels simultaneously. The detected photoacoustic signal is converted into digital data by a group of A/D converter 194, and subsequently, sent to a parallel-in, serial-out type shift register 195 to be converted into a one-dimensional signal. A position signal of the X-Y stage 48 and an output signal from the shift register 195 are processed by a processor 196, and the photoacoustic signal at the respective points of the sample 47, that is, a two-dimensional photoacoustic image of the whole surface of the sample 47 is obtained and displayed on the TV monitor 97. Meanwhile, in this embodiment, the non-storage type parallel output photoelectric converting element array 191 is used as the interference light detecting sensor, but a storage type may be used. In this case, the signal processing system 403 can be used as is. Or, in the signal processing system 403, it is possible to remove the group of lock-in amplifiers 193, and obtain signals whose phase is shifted among them by controlling the storage time in the photoelectric converting element array based on the expression 4 to the expression 6 like in the first or second embodiment and make the processor to perform arithmetic operations based on the expression 16 to the expression 19.

This embodiment can be applied sufficiently to samples having a plurality of objects under inspection which exhibit a conspicuous thermal contrast, and also to samples made of a homogeneous material containing an internal crack as shown in FIGS. 8, 9A, and 9B.

As has been described, according to the present embodiment, instead of the conventional so-called point scanning method for detecting information from one point after another, as shown in the first and second embodiments, a plurality of points being measured are excited in parallel simultaneously by a stripe-shaped excitation beam, light interference is used to detect a photoacoustic signal produced at the respective points, and an interference light is detected in parallel so that the photoacoustic signal at the plurality of points being measured on the sample is detected simultaneously, whereby two-dimensional internal information on the sample can be detected at high speed.

Further, if a storage type one-dimensional sensor is used in the present embodiment, as shown in the first embodiment, it is possible by only one-dimensional sensor to simultaneously detect a total of four items of information on the surface and the inside of the sample, namely, the reflectance distribution of the sample surface, the undulations distribution of the sample surface, the amplitude distribution of the photoacoustic signal, and the phase distribution of the photoacoustic signal, so that a compound assessment of a sample becomes possible.

Further, if a storage type one-dimensional sensor is used in the present embodiment, as shown in the first embodiment, it is possible to detect the reflectance distribution of the sample surface, the undulations distribution of the sample surface, and the photoacoustic signal for which the fluctuation of the optical path has been corrected, and thus, detection of information on the surface and the inside of the sample with high sensitivity and stability becomes possible.

Further, if a storage type one-dimensional sensor is used in the present embodiment, as shown in the first embodiment, inspection of an interface inside the sample is possible by setting the intensity-modulated frequency of the excitation beam so that the heat diffusion length due to the photoacoustic effect is equal to or longer than the depth of the interface being inspected between the Cu wiring pattern and the ceramic substrate.

Further, if a storage type one-dimensional sensor is used in the present embodiment, like in the first embodiment, for extracting a photoacoustic signal from the light interference signal, a digital frequency filtering process is used instead of the analog frequency filtering process, so that detection of the photoacoustic signal can be performed with high sensitivity and high accuracy while being hardly subject to the influence of high harmonic components.

Incidentally, it is possible to store the light interference signal from the pixels of the non-storage type photoelectric array 191 in the two-dimensional memory, and thereafter, read the light interference signal from one pixel after another and detect the photoacoustic signal by one lock-in amplifier as a one-dimensional signal.

Figure 28:
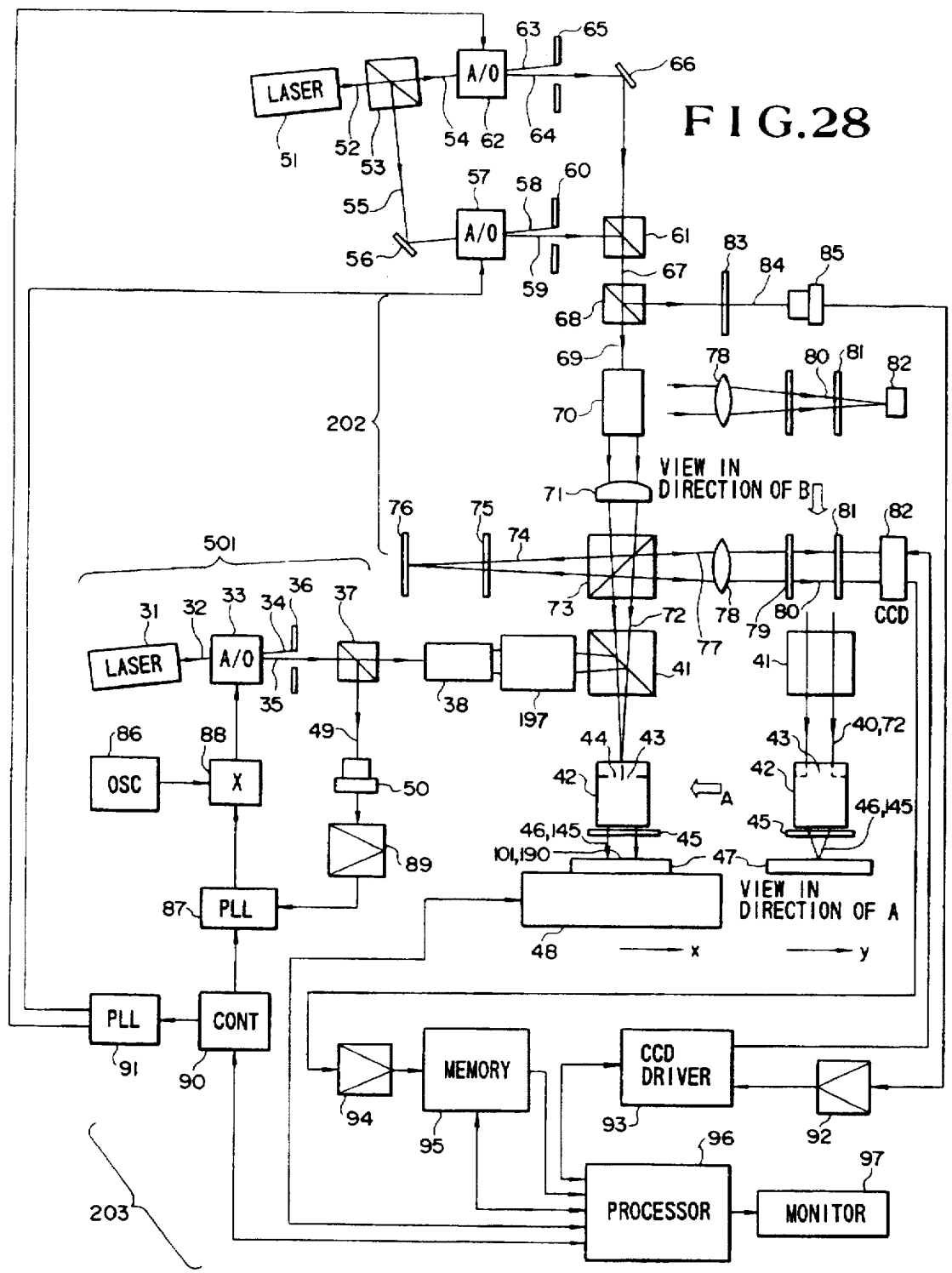
FIG. 28 is a diagram of a structural example of the photoacoustic detection apparatus in a fourth embodiment.
Figure 29:
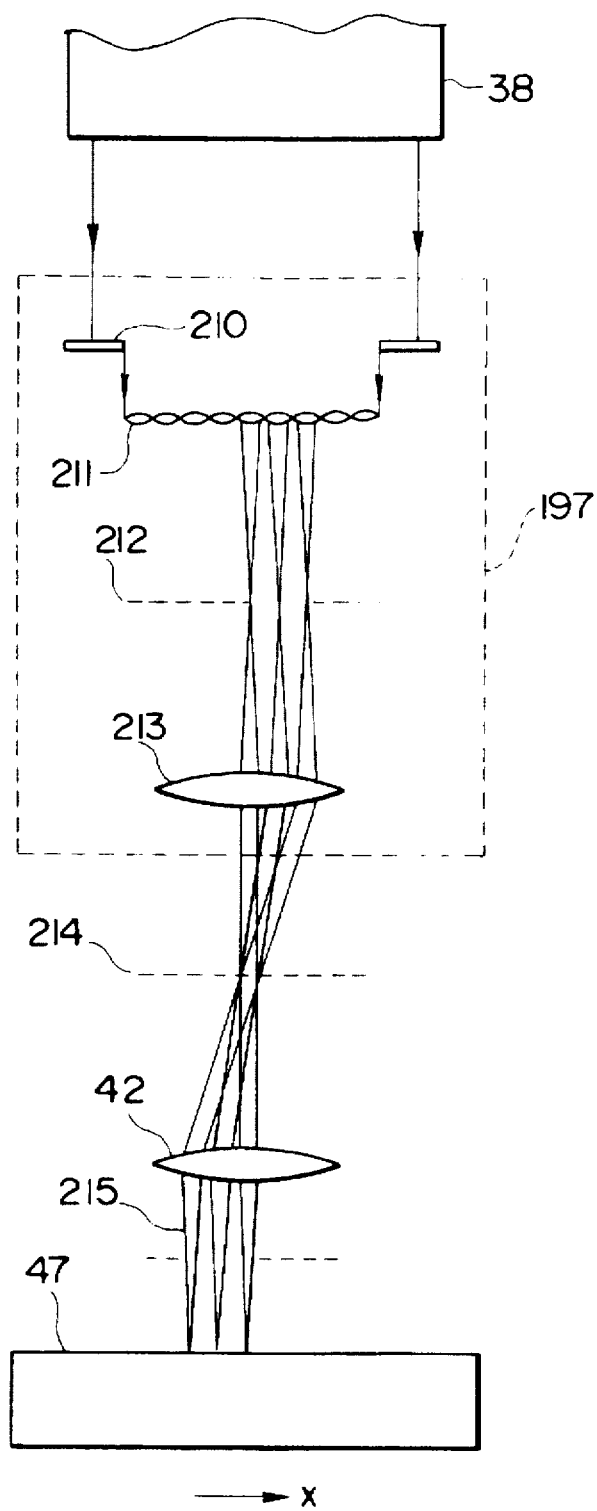
FIG. 29 is a diagram of a structural example of a multiple spot beam parallel-irradiation optical system in the fourth embodiment.
Figure 30:
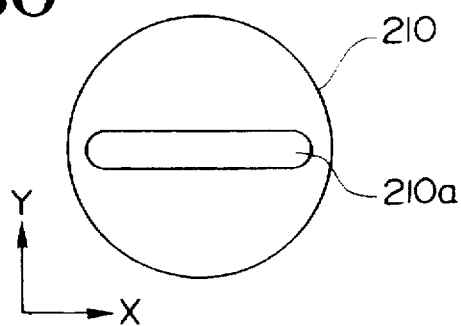
FIG. 30 is a diagram showing a shape of a mask of a multiple spot beam parallel-irradiation optical system in the fourth embodiment.

A fourth embodiment of the present invention will be described with reference to FIGS. 28 to 32. FIG. 28 shows a photoacoustic detection optical system in the fourth embodiment. This optical system includes an excitation optical system 501, a heterodyne Twyman-Green interferometric optical system 202 for detecting a photoacoustic signal, and a signal processing system 203. The structure and the function of the heterodyne Twyman-Green interferometric optical system 202 and the signal processing system 203 are exactly the same as in the first embodiment, and their description is omitted.

Figure 31:
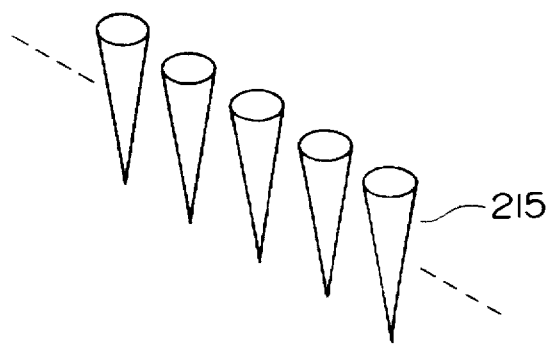
FIG. 31 is a diagram showing simultaneous irradiation of multiple spot beams to the sample in the fourth embodiment.

Whereas the stripe-shaped excitation beam is used in the first, second and third embodiments, one notable difference of this fourth embodiment from the foregoing ones is that a multiple-spot-beam parallel irradiation optical system 197 is adopted in the excitation optical system 501. The other component parts are the same as in the first to the third embodiments. With reference to FIG. 31, the multiple-spot-beam parallel irradiation optical system 197 will be described. An expanded parallel light from the beam expander 38 passes through the stripe-shaped opening 210a of a mask 210 and becomes a stripe beam and is incident on a one-dimensional minute lens array 211. The rear focal positions of the minute lenses coincide with the front focal position 212 of the relay lens 213, the rear focal position of the relay lens 213 coincides with the rear focal position 214 of the objective lens 42, and the front focal position of the objective lens 42 coincides with the surface of the sample 47. The beams from the one-dimensional minute lens array 211 are focused at the front focal position 212 of the relay lens 213, and after passing through the relay lens 213, become parallel beams, and after passing through the objective lens 42, are focused as convergent spot beams on the surface of the sample 42. Meanwhile, the principal rays of the spot beams are parallel to each other. FIG. 31 shows the state that the respective spot beams irradiate the sample simultaneously. The number of the spot beams is matched with the number of the pixels of the CCD one-dimensional sensor 82 for light interference detection, and the distances between them are arranged so that the heat diffusion regions 217 generated by the spot beams do not overlap each other. The probe beam for heterodyne interference detection is shaped in a stripe like in the first to third embodiments. The structure and the function of the signal processing system 203 are exactly the same as in the first embodiment. Like in the first embodiment, from the output signal of the CCD one-dimensional sensor 82, the amplitude and the phase of the minute displacements of the surface of the sample 47 caused by the photoacoustic effect can be extracted without being affected by the reflectance distribution and the undulations distribution of the surface of the sample 47.

By processing a detection signal from the above-mentioned CCD one-dimensional sensor by the processor 96 while scanning the sample 47 sequentially in the x- and y-directions by using the X-Y stage 48, a two-dimensional photoacoustic image of the whole surface of the sample 47 can be obtained, and displayed on the TV monitor 97.

This embodiment can be applied sufficiently to samples having a plurality of objects under inspection which exhibit a conspicuous thermal contrast, and also to samples made of a homogeneous material containing an internal crack as shown in FIGS. 8, 9A, and 9B.

As has been described, according to the present embodiment, instead of the conventional so-called point scanning method for detecting information from one point after another, a plurality of points being measured are excited in parallel simultaneously by irradiating a plurality of spot beams in parallel simultaneously, because light interference is used to detect a photoacoustic signal produced at the respective points, an interference light is detected in parallel simultaneously so that the photoacoustic signal at the plurality of points being measured on the sample is detected in parallel simultaneously, and thereby two-dimensional internal information on the sample can be detected at high speed.

Further, according to the present embodiment, because the heat diffusion regions of the respective excitation beams do not overlap each other, a resulting effect is improved resolution in detecting a photoacoustic image.

Further, according to the present embodiment, like in the first embodiment, by only one CCD one-dimensional sensor, it is possible to simultaneously detect a total of four items of information relative to the surface and the inside of the sample, i.e., the reflectance distribution of the sample surface, the undulations distribution of the sample surface, the amplitude distribution of the photoacoustic signal, and the phase distribution of the photoacoustic signal, and thus, a compound assessment of a sample becomes possible.

Further, according to the present embodiment, like in the first embodiment, it is possible to detect the reflectance distribution of the sample surface, the undulations distribution of the sample surface, and the photoacoustic signal for which the fluctuation of the optical path has been corrected, and thus, detection of information relative to the surface and the inside of a sample with high sensitivity and stability becomes possible.

Further, according to the present embodiment, like in the first embodiment, inspection of an interface inside the sample is possible by setting the intensity-modulated frequency of the excitation beam so that the heat diffusion length due to the photoacoustic effect is equal to or longer than the depth of the interface being inspected between the Cu wiring pattern and the ceramic substrate.

Further, according the present embodiment, like in the first embodiment, for extracting a photoacoustic signal from the light interference signal, a digital frequency filtering process is used instead of the analog frequency filtering process, so that detection of the photoacoustic signal can be performed with high sensitivity and high accuracy while being hardly subject to the influence of high harmonic components.

Incidentally, in the present embodiment, the storage type CCD one-dimensional sensor is used for detecting an interference light, but as in the third embodiment, a non-storage type parallel-output photoelectric converting element array may be used. In this case, it is only necessary to use the signal processing system 403 in the third embodiment.

In the first to third embodiments described above, the excitation beam and the probe beam both in a one-dimensional stripe form are used, but a beam in a two-dimensional form having a certain area may be used. In this case, a two-dimensional sensor is used for detecting an interference light as a matter of course. Likewise, also in the fourth embodiment, it is possible to arrange a plurality of spot beams in a two-dimensional form and use a two-dimensional sensor.

Another embodiment of the present invention will next be described with reference to FIGS. 33 to 44.

Figure 34:
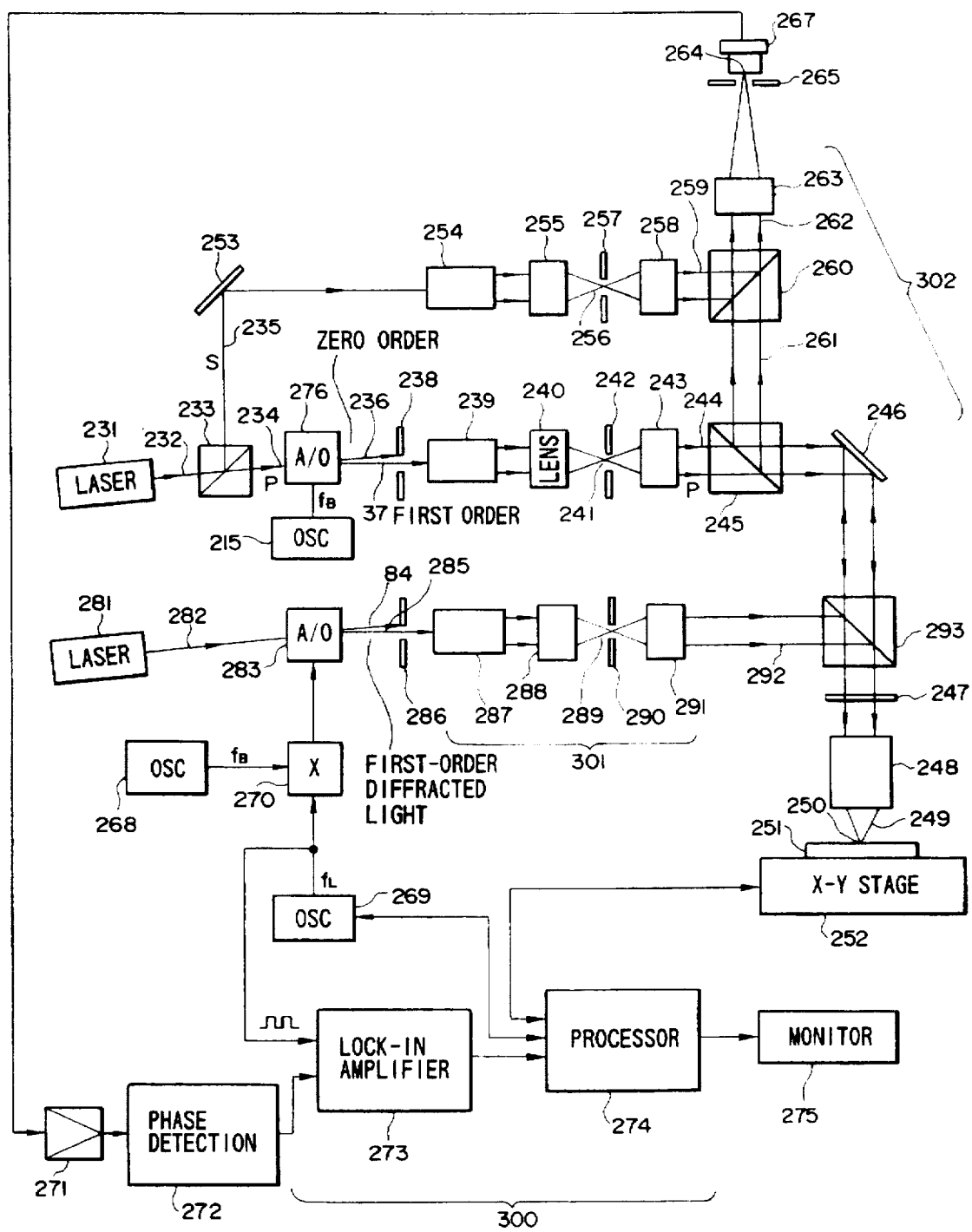
FIG. 34 is a diagram showing a structure in one example of the photoacoustic signal detection unit according to FIG. 33.
Figure 36A:
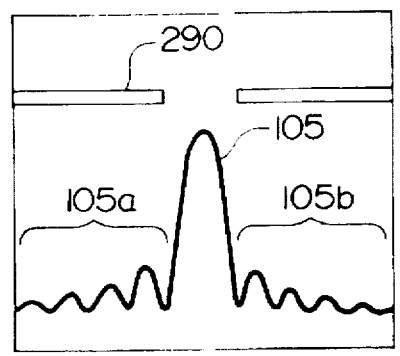
FIGS. 36A and 36B are diagrams showing states of shielding a high-order diffracted light component.
Figure 36B:
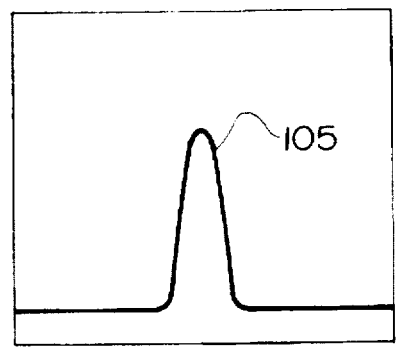

First of all, the photoacoustic signal detection apparatus is described, and FIG. 34 shows an example of its structure. In this case, the photoacoustic signal detection apparatus comprises an excitation optical system 301, a heterodyne Mach-Zehnder interference optical system 302 for detecting a photoacoustic signal, and a signal processing system 300, if the component sections are roughly divided. A parallel laser beam 282 from an Ar laser oscillator (wavelength 515 nm) 281 has its intensity modulated to a desired form by an acousto-optical modulating element 283. An oscillator 268 outputs a sine wave signal 98 with a frequency of $f_B$ as shown in FIG. 35A, and an oscillator 269 outputs a square wave signal 99 with a frequency of $f_L$ ($f_L < f_B$) as shown in FIG. 35B. These signals 98 and 99 are combined by the signal synthesizer 270 to supply a product of the two waveforms, and the resultant intensity modulation frequency signal 100 is as shown in FIG. 35C. By this intensity modulation frequency signal 100, the parallel laser beam 282 striking the acousto-optical modulating element 283 has its intensity modulated to a desired form. As a result, the acousto-optical modulating element 283 intermittently outputs a first-order diffracted light 285 with a frequency of $f_L$, which has been shifted by $f_B$. In other words, an intensity-modulated beam with an intensity-modulated frequency of $f_L$ shifted by $f_B$ can be obtained as an excitation beam. In this process, a zero-order light 284 is intercepted by a diaphragm 286. The intensity-modulated beam 285 from the acousto-optical modulating element 283 has its beam diameter expanded by a beam expander 287 to a desired length, and then, the beam 185 is focused by a lens 288 at its rear focal position 289. At this rear focal position 289, there is provided a pin-hole 290, by which the high-order diffracted light elements are removed. As shown in FIG. 36A, the high-order diffracted light components 105a and 105b present at the surrounding area of the peak portion 105 at the focusing spot are intercepted by the pin-hole 290, and in consequence, the light intensity distribution after passage of the pin-hole 290 becomes the one having only the peak portion 105 as shown in FIG. 36B. Since the rear focal position 289 is also the front focal position of the lens 291, the luminous flux after passage of the pin-hole 290 becomes a parallel excitation light 292 as it passes through the lens 291. The parallel excitation light 292 is reflected by a dichroic prism (reflects wavelengths 600 nm or less, transmits wavelengths more than 600 nm) 293, and travels through a λ/4 plate 247, and is focused at the front focal position 250 of an objective lens 248, that is, the excitation beam 292 falls on the focusing position of a sample 251 as a light spot having a light intensity distribution like the one shown in FIG. 36B. In other words, the front focal position 289 of the lens 291 is in a conjugate and confocal relation with the front focal position 250 of the objective lens 248. At the front focal position (focusing spot) 250 on the sample 251 to which the parallel excitation light 292 in a focused state is irradiated, an ultrasonic wave (thermoplastic wave) is generated by a thermal distortion wave caused by a photoacoustic effect, and at the same time, at the focusing spot 250 on the surface of the sample 251, minute displacements occur, which change periodically at the intensity-modulated frequency of $f_L$ of the parallel excitation light 292.

Figure 37:
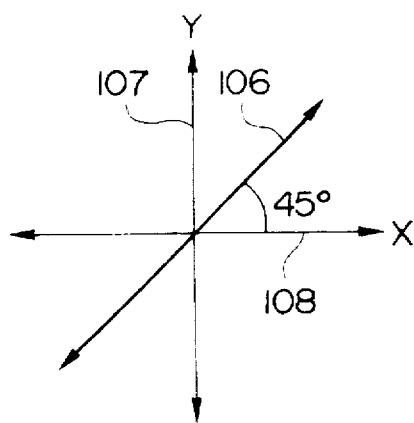
FIG. 37 is a diagram showing a polarization of a laser light as a generating source of a probe light and a reference light in obtaining an interference light including information about the minute displacements generated at the sample surface by the excitation light.

Meanwhile, in the Mach-Zehnder interferometric optical system 302, the polarization direction of a linearly polarized beam 232 from a He—Ne laser oscillator (wavelength 633 nm) 231 is set at 45° respectively to the x- and the y-directions as indicated as the polarization direction 106 in FIG. 37 (the direction perpendicular to paper of FIG. 34 is designated as the x-axis and the direction at right angles to the x-axis is designated as the y-axis). Of the linearly polarized beam 232 from the He—Ne laser oscillator 231, a p-polarized component 234 shown as a p-polarized component 107 in FIG. 37 is allowed by a polarization beam splitter 233 to transmit therethrough and is incident on an acousto-optical modulating element 276, while an s-polarized component 235 shown as an s-polarized component 108 in FIG. 37 is reflected by the polarization beam splitter 233 in the direction of a mirror 253. Meanwhile, as a sine wave 98 of frequency $f_B$ shown in FIG. 35A is supplied to the acousto-optical modulating element 276 from an oscillator 215, the acousto-optical modulating element 276 outputs a first-order diffracted light 237 shifted in frequency by $f_B$. The first-order diffracted light 237 with the accompanying zero-order light 236 removed by the diaphragm 238 is expanded to a desired beam diameter by a beam expander 239, and then, is focused at the rear focal position 241 of a lens 240. Since at the rear focal position 241, there is provided a pin-hole 242, the high-order diffracted light components 105a and 105b present at the surrounding area of the peak portion 105 at the focusing spot are intercepted, and after passage of the pin-hole 242, the light intensity distribution of the first-order diffracted light 237 becomes the one having only the peak portion 105 as shown in FIG. 36B. Since the rear focal position 241 of the lens, after passage of the pin-hole 242, the first-order diffracted light 237 again becomes a parallel light 244 as it passes the lens 243. This parallel light 244 comprises the p-polarized beam, and therefore, after passing as it is through a beam splitter 245, the light 244 is reflected by a mirror 246, and then, travels through the dichroic prism 293 and the λ/4 plate 247 and becomes a circularly polarized light. The circularly polarized light focused by the objective lens 248 at its front focal position 250, namely, at the focusing position on the sample 251 as a converged light spot having a light intensity distribution similar to the one shown in FIG. 36B. More specifically, the front focal position 241 of the lens 243 is in a conjugate and confocal relation with the front focal position 250 of the objective lens 248. The reflected light from the front focal position (focusing spot) 250 on the sample 251 on which the converged parallel light 244 falls contains minute displacements produced on the surface of the sample 251 as phase information. The reflected light, after passing the objective lens, becomes a parallel light, and by traveling through a λ/4 plate 247, is made into an s-polarized light, which propagates back along the same optical path and is reflected by a polarization beam splitter 245. The s-polarized beam 261 from the polarization beam splitter 245 passes through a non-polarization beam splitter 260 and is caused to interfere with a reference light 259 reflected from the non-polarization beam splitter 260.

The reference light 259 is made from the s-polarized component 235 reflected by the polarization beam splitter 233. The s-polarized component 235 from the polarization beam splitter 233 is reflected by the mirror 253, and has its beam diameter expanded to a desired length by a beam expander 254, and then, is focused by a lens 255 at its rear focal position 256. By a pin-hole 257 provided at the rear focal position 256, the high-order diffracted light components 105a and 105b present around the peak portion 105 at the focusing spot are intercepted as shown in FIG. 36A, with the result that the light intensity distribution of the s-polarized component 235, after passing the pin-hole, 257 becomes the one having only the peak portion 105 as shown in FIG. 36B. Since the rear focal position 256 also serves as the front focal position of the lens 258, the s-polarized component 235 having passed the pin-hole 257 is obtained as a parallel reference light 259 as it comes out of the lens 258. This parallel reference light 259, after being reflected by the non-polarization beam splitter 260, is caused to interfere with the s-polarized beam 261 reflected from the surface of the sample 251 and passed through the non-polarization beam splitter 260, and thereby an interference light 262 is obtained. The interference light 262 contains minute displacements of the surface of the sample 251 caused by the photoacoustic effect as light phase information. The interference light 262 travels through a lens 263, and is detected as an interference intensity signal by a photoelectric converting element 267, such as a photodiode, disposed at the rear focal position 264 of the lens 263. In the Mach-Zehnder interferometric optical system 302, the front focal position 241 of the lens 243, the front focal position 256 of the lens 258, the front focal position 250 of the objective lens 248, and the rear focal position 264 of the lens 263 are located in conjugate and confocal relation with one another. In addition, since there is provided a pin-hole 265 at the rear focal position 264 of the lens 263, stray light occurring in the objective lens 248, an interference component occurring in the transparent thin film on the sample 251, and high-order diffracted light components occurring produced by the minute undulations on the surface of the sample 251 can be intercepted, so that the minute displacements caused by the photoacoustic effect can be detected by the photoelectric converting element 267 in an improved condition.

Figure 33:
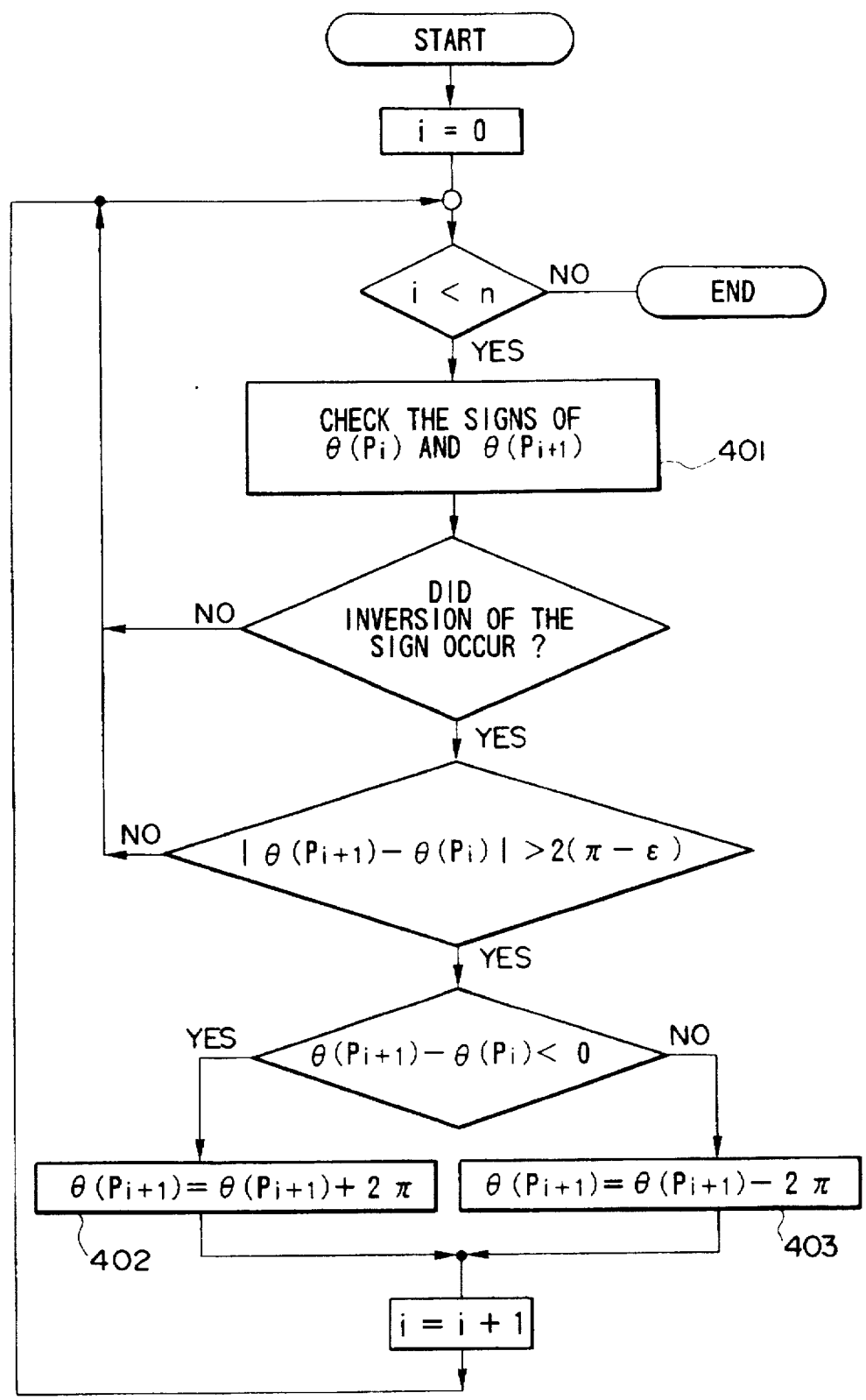
FIG. 33 is a flowchart showing an example of a phase jump presence detecting and phase jump correcting process in the present invention.

In the manner as described, the interference intensity signal is obtained by the Mach-Zehnder interferometric optical system 302, and then, the interference intensity signal is processed by the signal processing system 300 as specified. The interference intensity signal contains information relative to the amplitude A and the phase θ connected with the minute displacement at the surface of the sample 251, which is produced at the intensity-modulated frequency $f_L$, and this information is obtained by using the signal processing system 300. As shown in FIG. 34, the interference intensity signal from the photoelectric converting element 267 is sent through a pre-amplifier 271 to a phase detection circuit 272 which extracts only a d.c. component and a $f_L$ frequency component from the interference intensity signal. By using a sine wave of frequency $f_L$ from an oscillator 269 as a reference signal, a lock-in amplifier 273 obtains the amplitude and the phase of the frequency component of $f_L$ in the end. From the amplitude and the phase, the processor 274 obtains the amplitude A and the phase θ according to the minute displacement at the surface of the sample 251. The amplitude A and the phase θ thus obtained contain thermoplastic information as to the heat diffusion region ($V_{th}$) defined by the intensity-modulated frequency $f_L$. Therefore, if there is an internal defect, such as a crack, in the heat diffusion region ($V_{th}$), the amplitude A and the phase θ change, accordingly, and from such changes, the presence of the crack is detected. In this process, the laser-light-irradiated positions on the sample 251 are controlled through an X-Y stage 252 by the processor 274 which specifies one position after another as the position whose data is to be updated. The real laser-light-irradiated position is known by the processor 274 from a position detection signal from the X-Y stage 252. If such an arrangement is made that the processor 274 processes the intensity-modulated frequency component from the lock-in amplifier 273 in conjunction with the real laser-light-irradiated position each time the laser light is irradiated to the sample 251, then the photoacoustic signal corresponding to the real laser-light-irradiated positions can be obtained to output a two-dimensional photoacoustic image on a display 275. In this case, the processor 274 will be performing a phase jump detection and correction process when a phase jump exists, in addition to a general process to obtain the photoacoustic image. FIG. 33 shows a routine for detecting a phase jump and correcting the phase jump in line units in the x-direction.

The phase jump detection and correction process will be described with reference to FIGS. 38A and 38B.

FIG. 38A shows a phase shift signal 413 having a notable phase jump at a pixel $P_1$. The phase jump detection process in this case is arranged such that a check is made at the block 401 in FIG. 33 whether the sign is the same for the phase signals θ ($P_0$) and θ ($P_1$) at two adjacent pixels $P_0$ and $P_1$ on the premise that a phase jump has not occurred in the phase signal θ ($P_0$) at the first pixel $P_0$. If there is an inversion of the sign between the θ ($P_0$) and θ ($P_1$), supposing that there could be a phase jump in the phase signal θ ($P_1$), a check is also made whether a difference in phase, that is, the absolute value of θ ($P_1$) −θ ($P_0$) is greater than 2 (π−ε) (the constant ε will be described later). As is clear from FIG. 38A, since |θ ($P_1$)−θ ($P_0$)|>2 (π−ε), a decision is made that a phase jump exists. To the phase signal θ ($P_1$) at the pixel P for which a decision has been given that a phase jump exists, 2π or −2π is added by the phase jump correction process. Which is added is decided according to the phase difference, namely, the sign of θ ($P_1$)−θ ($P_0$). If the phase difference is minus, it follows that the θ ($P_1$) took a phase jump of −2π, and 2π is added to the θ ($P_1$), whereas conversely, if the phase difference is plus, −2π is added to the θ ($P_1$). In this manner, the phase jump correction is performed. In the case shown in FIG. 38A, in the block 402 in FIG. 33, 2π is added to the phase signal θ ($P_1$) at the pixel $P_1$ to correct the phase jump. Thereafter, the value of i is incremented by +1, the process mentioned above is performed for the pixels $P_1$ and $P_2$'. Since a phase jump has been carried out for the phase signal θ ($P_1$) at the pixel $P_1$, the inversion of the sign does not occur between the phase signals θ ($P_1$) and θ ($P_2$), and therefore, a phase jump correction is not performed for the phase signal θ ($P_2$) at the pixel $P_2$. So is the case with the pixels $P_3$ and $P_4$. From the phase signal θ ($P_3$) to the phase signal θ ($P_4$), there is an inversion of the sign, but, since the absolute value of the phase difference is not greater than 2(π−ε), a phase jump correction is not carried out. FIG. 38B shows the phase signal 414 after a phase jump correction has been done for the phase signal 413. The abnormality of the phase signal 413 due to the phase jump at the pixel $P_1$ has been eliminated. In the forgoing description, in the phase jump correction, whether to add 2π or −2π is decided according to the sign of the phase difference between the adjacent two pixels $P_i$ and $P_{i+1}$, but, of course, this decision may be made according to the signs of the phase signals θ ($P_i$) and θ ($P_{i+1}$).

The constant ε introduced in the calculation of the phase difference will next be described with reference to FIG. 39. As has been described, the photoacoustic signal is obtained by detecting at certain sampling intervals the thermal distortion of the sample surface caused by the photoacoustic effect or the photothermal effect generated by irradiation of the intensity-modulated light to the focusing point on the sample. Therefore, as shown in FIG. 39, there occurs such a case in which at sampling intervals of some length, the photoacoustic signal is detected at positions $R_1$ and $R_2$, for example, away from the point Q where a phase jump actually occurs. As a result, the detected phase signal values θ ($R_1$) and θ ($R_2$) are respectively θ ($R_1$)<π and θ ($R_2$)>−π, so that the phase difference between the two phase signals is smaller than 2π, and if the criterion is set at 2π, there is a high possibility that a phase jump is overlooked, and it is difficult to make a decision on presence or absence of a phase jump. To make it possible to correctly render a presence/absence decision of a phase jump even in the above case, the constant ε is introduced. To be more specific, the value of ε is set suitably for individual cases to tolerate a phase shift signal error resulting from a round-off error owing to the discretization and digitization of the detected photoacoustic signal, and a calculation error in processing the detected signal. In this embodiment, the constant ε is set at π/6 to execute a phase jump correction.

Figure 1:
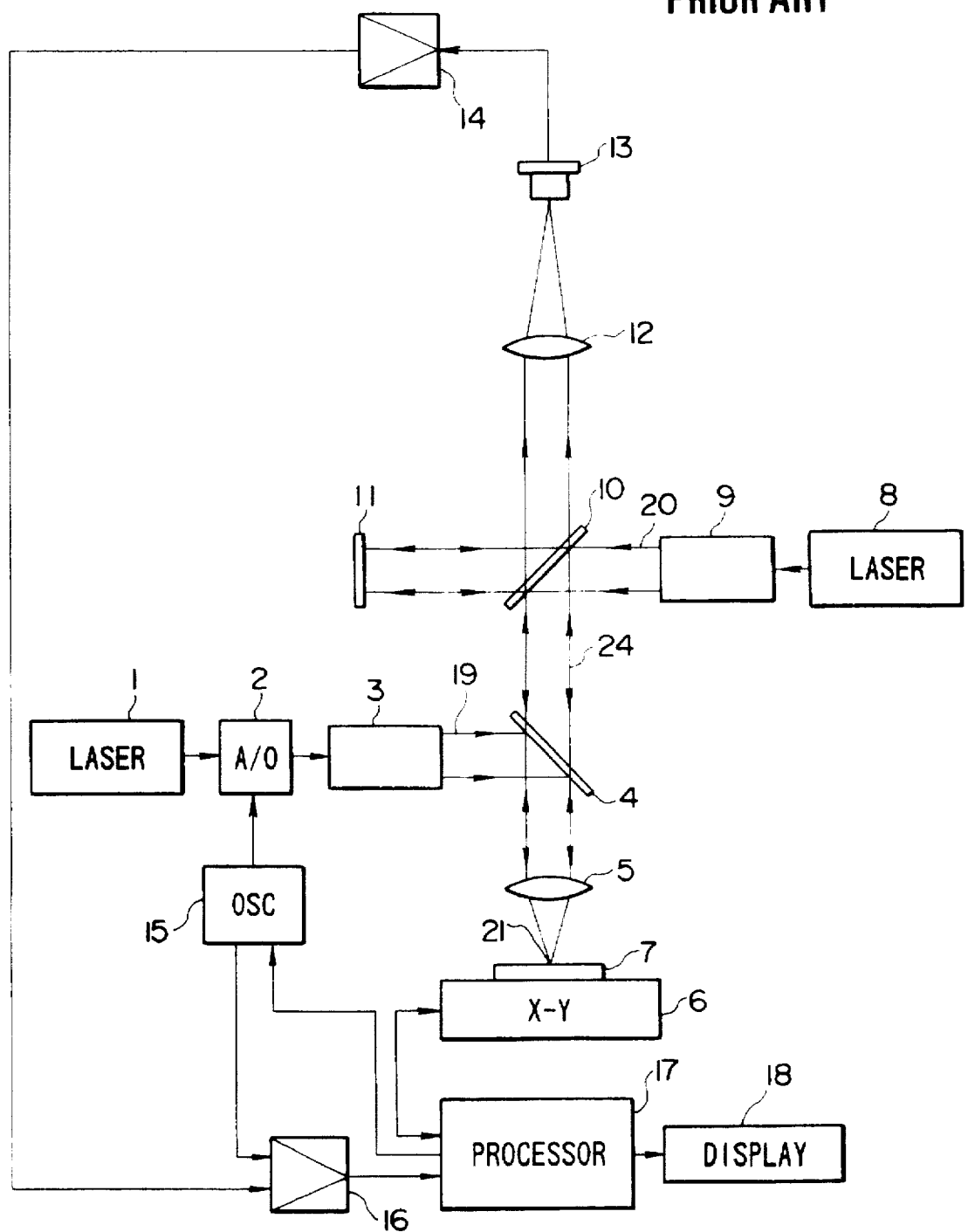
FIG. 1 is a diagram showing a structural example of the conventional photoacoustic detection optical system.
Figure 2:
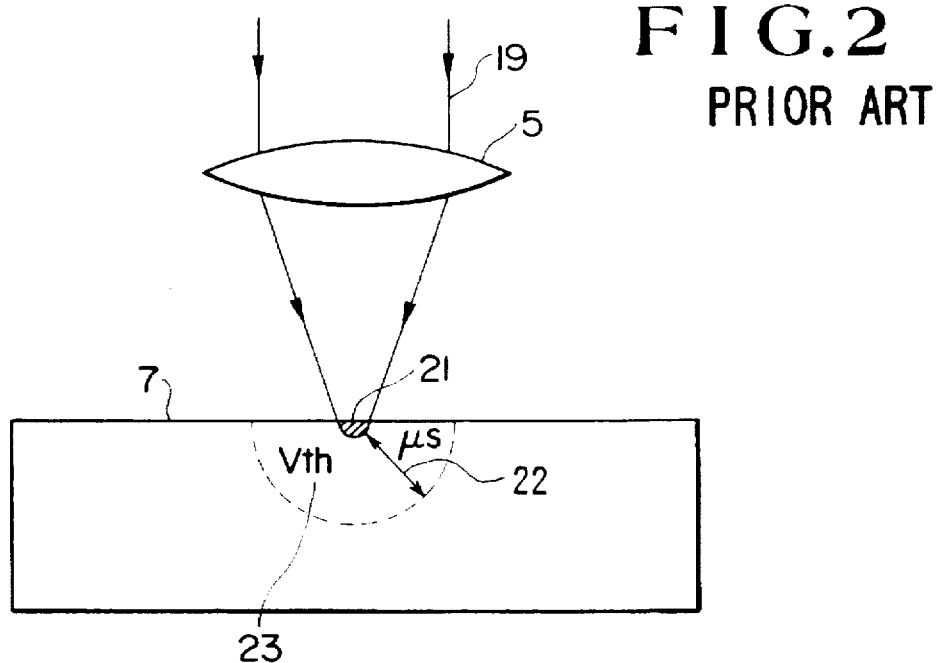
FIG. 2 is a diagram showing the principle of a photoacoustic effect.
Figure 3A:
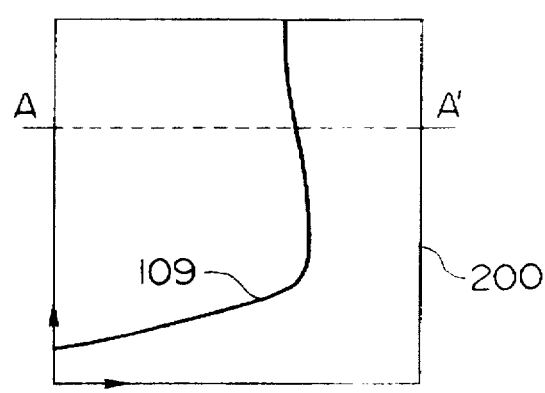
FIG. 3A is a plan view of a crack in the surface of a sample.
Figure 3B:
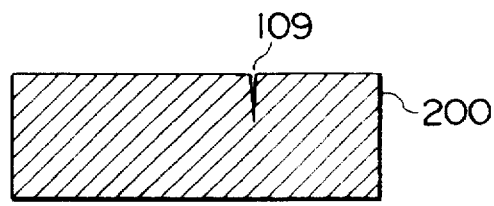
FIG. 3B is a cross-sectional view taken along the line A-A' in FIG. 3A.
Figure 4A:
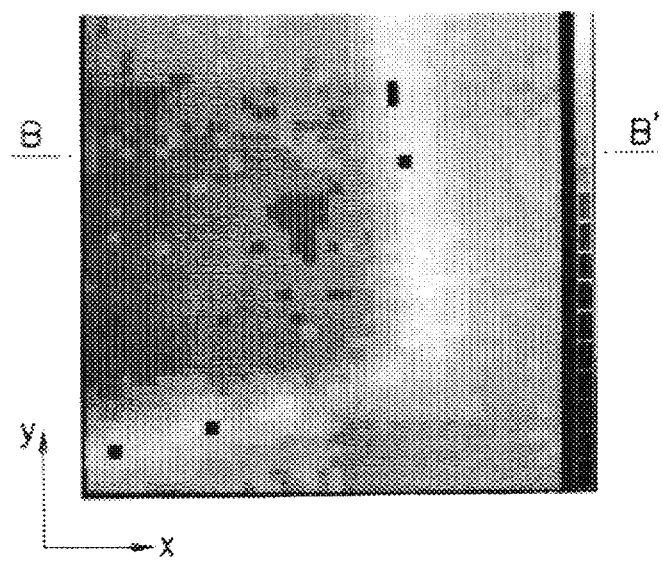
FIG. 4A is a two-dimensional photoacoustic image (phase image) of a sample having a surface crack.
Figure 4B:
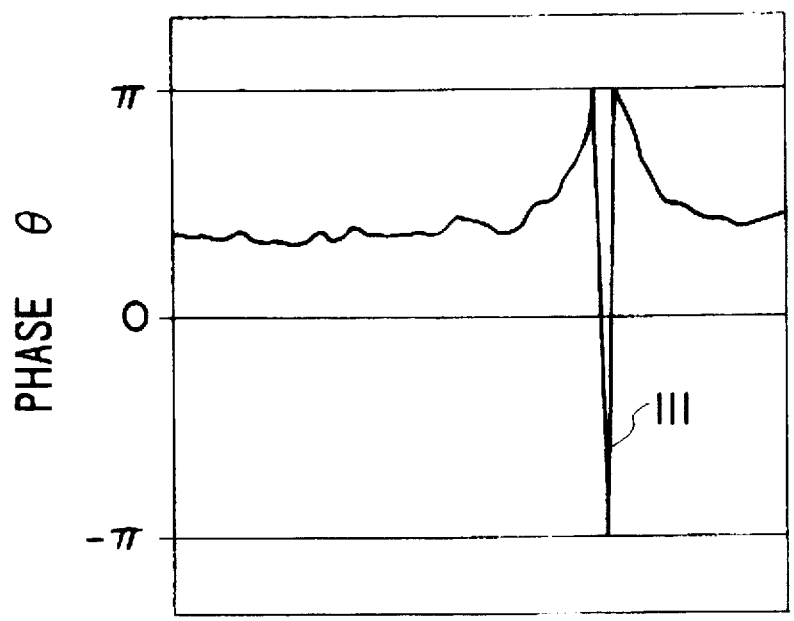
FIG. 4B is a phase signal diagram taken along the line B-B' in FIG. 4A.
Figure 40A:
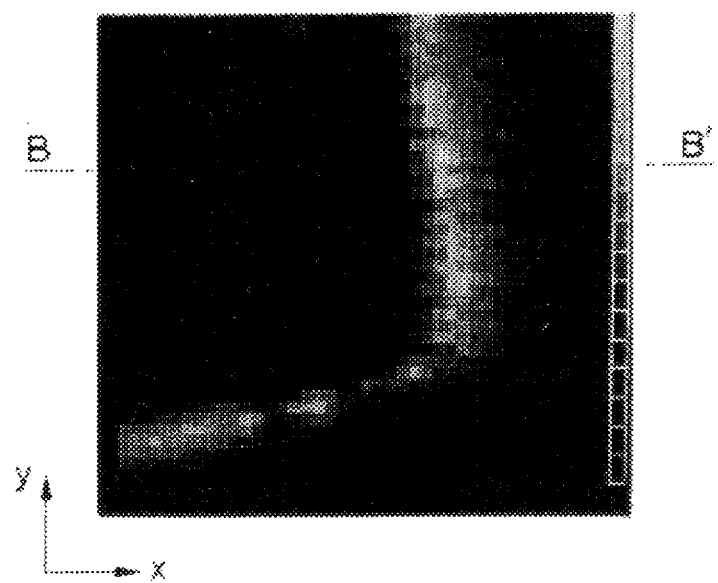
FIG. 40A is a two-dimensional photoacoustic image (phase image) after a phase jump correction has been made on the photoacoustic signal (phase signal)
Figure 40B:
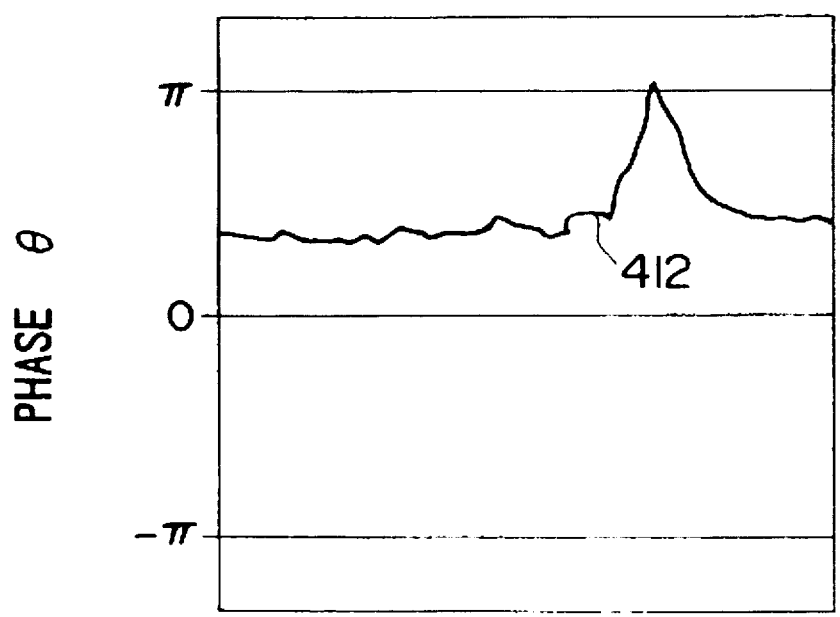
FIG. 40B is a diagram showing a phase shift signal taken along the line B-B' in FIG. 40A.
Figure 41:
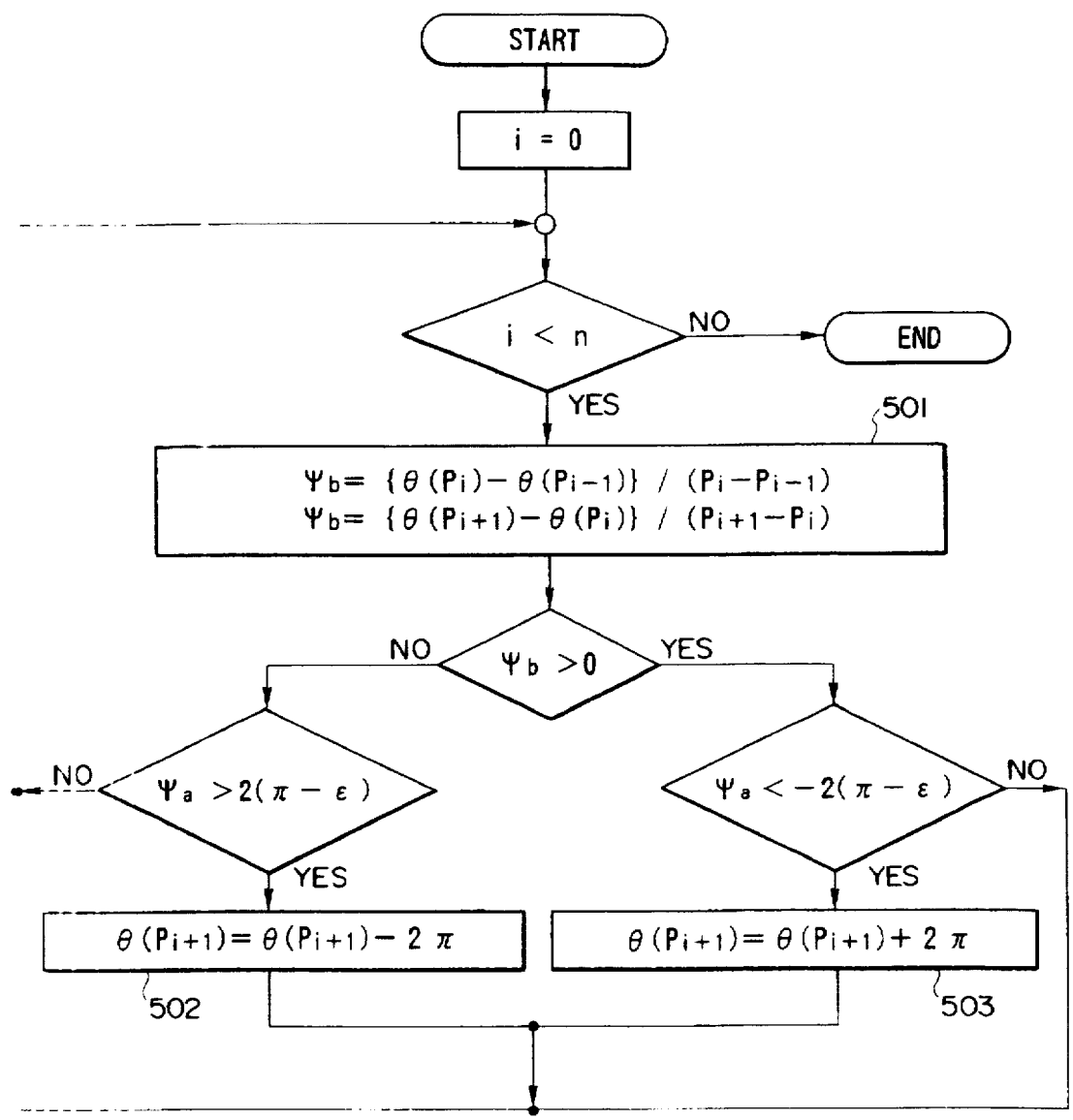
FIG. 41 is a flowchart showing another arrangement of the phase jump presence detecting and phase jump correcting process.
Figure 42A:
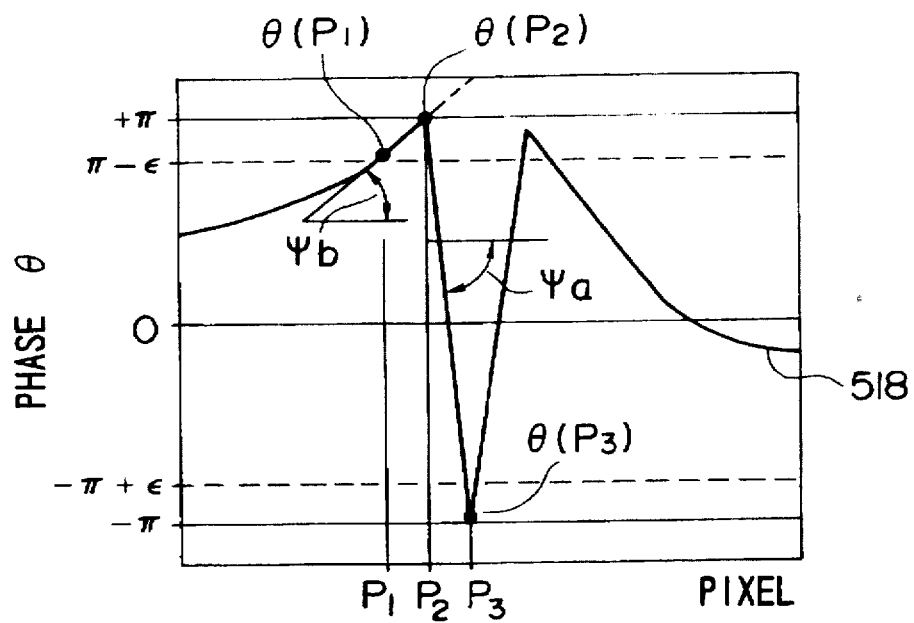
FIGS. 42A and 42B are diagrams showing means for correcting a phase jump of the photoacoustic signal according to FIG. 41.
Figure 42B:
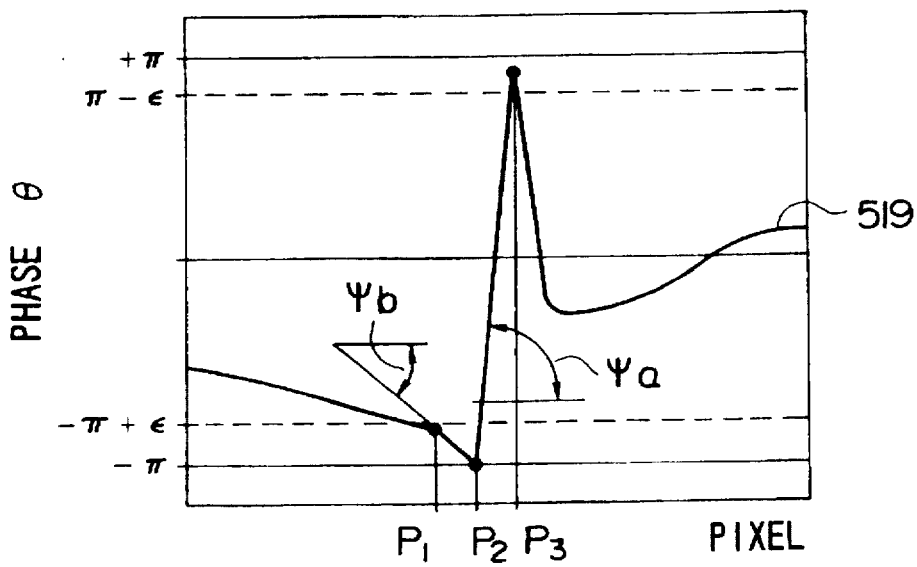

FIG. 40A shows a phase image after a phase jump correction has been done on the phase image shown in FIG. 38A described. FIG. 40B is a view of the phase shift signal 412 taken along the line B-B' in FIG. 40A, with the phase shift signal 111 in FIG. 4B shown for comparison. It will be understood that the sharp change of phase caused by the crack is shown correctly.

In the above description, a case is assumed in which a phase jump correction process on the phase signal for one line in the x-direction in the two-dimensional phase image is executed line after line simultaneously with detection of a phase signal. In actual processing, the phase jump correction process can be expanded to the y-direction based on the partial two-dimensional phase signal stored tentatively until then. Also, it is possible to simultaneously perform the phase jump correction process in the x- and y-directions on the tentatively stored two-dimensional phase signal after all the phase signal is detected.

As has been described, in the photoacoustic signal detection method according to the present invention, as the abnormality of the phase signal caused by a phase jump of the photoacoustic signal, or in other words, omission of phase information is eliminated, it becomes possible to detect a photoacoustic signal steadily and securely, and information relative to the subsurface of the sample can be obtained with high accuracy. Moreover, the phase jump correction process for the photoacoustic signal is performed on the detected phase signal, so that this process can be executed readily only by a partial addition of process function to the signal processing system without altering the optical system of the photoacoustic signal processing apparatus of the prior art.

In the phase jump detection and correction process described above, the phase jump detection and the subsequent phase jump correction are carried out according to a change of the sign of the phase signal between the two adjacent pixels and a difference in the phase signal between the two pixels. Besides this, there is another possible method of phase jump detection and correction. This method is to let the processor 274 execute the phase jump detection and correction process, shown in FIG. 41, to the phase image, shown in FIG. 38A, which was processed by the processor 274. In this principle of this phase jump detection and correction process, a characteristic is utilized that generally, the phase gradient changes suddenly from plus to minus or minus to plus in the neighborhood of the pixel at which a phase jump occurs. More specifically, in the phase shift signal 518 shown in FIG. 42A, for example, for the phase signals θ ($P_1$), θ ($P_2$) and θ ($P_3$) at the three consecutive pixels on the same straight line, the phase gradients $\psi_b$ and $\psi_a$ respectively between the pixels $P_1$ and $P_2$ and between the pixels $P_2$ and $P_3$ are calculated (to be more precise, the phase gradients $\psi_b$ and $\psi_a$ are obtained respectively as tan $\psi_b$ and tan $\psi_a$). Then, a decision is made whether $\psi_b$ is plus or minus. If $\psi_b$ is plus and $\psi_a$<−2 (ε−π) (ε is defined as of the same character as the one mentioned above, in this embodiment the constant ε is set at π/6, and a pitch between pixels $P_{i+1}$ and $P_i$ is assumed to be one pixel), a decision is made that a phase jump has occurred, and accordingly, 2 is added to θ ($P_2$). In this way, a phase jump correction is executed. Likewise, for the phase signal 519 shown in FIG. 42B, from the fact that $\psi_b$ is minus and $\theta_a$>2(π−ε), a decision is made that a phase jump has occurred, and a phase jump correction is made by adding −2π to θ ($P_3$). In the foregoing description, the phase gradients $\psi_a$ and $\psi_b$ are calculated between two adjacent pixels, but it is possible to calculate a phase gradient between two pixels separated more than two pixels and perform a phase jump correction according to the calculation result.

Figure 43B:
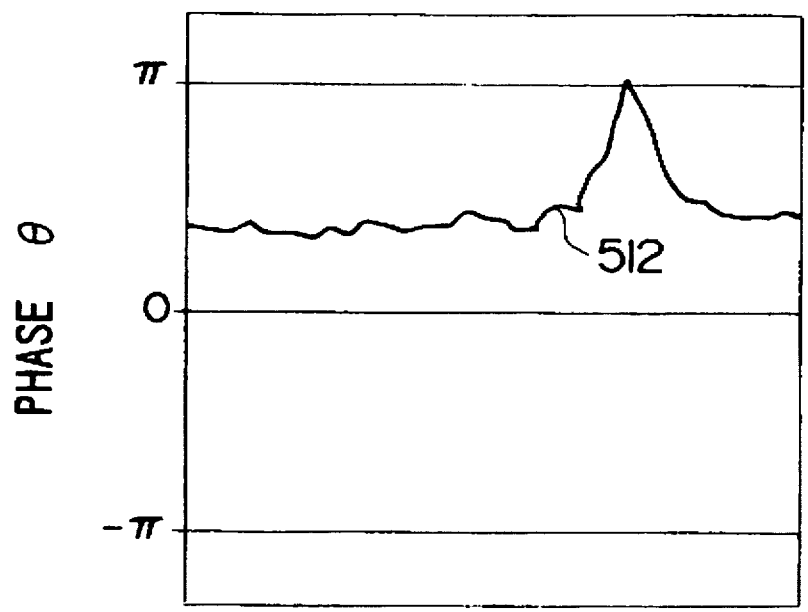
FIG. 43B is a diagram showing a phase signal taken along the line B-B' in FIG. 43A.

FIG. 43A shows a phase image after a phase jump correction process has been executed by the phase jump detection and correction process to the phase image shown in FIG. 38A mentioned above. FIG. 43B shows the phase signal 512 taken along the line B-B' in FIG. 43A along with the phase signal 111 shown in FIG. 38B for comparison. As can be seen from these figures, the sharp change in phase caused by a crack is correctly shown.

As mentioned above, by the phase jump detection and correction process by the other method, too, the deviation of the phase signal due to a phase jump of the photoacoustic signal, that is to say, an omission of phase information can be eliminated. Therefore, the photoacoustic signal can be detected steadily and securely and information as to the inside of the sample can be obtained with high accuracy. Furthermore, a phase jump correction process for the photoacoustic signal is carried out to the phase signal detected, and therefore, can be executed readily by only a partial addition of process function to the signal processing system without making alterations to the optical system in the photoacoustic signal detection apparatus of the prior art.

In the foregoing description, cases are assumed in which the phase jump correction process on the phase shift signal for every line in the x-direction in a two-dimensional phase image is executed line after line simultaneously with the phase shift signal detection process. In actual processing, however, the phase jump correction process can be expanded also to the y-direction based on a partial two-dimensional phase shift signal stored temporarily. It is also possible to perform the phase jump correction process simultaneously in the x- and the y-directions to the temporarily stored two-dimensional phase shift signal after all the phase shift signal is detected. Furthermore, it is possible to simultaneously execute this phase jump correction process in combination with the phase jump detection and correction process shown in FIG. 33. Moreover, in making a decision on the presence or absence of a phase jump, it is possible to judge whether a phase jump exists not only according to criteria based on a change of the sign of the phase shift signal between two adjacent pixels and a difference in the phase shift signal between those two pixels, but also according to criteria of a combination of the degree of the above-mentioned phase shift gradients and the signs (polarities) of the phase shift gradients with the above-mentioned criteria, or according to a logical product of all those criteria. On the other hand, in the phase jump correction process, it is possible to decide whether to add 2π or −2π according to a criteria of a combination of the sign (polarity) of a difference in phase between two adjacent pixels and the signs (polarities) of the above-mentioned phase shift gradients.

Description will be made of a photoacoustic signal detection apparatus in another structure to which the present invention can be applied.

Figure 44:
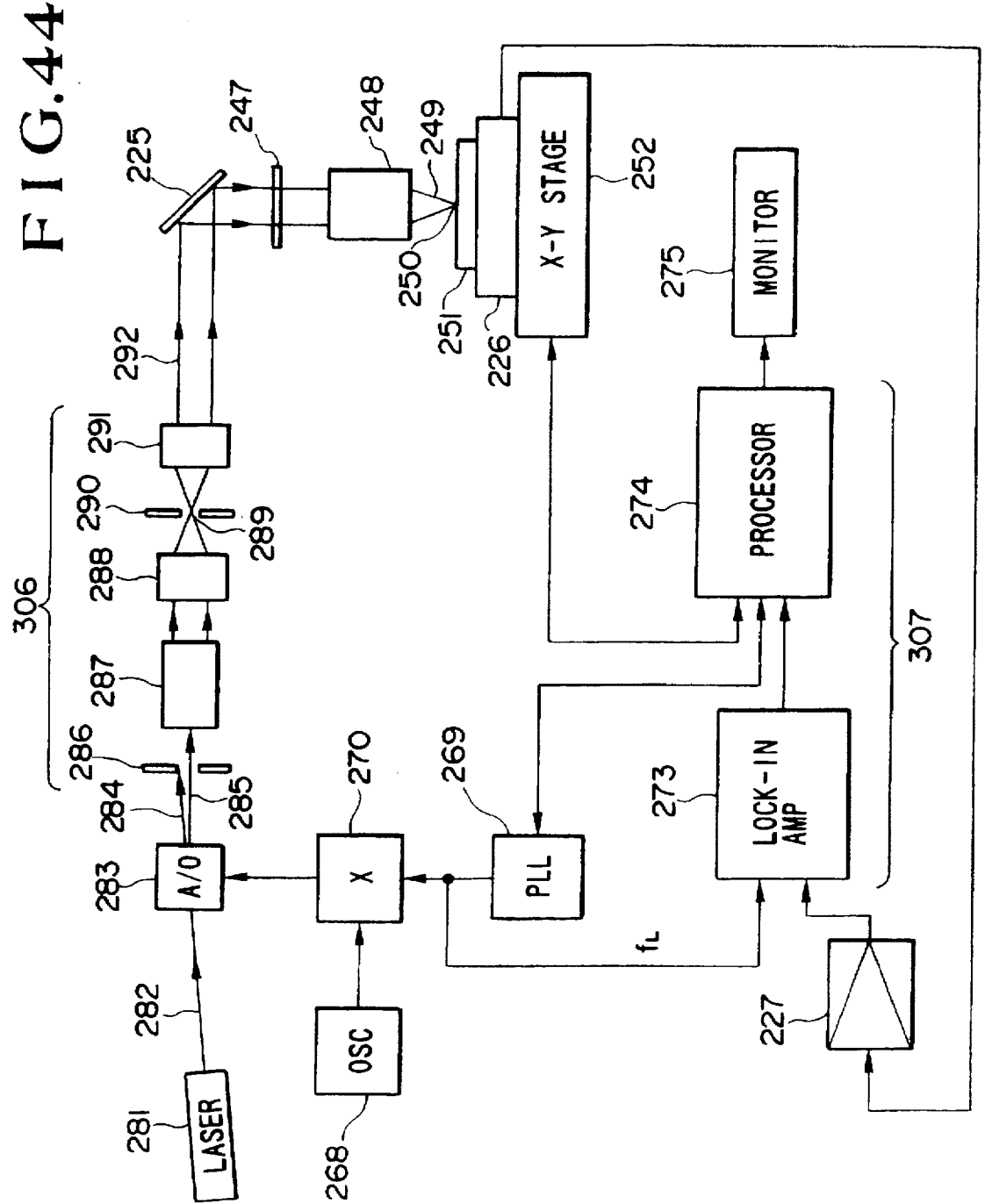
FIG. 44 is a diagram of another structural example of the photoacoustic signal detection apparatus.

FIG. 44 shows the structure, a substantial difference of which from the one shown in FIG. 34 is that a PZT (piezoelectric) element 226 is provided newly below the sample 251 for detecting a photoacoustic signal in place of the above-mentioned Mach-Zehnder interferometric optical system. The structure of an excitation optical system 306 is the same as the one shown in FIG. 34, expecting that a mirror 225 is used in place of the dichroic prism 293. An output signal from the PZT element 226 contains information about the amplitude A and the phase θ of the minute displacements at the surface of the sample 251 at the intensity-modulated frequency $f_L$. These items of information are obtained by a signal processing system 307. As illustrated, from the output signal from the PZT element 226, the lock-in amplifier 273 obtains through the pre-amplifier 227 the amplitude and phase of the frequency component of $f_L$ by using the sine wave of frequency $f_L$ from the oscillator 269 as a reference signal. From those amplitude and phase, the processor 274 obtains the amplitude A and the phase θ corresponding to the minute displacements at the surface of the sample 251. The amplitude A and the phase θ contain information relative to thermoelastic properties in the heat diffusion region ($V_{th}$) defined at the intensity-modulated frequency $f_L$. Therefore, if there is an internal defect such as a crack in the heat diffusion region $V_{th}$, the amplitude A and the phase θ vary, and from these variations, the presence of an internal defect is known. In this process, the laser-lightirradiated positions on the sample 251 are controlled through the X-Y stage by the processor 274 which specifies one position after another as the position whose data is to be updated, and the real laser-light-irradiated can be known by the processor 274 from a position detection signal from the X-Y stage 252. If an arrangement is made such that the processor 274 processes the intensity-modulated frequency component from the lock-in amplifier 273 in conjunction with the real laser-light-irradiated position each time the laser light is irradiated to the sample 251, then the photoacoustic signal corresponding to the real laser-light-irradiated positions can be obtained so as to output a two-dimensional photoacoustic image on a display 275. In this case, the processor 274 performs a phase jump detection and correction process when a phase jump exists, in addition to its general process to obtain the photoacoustic image.

Figure 32:
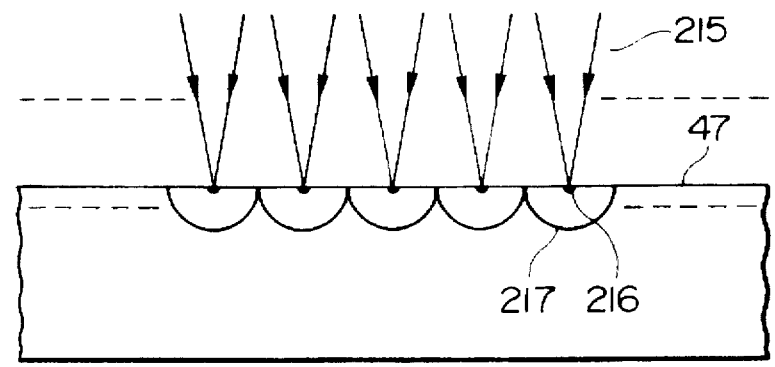
FIG. 32 is a diagram showing heat diffusion regions produced by the respective spot beams in the fourth embodiment.

The above-mentioned one other structure can be applied to photoacoustic detection apparatuses which use a stripe beam in the embodiments shown up to FIG. 32. If the structure using the excitation oscillation optical system and the PZT element shown in FIG. 44 is adopted in a photoacoustic detection apparatus using the above-mentioned stripe beam as the excitation light, then an advantage is obtained that the probe light and the interferometric optical system can be done away with, and therefore, the structure of the apparatus can be simplified.

Another preferred embodiment of the present invention will be described with reference to FIGS. 45 to 53A, B.

The use of a point scanning process and a lock-in amplifier, i.e., the use of a synchronous detection process, is a principal factor in the low detecting speed of the conventional method. An object of the present invention is to enhance the detecting speed significantly, securing a sensitivity equal to that of the conventional method. Basic concept and fundamental principle of enhancing detecting speed will be described prior to the description of the preferred embodiment.

Figure 46:
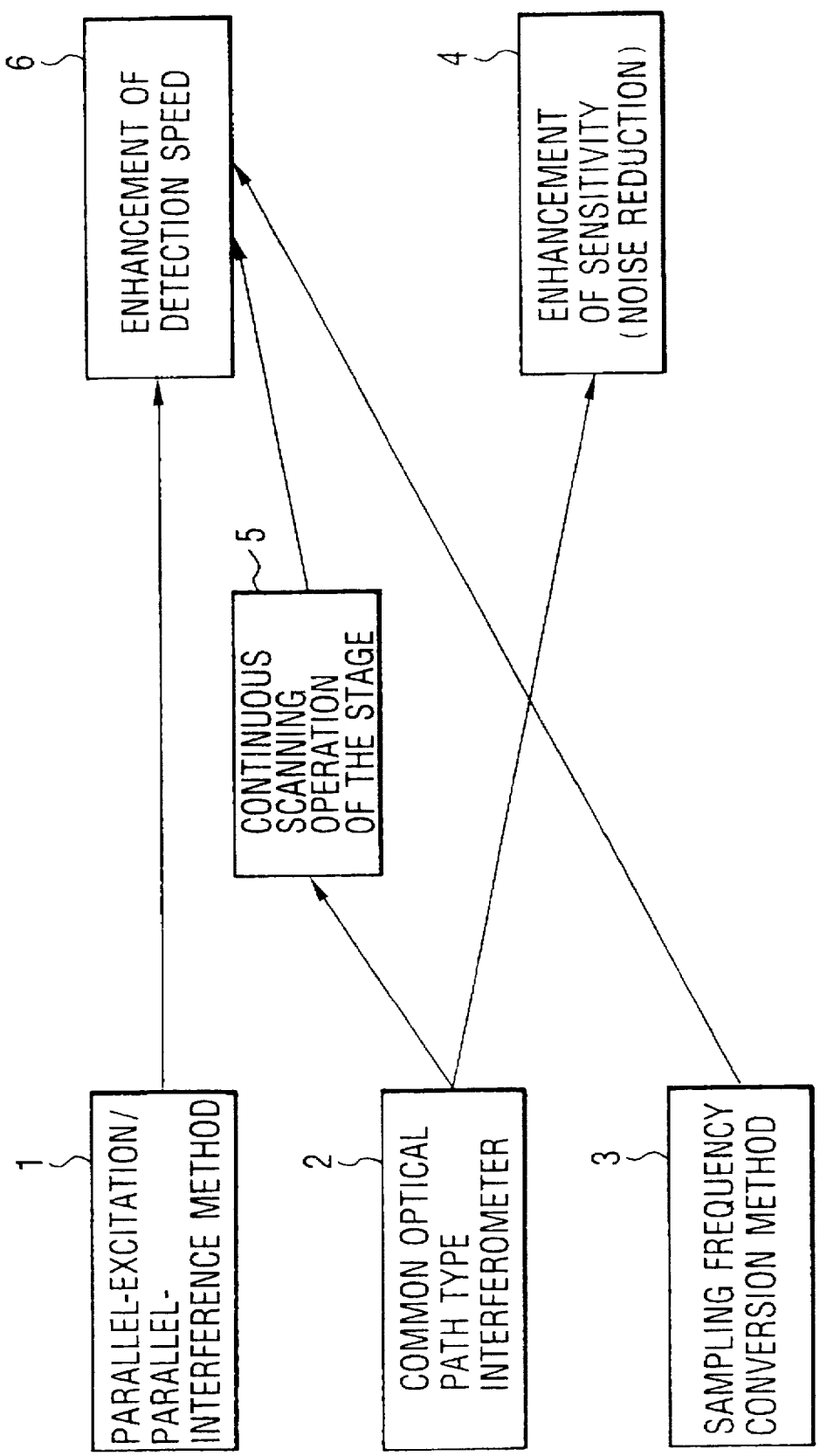
FIG. 46 is a block diagram of assistance in explaining the basic concept of enhancing detecting speed.

FIG. 46 is a block diagram of assistance in explaining the basic concept. We propose a parallel-excitation/parallel-interference method employing a flat beam to excite a plurality of points on a specimen simultaneously for detection. The parallel-interference method is carried out by a common path interferometer to reduce significantly noise component included in the interference signal due to air fluctuation and vibrations of the stage. The common path interferometer enables the stage to be moved continuously for continuous scanning, which further enhances the measuring speed.

The parallel interference method needs a one-dimensional sensor comprising a plurality of light receiving elements respectively corresponding to measuring points for the detection of interference light and is unable to apply a detection signal directly to a lock-in amplifier. Accordingly, we propose a new thermal expansion component extracting method and a sampling frequency conversion method to substitute the lock-in amplifier, i.e., synchronous detection. This method uses the noise component reducing effect of a common path interferometer to curtail detection time needed for the detection of one point by reducing the amount of data to be used for signal processing.

Figure 45:
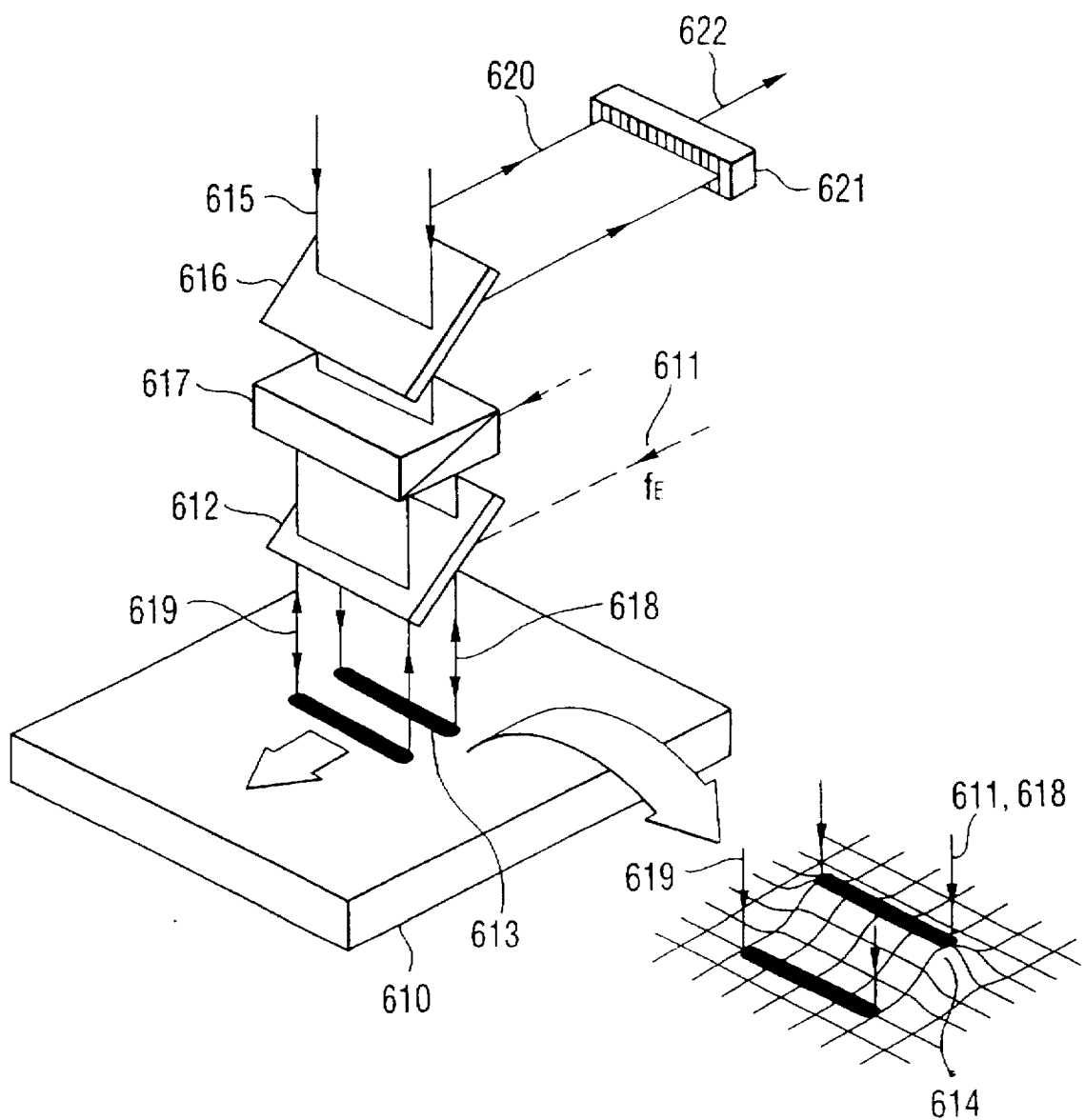
FIG. 45 is a perspective view of assistance in explaining the fundamental principle of a parallel-excitation/parallel-interference method in accordance with the present invention.

First, the principle of the parallel-excitation/parallel-interference method will be described. Referring to FIG. 45, a light beam 611 intensity-modulated at a frequency $f_E$ is reflected by a dichroic mirror 612 so that the light beam is focused in a straight light line on the surface of a specimen 610 to excite a plurality of continuous points simultaneously; consequently, a straight periodic thermal expansion displacement 614 occurs in the surface of the specimen 610. The amplitude and the phase of the thermal expansion displacement 614 at each point are dependent on the thermal conductivity distributions on the surface and the interior of the specimen 610. A flat probe laser beam 618 separated from a laser beam 615 by a birefringence element 617 is projected through a beam splitter 616 and the dichroic mirror 612 on the specimen 610, and a reference light beam 619 of a frequency slightly different from that of the probe laser beam 618 is projected through the beam splitter 616 and the dichroic mirror 612 on the specimen 610 at a position near the position at which the probe laser beam 618 falls. The reflected reference light beam 619 reflected by the linear thermal expansion displacement 614 is superposed as a one-dimensional optical phase distribution on the reflected probe laser beam 618 reflected by an excited part 613. The reflected light beams are combined for heterodyne interference by the birefringence element 617, and the optical phase distribution is detected by a one-dimensional CCD sensor 621 as a one-dimensional spatial distribution of heterodyne interference light 620.

The use of the common path interferometer, in which the probe laser beam 618 and the reference light beam 619 travel along the substantially the same optical paths, cancels out an optical phase difference attributable to air fluctuation in the optical paths and vibrations of the stage during movement for scanning, so that the variation of the interference signal can be greatly reduced and the continuous scanning movement of the stage is possible.

A sampling frequency conversion method will be described hereinafter. Suppose that the amplitude and the phase of the thermal expansion displacement 614 at one point on the surface of the specimen 610 are A and θ, respectively, the wavelength of the probe laser beam 618 is λ, the intensity of the reflected probe laser beam 618 is $I_S$, the intensity of the reflected reference light beam 619 is $I_r$, the frequency difference between the probe laser beam 618 and the reference light beam 619, i.e., the frequency of a heterodyne beat, is $f_B$ and the phase difference between the optical paths attributable to irregularities in the surface of the specimen 610 is φ. Generally, the thermal expansion amplitude A is on the order of sub-nanometers. Therefore, A<<λ when λ=632.8 nm, and the intensity I(t) of the heterodyne interference light 620 incident on one pixel of the one-dimensional CCD sensor 621 can be approximated by expression (20).

$$I(t) = (I_s + I_r) + 2\sqrt{I_s I_r} \ \{\cos(2\pi f_B t + \phi) + \frac{2\pi}{\lambda} A\sin[2\pi(f_B + f_E)t + \phi + \theta] + \frac{2\lambda}{\lambda} A\sin[2\pi(f_B - f_E)t + \phi - \theta]\}$$

Expression (20)

In expression (20), the first term represents a dc component, the second term represents the carrier component of the heterodyne beat frequency $f_B$, the third term represents the sideband components of the frequency $f_B+f_E$ having information about the thermal expansion amplitude A and the phase θ, and the fourth term represents the sideband component of the frequency $f_B-f_E$ having information about the amplitude A and the phase θ. The third or the fourth term represents a necessary information component.

Figure 47:
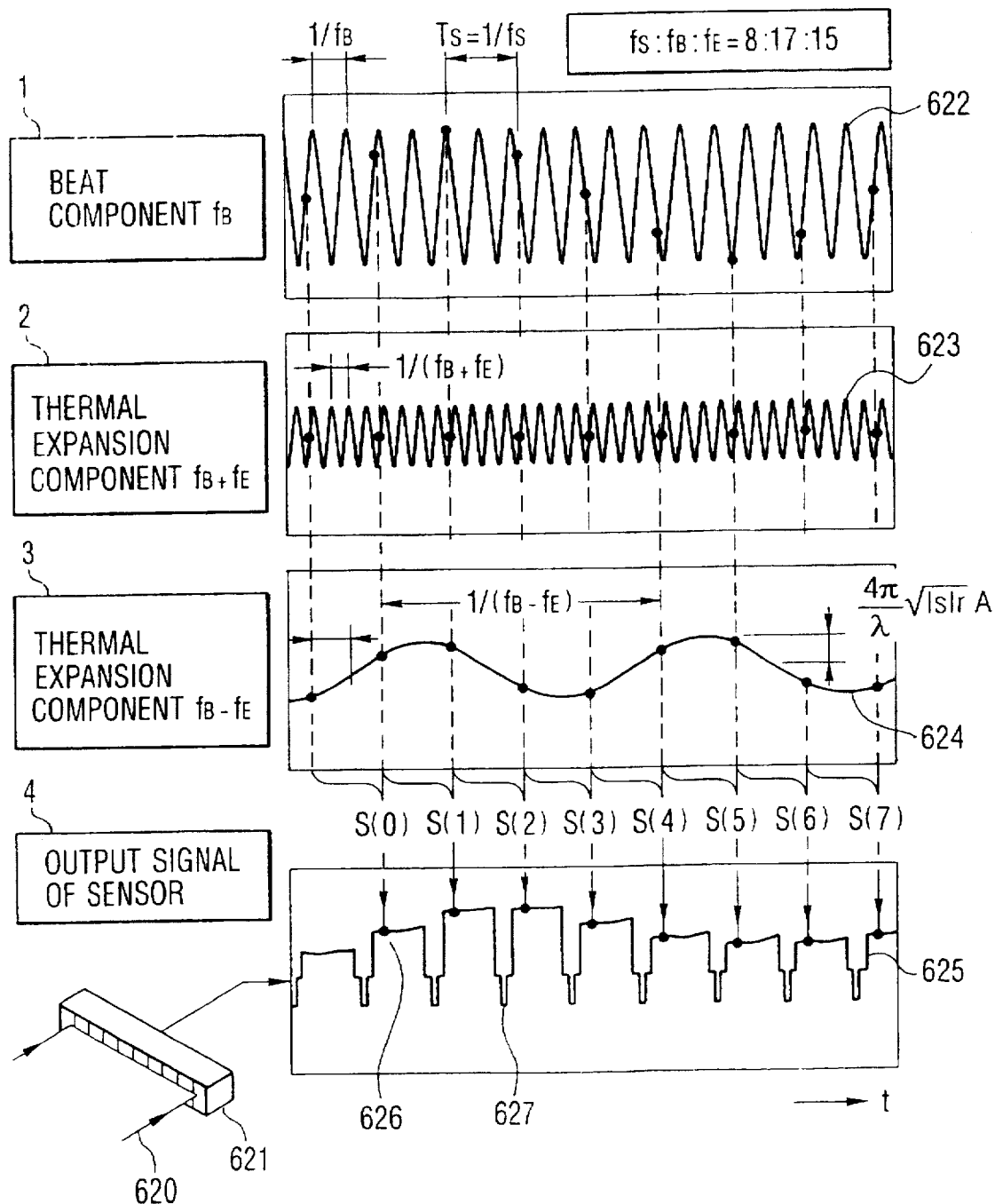
FIG. 47 is a waveform chart of assistance in explaining the fundamental principle of a sampling frequency conversion method.

As shown in FIG. 47, the interference light 620 is integrated at a fixed period by the storage effect of the CCD sensor 621. Each pixel provides an output interference signal 625 during line scanning. Therefore the thermal expansion amplitude A and the phase θ cannot be extracted by directly giving the output interference signals 625 to a lock-in amplifier for synchronous detection.

Therefore, the relation between the storage frequency $f_S$, the beat frequency $f_B$ and the intensity modulating frequency $f_E$ is determined by using the storage effect of the CCD sensor 621 so as to meet a ratio of 8p:8pu+1:8pv−1 or 8p:8pu−1:8pv+1, where p, u and v are integers other than zero. For example, when p=1, v=u=2, $f_S$:$f_B$:$f_E$=8:17:15, and a heterodyne interference signals S(i) provided by a specific pixel in the i-th line scanning is expressed by expression (21) by the storage (integration) effect of the sensor and sampling effect for one line scanning.

$$S(i) = \int_{iT_S}^{(i+1)T_S} I(t)dt = (I_s + I_r)T_S + \quad \text{Expression (21)}$$

$$2\sqrt{I_s I_r} \left[ \frac{1}{\pi f_B} \sin\frac{\pi}{8} \cos\left( i\frac{\pi}{4} - \frac{\pi}{8} + \phi \right) + \right.$$

$$\left. \frac{2A}{\lambda(f_B - f_E)} \sin\frac{\pi}{4} \sin\left( i\frac{\pi}{2} - \frac{\pi}{4} + \phi - \theta \right) \right]$$

where $T_s = 1/f_S$ (storage time)    Expression (22)

As shown in FIG. 47, since $f_B+f_E$ is an integral multiple of $f_S$, the thermal expansion component 623 is integrated and under-sampled at the period $1/f_S$ (plots indicated by solid circle in FIG. 47) and removed from the output signal. Likewise, the beat component 622 of the frequency $f_B$ is converted into line scanning i, i.e., a component of ⅛ the frequency for the period $1/f_S$, and the thermal expansion component 624 of $f_B-f_E$ is converted into a component of ¼ the frequency.

The principle of extracting the thermal expansion component using Fourier coefficients will be explained hereinafter. The discrete Fourier series expansion of a periodic signal and the Fourier coefficients of the discrete Fourier series expansion are expressed by expressions (23), (24) and (25).

$$S(i) = \frac{a_0}{2} + \sum_{n=1}^{N/2} \left( a_n \cos\frac{2\pi n i}{N} + b_n \sin\frac{2\pi n i}{N} \right) \quad \text{Expression (23)}$$

$$a_n = \frac{2}{N} \sum_{i=0}^{N-1} S(i)\cos\frac{2\pi n i}{N} \quad \text{Expression (24)}$$

$$b_n = \frac{2}{N} \sum_{i=0}^{N-1} S(i)\sin\frac{2\pi n i}{N} \quad \text{Expression (25)}$$

where N is data number.

As is obvious from expressions (24) and (25), the Fourier coefficients $a_{N/4}$ and $b_{N/4}$ for a component of of ¼ the frequency, i.e., the integrated thermal expansion component of $f_B-f_E$ can be determined by simple addition and subtraction expressed by expressions (26) and (27) and can be easily separated and extracted from the interference signal.

$$a_{N/4} = \frac{2}{N} \{S(0) - S(2) + S(4) - S(6) + \ldots \} \quad \text{Expression (26)}$$

$$b_{N/4} = \frac{2}{N} \{S(1) - S(3) + S(5) - S(7) + \ldots \} \quad \text{Expression (27)}$$

Likewise, the Fourier coefficients $a_{N/8}$ and $b_{N/8}$ for a component of ⅛ the frequency, i.e., the integrated beat component of $f_B$, can be expressed by expressions (28) and (29).

$$a_{N/8} = \frac{2}{N} \left\{ S(0) + \frac{S(1)}{\sqrt{2}} - \frac{S(3)}{\sqrt{2}} - S(4) - \ldots \right\} \quad \text{Expression (28)}$$

$$b_{N/8} = \frac{2}{N} \left\{ \frac{S(1)}{\sqrt{2}} + S(2) + \frac{S(3)}{\sqrt{2}} - \frac{S(5)}{\sqrt{2}} - \ldots \right\} \quad \text{Expression (29)}$$

The amplitude A and the phase θ of the thermal expansion displacement can be obtained by substituting the expressions into expressions (30) and (31).

$$A = \frac{\lambda(f_B - f_E)}{4\sqrt{I_s I_r} \sin\pi/4} \sqrt{a_{N/4}^2 + b_{N/4}^2} \quad \text{Expression (30)}$$

$$\theta = -\tan^{-1}\frac{b_{N/4}}{a_{N/4}} + \tan^{-1}\frac{b_{N/8}}{a_{N/8}} + \frac{\pi}{8} \quad \text{Expression (31)}$$

The denominator of expression (30) includes the respective intensities $I_S$ and $I_r$ of the reflected probe laser beam 618 and the reference light beam 619 to correct the effect of the reflectance distribution on the surface of the specimen 610. The second term of expression (31) is a correction term for correcting a phase change caused by irregularities in the surface of the sample 610 obtained from the beat component. Thus, the thermal expansion component can be accurately extracted from the interference signal through simple operations for addition and subtraction by converting the beat component and the thermal expansion component by sampling frequency conversion so that the frequency ratio is 1:2, which is the significant feature of the processing method. A signal processing circuit, which will be described later, executes operations for obtaining the Fourier coefficients expressed by expressions (26) to (29) in a real-time mode by combining operations for the sequential writing of the output signal 25 of the CCD sensor 21 in and reading the same from a one-dimensional storage and operations for addition and subtraction.

A photothermal displacement image detecting apparatus in a preferred embodiment according to the present invention will be described with reference to FIGS. 48 to 53A, B.

Figure 48:
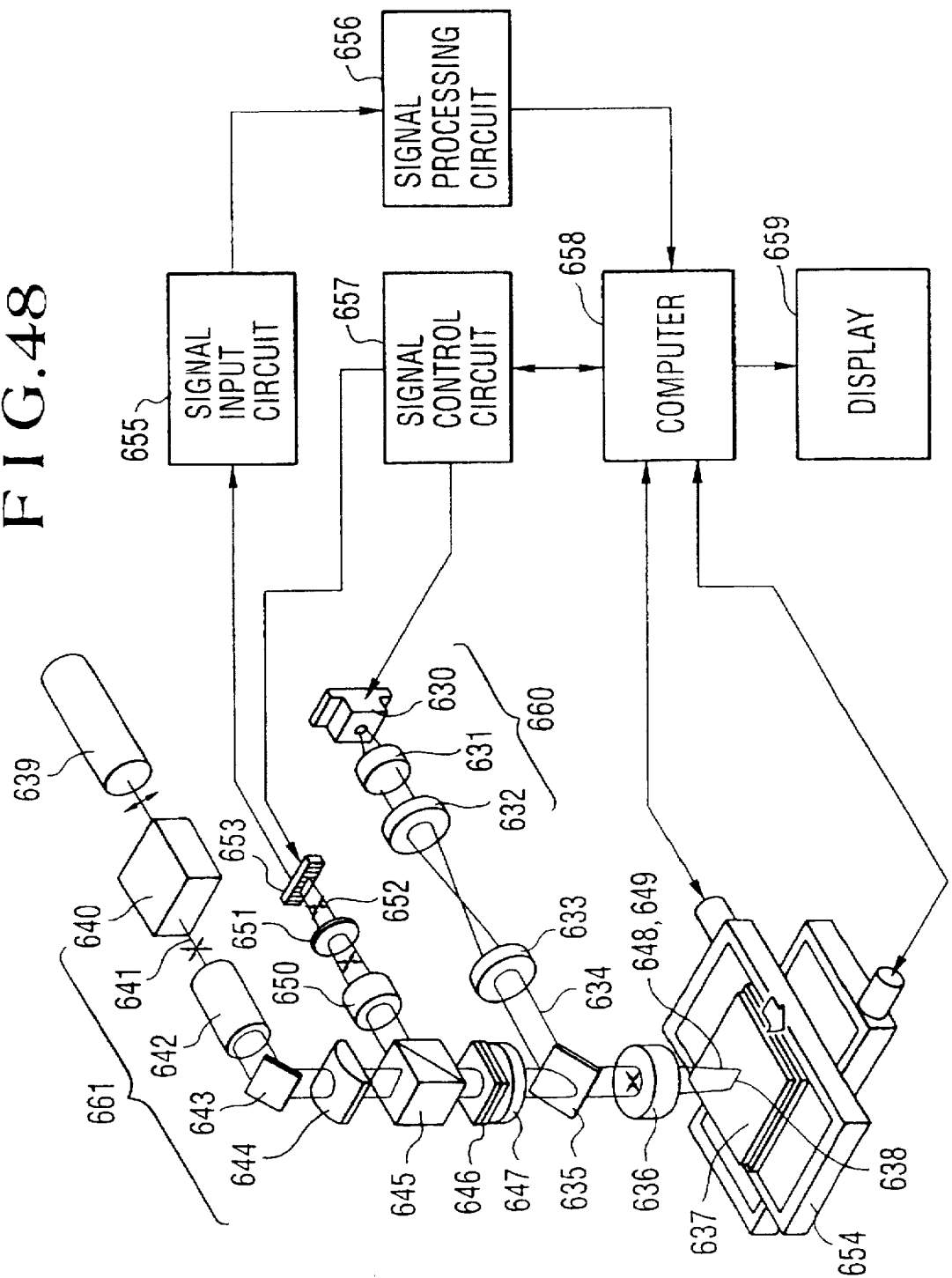
FIG. 48 is a diagrammatic perspective view of a photothermal displacement image detecting apparatus in a preferred embodiment according to the present invention.
Figure 49:
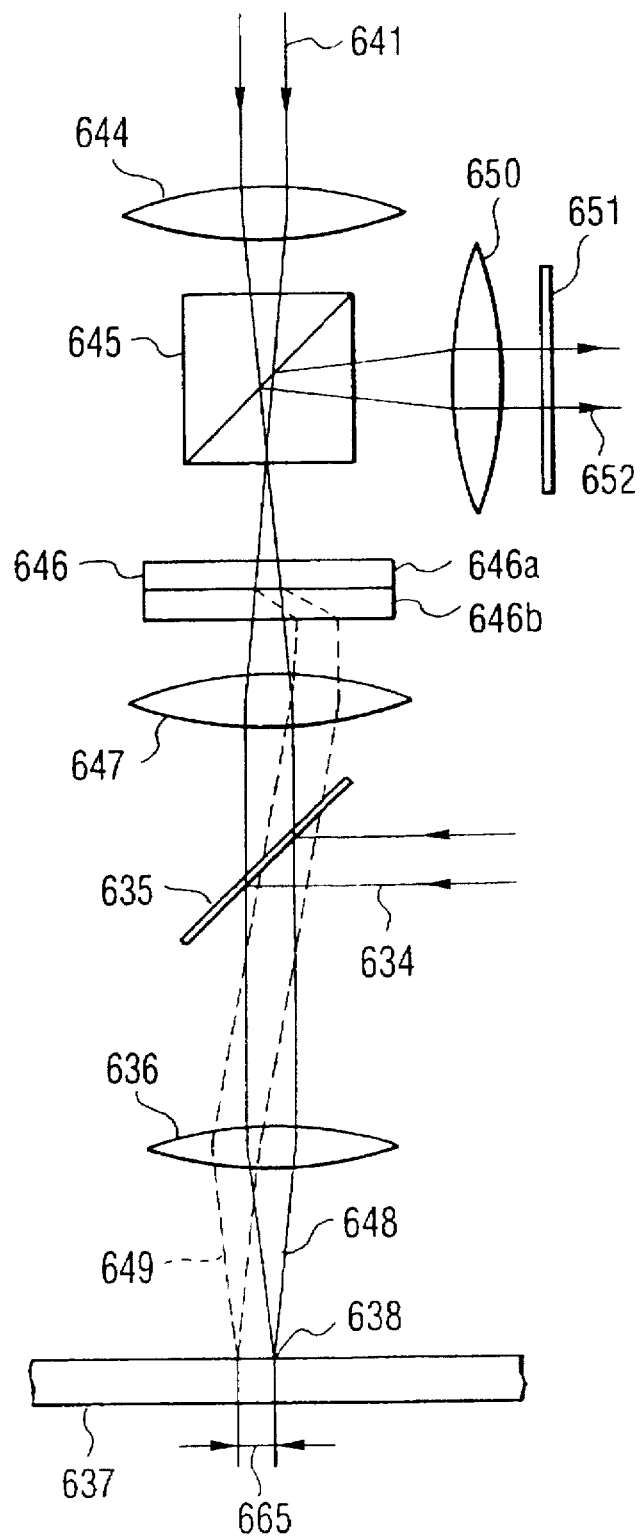
FIG. 49 is a diagrammatic view of a common optical path type interferometer included in the photothermal displacement image detecting apparatus.
Figure 50:
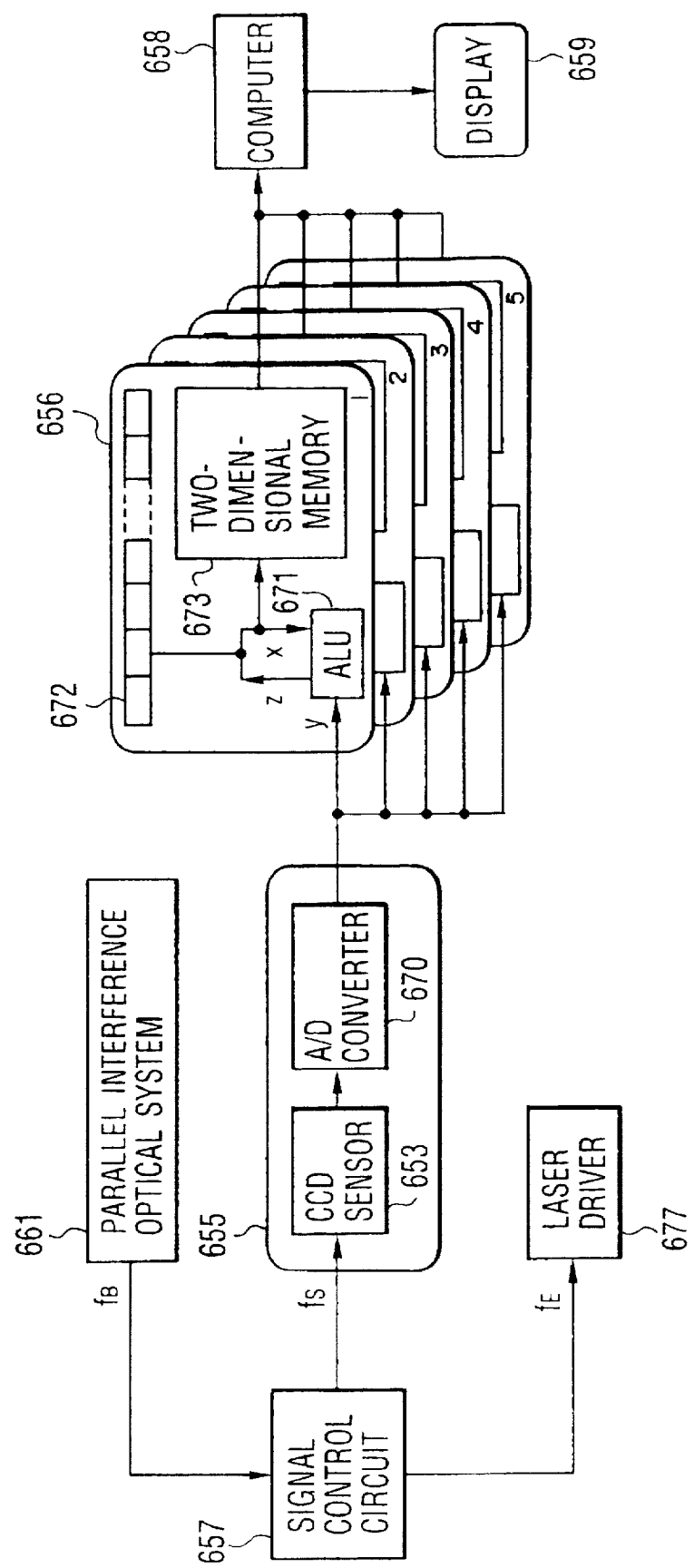
FIG. 50 is a block diagram of a signal input circuit, a signal processing circuit and a signal control circuit included in the photothermal displacement image detecting apparatus.

Referring to FIG. 48, the photothermal displacement image detecting apparatus comprises an optical unit comprising a parallel excitation optical system 660 and a parallel interference optical system 661, a signal input circuit 655, signal processing circuits 656, a signal control circuit 657, a computer 658, a display 659, and a stage system 654.

A 2 W output high-output semiconductor laser 630 that emits a 799 nm wavelength flat laser beam of 1.5 μm×200 μm is employed as an excitation light source. A driving current is modulated by a rectangular wave of the frequency $f_E$ for the direct intensity modulation of a light emission pattern.

A frequency-stabilized He—Ne laser 639 that emits a laser beam of 632.8 nm in wavelength is employed as a probe light source. A linearly polarized beam emitted by the laser 639 is divided into two polarized component beams 641 respectively having planes of polarization perpendicular to each other by an optical frequency shifter 640. The two polarized component beams 641 are expanded by a beam expander 642, are reflected by a mirror 643, travel through a cylindrical lens 644 and a beam splitter 645, are separated in parallel by the birefringence characteristic of a Savart plate 646 consisting of a pair of calcite plates 646a and 646b, and travel through a relay lens 647 and a dichroic mirror 635. Then, one of the polarized component beams 641 is focused as a flat probe light beam 648 on an excitation part 38 and the other polarized component beam 641 is focused in a flat reference light beam 649 on a part near the excitation part 638 by an objective 636.

The reflected probe light beam 648 and the reflected reference light beam 649 are recombined by the Savart plate 646, are reflected by the dichroic mirror 645, travel through a focusing lens 650, and are caused to interfere with each other for heterodyne polarization interference by a polarizing plate 651. Consequently, a linear light phase distribution due to thermal expansion displacement is detected as a one-dimensional spatial distribution of the interference light 652 by a CCD sensor 653 comprising 256 pixels each of 13 µm². A detection field of about 166 µm is formed on a specimen 637 by the 20× objective 636.

For example, when the specimen is a silicon wafer and the modulating frequency $f_E$ is 88.235 kHz, the interval between the probe light beam 648 and the reference light beam 649 is 20 µm, which is greater than a thermal diffusion length of 18 µm.

FIG. 48 shows the general configuration of the signal input circuit 655, the signal processing circuits 656 and the signal control circuit 657.

The signal input circuit 655 converts the interference signal provided by the one-dimensional CCD sensor 653 into 14-bit digital data an A/D converter 670 by A/D conversion after offset gain adjustment, not shown.

Each signal processing circuit 656 comprises an ALU (arithmetic logic unit) 671, a one-dimensional memory 672, a two-dimensional memory 673 and a computer 658. The signal processing circuits 656 repeat arithmetical operations using expressions (26) to (29) for interference signals provided by the CCD sensor 653 and stores the results of arithmetic operations in the two-dimensional memory 673.

The ALU 671 executes an addition: z=x+y or a subtraction: z=x−y, where x is data read from the one-dimensional memory 672 corresponding to the 256 pixels of the CCD sensor 653 and y is the interference signal provided by the signal input circuit 655, and stores the result z of the arithmetical operation in the same address in the one-dimensional memory 672. After the foregoing operations have been repeated, the contents of the one-dimensional memory 672 is written in the two-dimensional memory 673. The line data corresponds to the data of one line in the measuring area obtained by arithmetical operations. These operations are executed while the stage 654 is being moved continuously for scanning to complete arithmetical operations for the two-dimensional area.

The five signal processing circuits 656 execute five kinds of arithmetical operations, i.e., operations using expressions (26) to (29) and addition for calculating the dc component, in parallel. After the arithmetical operations have been completed, the computer 658 calculates data representing a two-dimensional image of a thermal expansion amplitude A and a phase θ using the data representing the Fourier coefficients and data representing the dc components and stored in the two-dimensional memories 673, and the display 659 displays the calculated two-dimensional image.

The ability to separate and extract the minute thermal expansion component depends on the accuracy in setting the frequencies meeting the ratio of 8p:8pu+1:8pv−1 or 8p:8pu−1:8pv+1, where p, u and v are integers other than zero. The signal control circuit 657 unifies the generation of control signals and employs a PLL (phase-locked loop) circuit in generating control signals to stabilize the frequencies and the phases. A heterodyne beat signal of $f_B$ in frequency generated by the parallel interference optical system 661 is used as a reference signal, the signal control circuit 657 (PLL circuit) generates a storage time control signal ($f_S$) and an exciting light intensity modulating signal ($f_E$) and gives the signals to the one-dimensional CCD sensor 653 and the semiconductor laser driver 677. The modulating frequency $f_E$ may be varied in the range of 1.786 to 88.235 kHz.

Results of experimental operation of the photothermal displacement image detecting apparatus in this embodiment will be explained below. The beat frequency $f_B$ was 100 kHz, and the exciting light modulating frequency $f_E$ was set to 88.235 kHz, the storage frequency $f_S$ of the one-dimensional CCD sensor 653 was set to 47.059 kHz and a clock frequency $f_C$ was set to 14.118 MHz to execute sampling frequency conversion.

Figure 51:
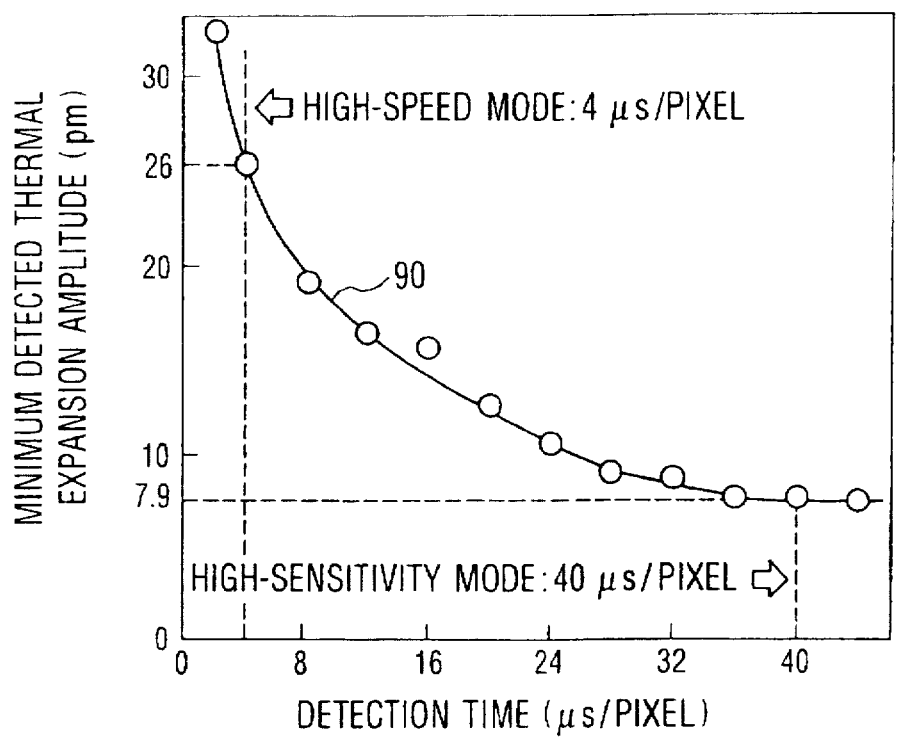
FIG. 51 is a graph showing the relation between detection time and minimum detected thermal expansion amplitude determined by the embodiment of the present invention.

FIG. 51 shows the relation between detection time and minimum detected thermal expansion amplitude. Minimum detection thermal expansion amplitude is an amplitude that meets an inequality: S/N≧1, where the noise amplitude is the standard deviation of a thermal expansion amplitude distribution obtained by detecting the surface of a uniform aluminum mirror as a specimen. It is known from FIG. 51 that the detectable thermal expansion amplitude is inversely proportional to the detection time to the one-half power. In a high-sensitivity mode, in which the detection time is 40 µs/pixel, the minimum detected thermal expansion amplitude was 7.9 pm. In a high-speed mode, in which the detection time is 4 µs/pixel, the minimum detected thermal expansion amplitude was 26 pm.

Figure 52:
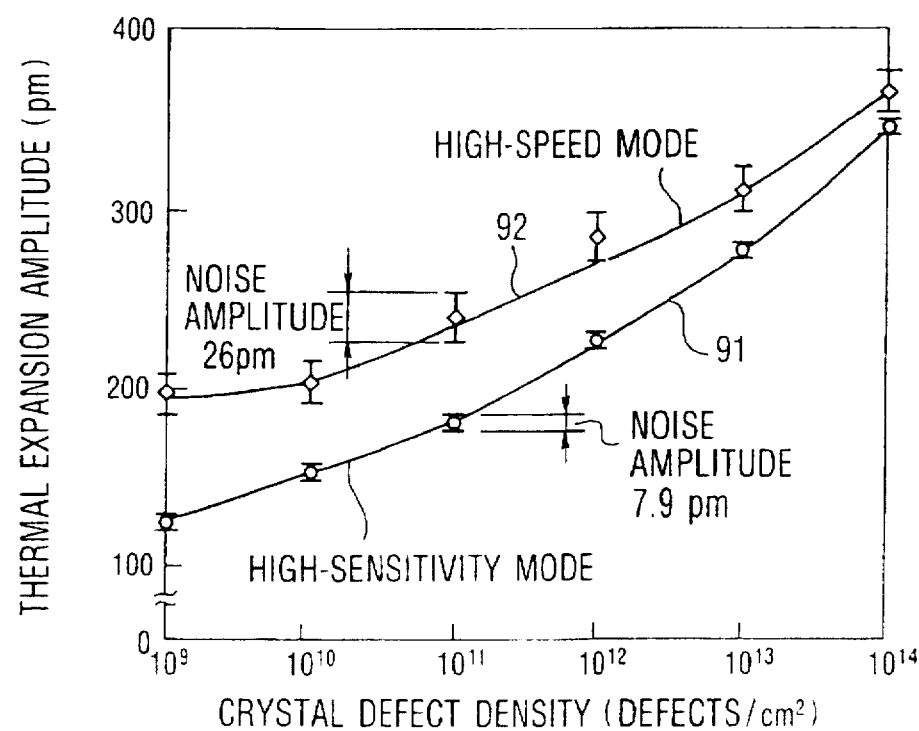
FIG. 52 is a graph showing the relation between thermal expansion amplitude and crystal defects density (in impurity density) caused on a silicon wafer determined by the embodiment of the present invention.

FIG. 52 shows the relation between thermal expansion amplitude and crystal defect density (in impurity density) caused in a silicon wafer by etching. As is obvious from FIG. 52, thermal conductivity decreases and thermal expansion amplitude increases with the increase of defect density. Considering noise amplitude, it is possible to detect a defect density on the order of $10^9$ defects/cm² in the high-sensitivity mode and a defect density on the order of $10^{10}$ defects/cm² in the high-speed mode on the basis of the variation of thermal expansion amplitude resulting from the variation of defect density.

Figure 53A:
FIGS. 53A and 53B are images of crystal defect distribution on a silicon wafer measured by the embodiment of the present invention.
Figure 53B:
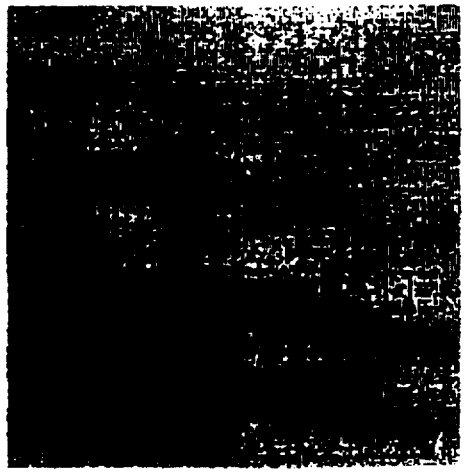
Figure 54:
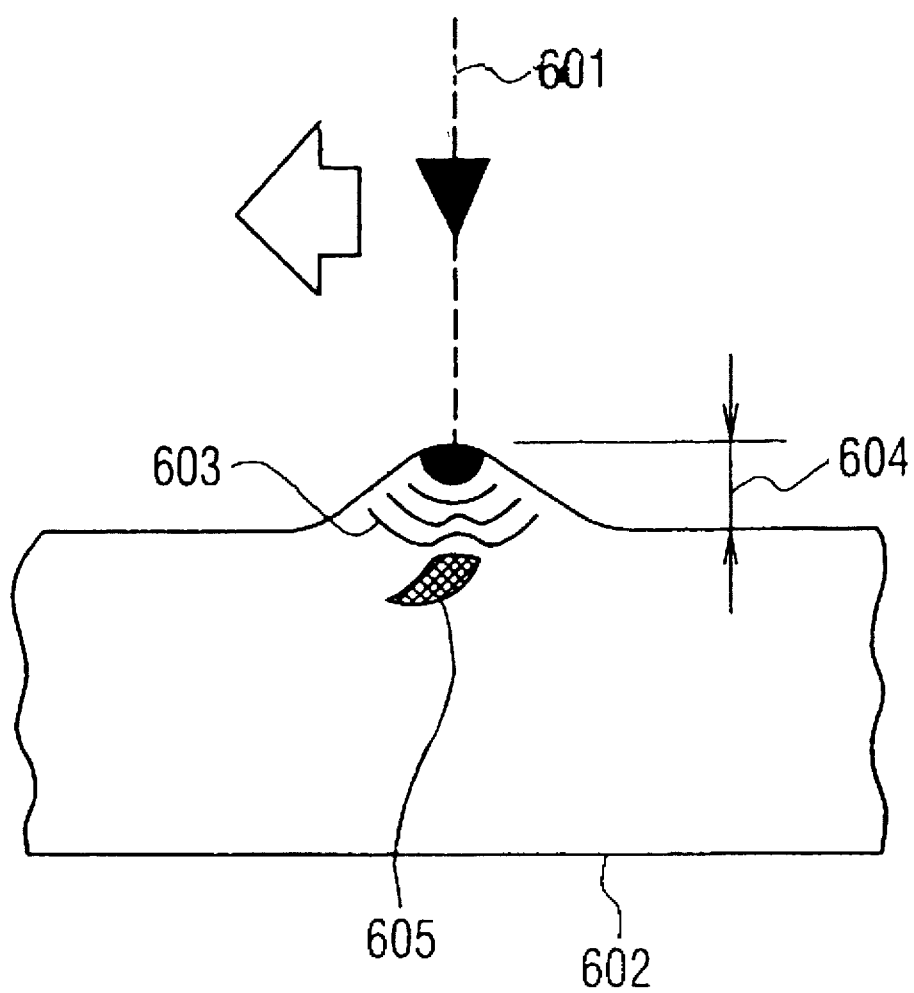
FIG. 54 is a diagrammatic view of assistance in explaining a conventional photothermal displacement process.

FIGS. 53A and 53B are images of a crystal defect distribution on a silicon wafer as a specimen. The specimen was prepared by locally implanting Ar ions in the silicon wafer in an ion density of $10^{15}$ ions/cm² under ion implantation conditions of 300 keV in accelerating energy and 10 mA/cm² in current density to form a defective region. The surface reflectance of the defective region changed scarcely as shown in FIG. 53B, whereas the defective region was manifested in the thermal expansion amplitude image shown in FIG. 53A, which is due to increase in the thermal expansion displacement of the defective region attributable to the reduction of thermal conductivity and resulting rise in surface temperature. The defective region was detected in the high-speed mode in a detection time of 4 µs/pixel and 0.26 s/image, which are about 1/100,000 the times needed by the conventional method. There was no difference in resolution due to parallel excitation between the horizontal and the vertical direction.

As is apparent from the foregoing description, whereas the conventional photothermal displacement method of a point scanning system repeats excitation and detection for individual measuring points, this embodiment excites a plurality of measuring points simultaneously by the parallel-excitation/parallel-interference method using the flat beam and detects the thermal expansion displacements of all the measuring points simultaneously by optical interference. Therefore, the photothermal expansion displacement image detecting method is capable of quickly obtaining two-dimensional information about the surface and the interior of the specimen.

The use of the sampling frequency conversion method using the storing effect of the CCD sensor instead of the conventional synchronous detection method using a lock-in amplifier enables the extraction of a thermal expansion signal from an interference signal detected by the CCD sensor. Thus, the use of the sampling frequency conversion method in combination with the parallel-excitation/parallel-interference method enables both high-speed detection and high-sensitivity detection.

The employment of the common optical path type interferometer for carrying out the parallel interference method cancels out the effect of air fluctuation in the optical path and vibrations of the stage, so that the specimen can be continuously scanned and the detection can be carried out at a very high speed with a high degree of sensitivity.

Since the thermal expansion amplitude is corrected for the effect of reflectance distribution on the surface of the specimen and the thermal expansion phase is corrected for the effect of irregularities in the surface of the specimen, the detection can be achieved in a high accuracy with a high degree of sensitivity.

An optional subsurface layer and points at an optional depth can be detected by setting the intensity modulating frequency for modulating the exciting light beam so that the thermal diffusion length due to the photothermal effect or the photoacoustic effect is equal to or greater than the depth of the subsurface layer of measurement of the specimen.

Accordingly, the photothermal displacement method of the present invention is practically applicable to the measurement of a two-dimensional image which has been difficult to measure by the conventional method, and the inherent high-sensitivity detection ability of the photothermal displacement method can be applied to new practical fields. The present invention is effectively applicable to the two-dimensional evaluation and measurement of crystal defects in semiconductor devices, the in-plane distribution of ion dose and the like, the separation of wiring layers on electronic circuit substrates, crystal defects in surface illuminant lasers and the in-plane distribution of impurities.

The above described embodiment is capable of two-dimensional information about the surface and the interior of a specimen at a high detecting speed by simultaneously exciting a plurality of measuring points simultaneously and simultaneously detecting the thermal expansion displacements at the measuring points by optical interference.

The thermal expansion signal can be extracted from the interference signal provided by the CCD sensor by the sampling frequency conversion method using the storing effect of the CCD sensor, and the detection can be achieved at a high speed with a high degree of sensitivity by using the parallel-excitation/parallel-interference method in combination with the sampling frequency conversion method.

The effect of air fluctuation on the optical path and the vibrations of the stage can be canceled out by carrying out the parallel optical interference method by the common optical path type interferometer, the specimen can be continuously scanned and the detection can be carried out at a very high speed with a high degree of sensitivity.

Since the thermal expansion amplitude is corrected for the effect of reflectance distribution on the surface of the specimen and the thermal expansion phase is corrected for the effect of irregularities in the surface of the specimen, the detection can be achieved in a high accuracy with a high degree of sensitivity.

An optional subsurface layer and points at an optional depth can be detected by setting the intensity modulating frequency for modulating the exciting light beam so that the thermal diffusion length due to the photothermal effect or the photoacoustic effect is equal to or greater than the depth of the subsurface layer of measurement of the specimen.

We claim:

1. A photoacoustic signal detection method comprising:
   irradiating an excitation light focused by a focusing optical system in a state of at least one dimensional linear shape simultaneously, intensity modulated by a desired frequency, to an at least one dimensional linear shape portion being measured on the surface of a sample simultaneously;
   irradiating at least one dimensional linear shape probe light to said one dimensional linear shape portion being measured on the surface of the sample simultaneously;
   detecting at least one dimensional linear shape interference light simultaneously caused by interference between a reflected light of said at least one dimensional linear shape probe light and a specified at least one dimensional linear shape reference light with a detector in conjugate relation with said surface of said sample, said detector provided with a plurality of photoelectric converting elements in the state of the at least one dimensional linear shape corresponding to said one dimensional linear shape portion being measured;
   detecting at least one dimensional linear shape thermal distortions obtained by each of said plurality of frequency components equal to said intensity-modulated frequency at each of a plurality of points along said at least one dimensional linear shape portion being measured in accordance with variation with time on said at least one dimensional linear shape interference light comprising intensity signals detected by said each of photoelectric converting elements of said detector; and
   detecting information relative to the surface and a subsurface at each of the plurality of points along said at least one dimensional linear shape portion being measured of the sample from said at least one dimensional linear shape thermal distortion obtained by each of the plurality of said frequency components at each of the plurality of points along said at least one dimensional linear shape portion.

2. The photoacoustic signal detection method according to claim 1, further comprising the steps of dividing said probe light into two light beams;
   irradiating one of said divided beams of the probe light to the same position as said excitation light;
   irradiating the other of said divided beams of the probe light as a reference light to a vicinity of the irradiated position of said excitation light; and
   detecting an interference light caused by two reflected beams of said one of the divided probe light and said reference light with said detector.

3. The photoacoustic signal detection method according to claim 1, wherein said intensity modulation frequency is set so that the heat diffusion length due to the photoacoustic effect is at least substantially equal to the depth of an interface being measured in said sample.

4. A photoacoustic detection apparatus comprising:
   excitation means for irradiating an intensity-modulated excitation light in a state of at least one dimensional linear shape to an at least one dimensional linear shape portion being measured on a sample surface, said excitation means including a light source and intensity modulation means for generating said excitation light by intensity-modulating a light beam from said light source by a desired frequency;
   light interference means for causing interference between a specified reference light and a reflected light of a probe light by irradiating a specific at least one dimensional linear shape probe light, simultaneously with said excitation light, to said at least one dimensional linear shape portion being measured;

interference light detection means for detecting an interference light caused by said light interference means with a detector in conjugate relation with said sample surface, said detector comprising a plurality of photoelectric converting elements corresponding to said at least one dimensional linear shape portion being measured; and information detection means for detecting at least one dimensional linear shape thermal distortion of a frequency component equal to said intensity-modulation frequency at said at least one dimensional linear shape portion being measured from a detected interference light intensity signal in order to detect information relative to the surface and a subsurface at each of the plurality of points along said at least one dimensional linear shape portion being measured on the sample from detected thermal distortion of the frequency component.

5. The photoacoustic detection apparatus according to claim 4, wherein said excitation means has a cylindrical lens installed along an irradiation path of said excitation light.

6. The photoacoustic detection apparatus according to claim 4, wherein said excitation means includes a minute lens array comprising minute lenses arranged in a straight line along an irradiation path of said excitation light.

7. A photothermal displacement image detecting method comprising:

irradiating a plurality of measuring points on the surface of a specimen with a light beam intensity-modulated at variable frequency $f_E$ to cause periodic thermal expansion displacements in the surface at a plurality of measuring points;

irradiating the measuring points with a second light beam and making a reference light beam of a frequency differing by $f_B$ interfere with the reflected second light beam;

detecting interference light resulting from the interference between the reflected second light beams and the reference light beam by a detector comprising a plurality of photoelectric transducers respectively corresponding to measuring points;

detecting a photothermal displacement signal due to the thermal expansion displacements of the measuring points from interference light intensity signals; and detecting information about the surface and a subsurface layer of the specimen at the plurality of measuring points from the photothermal displacement signal.

8. A photothermal displacement image detecting method according to claim 7, wherein the intensity-modulated light beam for irradiating the plurality of measuring points on the surface of the specimen is a flat beam that forms a continuous straight light line on the specimen.

9. A photothermal displacement image detecting method according to claim 7, wherein the detector integrates the interference light.

10. A photothermal displacement image detecting method according to claim 7, wherein the detector provides the interference light intensity signals in one-dimensional signals in a time series mode from the plurality of photoelectric transducers.

11. The photothermal displacement image detecting method according to claim 9, wherein photothermal displacement signals due to thermal expansion displacements are detected for the plurality of measuring points on the basis of a plurality of integrated detection data obtained through integrating the interference light by the photoelectric transducers of the detector a plurality of times at a period of $1/f_S$ while the frequencies $f_S$, $f_B$ and $f_E$ are controlled at an integral ratio of $8p:8pu+1:8pv-1$ or $8p:8pu-1:8pv+1$, where p, u and v are integers other than zero.

12. A photothermal displacement image detecting method according to claim 7, wherein the reference light beam falls on the surface of the specimen at a position at a distance approximately equal to or greater than the thermal diffusion length from the point irradiated with the intensity-modulated light beam.

13. A photothermal displacement image detecting method according to claim 7, wherein the intensity-modulating frequency $f_E$ is determined so that the thermal diffusion length due to photothermal or photoacoustic effect is approximately equal to or greater than the depth of the objective internal interface of the specimen.

14. A photothermal displacement image detecting apparatus comprising:

a light source;

an intensity modulating means for modulating the intensity of a light beam emitted by the light source at a variable frequency $f_E$;

an exciting means for projecting the intensity-modulated light beam on the surface of a specimen at a plurality of measuring points to cause periodic thermal expansion displacements in the surface of the specimen at the plurality of measuring points;

an interference light producing means for irradiating the plurality of measuring points with a second light beam, and making the reflected second light beam reflected by the measuring points interfere with reference light beams of a frequency differing by $f_B$ to produce interference light;

an interference light detecting means for detecting the interference light by a detector disposed in a conjugate relation with the surface of the specimen and comprising a plurality of photoelectric transducers respectively corresponding to the measuring points;

an information detecting means for detecting photothermal displacement signals due to thermal expansion displacement of the plurality of measuring points from the interference light intensity signals to detect information about the surface and a subsurface layer of the specimen at the plurality of measuring points from the photothermal displacement signals;

a storage means for storing information about the surface and a subsurface layer of the specimen; and a display means for displaying the information about the surface and the subsurface of the specimen.

15. A photothermal displacement image detecting apparatus according to claim 14, wherein the means for irradiating the surface of the specimen at the plurality of measuring points with the intensity-modulated light beam is a flat light beam that forms a continuous straight light line on the surface of the specimen.

16. A photothermal displacement image detecting apparatus according to claim 14, wherein the photoelectric transducers of the detector of the interference light detecting means are storage-type photoelectric transducers.

17. A photothermal displacement image detecting apparatus according to claim 14, wherein the plurality of photoelectric transducers of the detector provide the interference light intensity signals in one-dimensional signals in a time series mode.

18. The photothermal displacement image detecting apparatus according to claim 16 further comprising:

a signal controlling means for controlling the frequencies $f_S$, $f_B$ and $f_E$ at a fixed integral ratio of 8p:8pu+1:8pv−1 or 8p:8pu−1:8pv+1, where p, u and v are integers other than zero; and an information detecting means for detecting photothermal displacement signals due to thermal expansion displacement of the plurality of measuring points on the basis of a plurality of integrated detection data obtained through integrating the interference light by each photoelectric transducer a plurality of times at a time period of $1/f_S$ to detect information about the surface and a subsurface layer of the specimen at the plurality of measuring points from the photothermal displacement signals.

19. A photothermal displacement image detecting apparatus according to claim 14, wherein the reference light beam falls on the surface of the specimen at a position at a distance approximately equal to or greater than the thermal diffusion length from the point irradiated with the intensity-modulated light beam.

20. A photothermal displacement image detecting apparatus according to claim 14, wherein the intensity-modulating frequency $f_E$ is determined so that the thermal diffusion length due to photothermal or photoacoustic effect is approximately equal to or greater than the depth of the objective internal interface of the specimen.

21. A photoacoustic signal detection method comprising:

irradiating an intensity-modulated light to the surface of a sample in a state of at least one dimensional linear shape on the surface of the sample;

irradiating a probe light to a portion of the sample including a portion where said intensity-modulated light is irradiated;

detecting a distribution of interference light caused by interference between a reflection of said probe light and a reference light with a detector;

detecting a distribution of photothermal displacement of the sample from the distribution of the interference light intensity signal; and detecting a distribution of information about the portion of the sample, where said intensity-modulated light is irradiated, from the distribution of photothermal displacement signal.

22. A photoacoustic detection apparatus comprising:

irradiation means for irradiating an intensity-modulated light to the surface of a sample in a state of at least one dimensional linear shape on the surface of the sample;

light interference means for irradiating a probe light to a portion of the sample including a portion where the intensity-modulated light is irradiated, to cause interference between a reflection of said probe light and a reference light;

interference light detection means for detecting a distribution of interference light caused by said light interference means with a detector; and information detection means for detecting a distribution of photothermal displacement of the sample from the distribution of interference light intensity signal to detect a distribution information about the portion of the sample, where said intensity-modulated light is irradiated, from the distribution of photothermal displacement signal.

23. A photoacoustic detection method comprising:

irradiating an intensity-modulated light to the surface of a sample in a state of at least one dimensional linear shape on the surface of the sample;

irradiating a probe light to a portion of the sample near or including at least the same portion as said intensity-modulated light is irradiated;

detecting with a detector a distribution of photoacoustic signal of the sample based on an information of whether said probe light is reflected or passed; and detecting a distribution of information about a portion of the sample, where said probe light is irradiated, from the distribution of said photoacoustic signal.

24. A photoacoustic detection apparatus comprising:

irradiation means for irradiating an intensity-modulated light to the surface of a sample in a state of at least one dimensional linear shape on the surface of the sample;

photoacoustic signal detection means for detecting a distribution of photoacoustic signal of the sample based on an information of reflection or passing of the probe light irradiated to a portion of the sample near or including at least the same portion where said intensity-modulated light is irradiated; and information detection means for detecting a distribution of information about a portion of the sample, where said probe light is irradiated, from the distribution of said photoacoustic signal.

25. A photoacoustic detection apparatus comprising:

an intensity-modulated light emitter including an intensity-modulated light source and an irradiating optics which irradiates said intensity-modulated light to the surface of a sample in a state of at least one dimensional linear shape on the surface of the sample;

a probe light emitter including a probe light source and an irradiating optics which irradiates said probe light to a portion of the sample near or including at least the same portion as said intensity-modulated light is irradiated;

a photoacoustic signal detector which detects an information of a reflection or passing said probe light; and an information detector which detects a distribution of information about a portion of the sample, where said probe light is irradiated, from the distribution of the photoacoustic signal.

\* \* \* \* \*